United States Patent
Jimenez Mayorga et al.

(10) Patent No.: US 7,253,171 B2
(45) Date of Patent: Aug. 7, 2007

(54) UREA DERIVATIVES AS INTEGRIN α4 ANTAGONISTS

(75) Inventors: Juan Miguel Jimenez Mayorga, Barcelona (ES); Jordi Bach Tana, Barcelona (ES); Jesus Maria Ontoria Ontoria, Pomezia (IT); Eloisa Navarro Romero, Barcelona (ES)

(73) Assignee: Laboratorios Almirall, S.A. (ES)

( * ) Notice: Subject to any disclaimer, the term of this patent is extended or adjusted under 35 U.S.C. 154(b) by 506 days.

(21) Appl. No.: 10/466,665

(22) PCT Filed: Jan. 15, 2002

(86) PCT No.: PCT/EP02/00331

§ 371 (c)(1),
(2), (4) Date: Feb. 23, 2004

(87) PCT Pub. No.: WO02/057242

PCT Pub. Date: Jul. 25, 2002

(65) Prior Publication Data

US 2004/0142982 A1  Jul. 22, 2004

(30) Foreign Application Priority Data

Jan. 19, 2001 (ES) .............................. 200100126

(51) Int. Cl.
*A61K 31/497* (2006.01)
*C07D 295/00* (2006.01)
*C07D 211/32* (2006.01)
*C07D 211/06* (2006.01)

(52) U.S. Cl. .................. 514/252.13; 514/300; 544/391; 546/335; 546/234; 546/226; 546/236; 546/294; 560/34

(58) Field of Classification Search ........... 514/252.13; 544/391; 546/335, 234, 226, 236, 294
See application file for complete search history.

(56) References Cited

U.S. PATENT DOCUMENTS 4,705,864 A * 11/1987 Cesa et al. ............... 548/312.1
4,740,611 A    4/1988 Cesa et al.
6,353,099 B1 * 3/2002 DeLaszlo et al. ........... 540/490

FOREIGN PATENT DOCUMENTS

| DE | 199 09 979 | 9/2000 |
|---|---|---|
| WO | WO-92/08464 | 5/1992 |
| WO | WO 97/40031 | 10/1997 |
| WO | WO 98/04247 | 2/1998 |
| WO | WO 98/07718 | 2/1998 |
| WO | WO 98/53818 | 12/1998 |
| WO | WO 98/58902 | 12/1998 |
| WO | WO 99/11606 | 3/1999 |
| WO | WO 99/20617 | 4/1999 |
| WO | WO 99/24035 | 5/1999 |
| WO | WO 99/26921 | 6/1999 |
| WO | WO-99/31099 A1 | 6/1999 |
| WO | WO 99/37604 | 7/1999 |
| WO | WO 00/35864 | 6/2000 |
| WO | WO 00/43415 | 7/2000 |
| WO | WO 00/51974 | 9/2000 |
| WO | WO 00/67746 | 11/2000 |
| WO | WO 00/71572 | 11/2000 |
| WO | WO 00/73260 | 12/2000 |
| WO | WO 01/14328 | 3/2001 |

OTHER PUBLICATIONS

Hcaplus 108:131821.*
Armstrong et al. (1995). "Highly enantioselective capillary electrophorectic separations with dilute solutions of the macrocyclic antibiotic ristocetin A," *J. Chromatography A* 689: 285-304.
Casini et al. (2000). "Carbonic Anhydrase Inhibitors: Water-Soluble 4-Sulfamoylphenylthioureas as Topical Intraocular Pressure-Lowering Agents with Long-Lasting Effects," *J. Med. Chem.* 43:4884-4892.

* cited by examiner

*Primary Examiner*—Thomas McKenzie
*Assistant Examiner*—Binta Robinson
(74) *Attorney, Agent, or Firm*—Finnegan, Henderson, Farabow, Garrett & Dunner, L.L.P.

(57) ABSTRACT

Novel antagonists of α4β1 integrin and/or α4β7 integrin of the general Formula I: wherein R1, R2, R5, L1, L2, Rb, W and Z are as defined in any one of claims 1 to 13, A represents —CH— or a nitrogen atom, and p is from 0 to 4.

23 Claims, No Drawings ated therapeutically in several animal models of inflammation and in humans (X. -D. Yang et al., Proc. Nat. Acad. Sci.

UREA DERIVATIVES AS INTEGRIN α4 ANTAGONISTS

This application is a National Phase of International Application No. PCT/EP01/00331, filed Jan. 15, 2002, and published in English on Jul. 25, 2002, which claims benefit of Spanish Application No. 200100126, filed Jan. 19, 2001. The disclosures of which are herein incorporated in their entirety.

The urea derivatives of the present invention are antagonists of the α4 integrins, both the α4β1 integrin (VLA4, "Very Late Antigen-4 " or CD49d/CD29) and/or the α4β7 integrin (LPAM-1 and α4βp), thereby blocking the binding of α4β1 to its various ligands, such as VCAM-1, osteopontin and regions of fibronectin and/or the binding of α4β7 to its various ligands, such as MadCAM-1, VCAM-1 and fibronectin.

Through this mechanism of action the compounds of the invention inhibit cell (e.g. leukocyte) adhesion, activation, migration, proliferation and differentiation and are useful therefore in the treatment, prevention and suppression of immune or inflammatory disorders and of other diseases mediated by α4β1 and/or α4β7 binding and/or by cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, atopic dermatitis, myocarditis, inflammatory bowel disease including ulcerative colitis and Crohn's disease, certain types of toxic and immune-based nephritis, contact dermal hypersensitivity, psoriasis, tumor metastasis, atherosclerosis and cerebral ischemia.

This invention also relates to compositions containing such compounds, to processes for their preparation, and to methods of treatment using such compounds. According to one aspect of the present invention we provide a particular group of compounds which are potent inhibitors of the binding of α4β1 and/or α4β7 integrins to their ligands.

Many physiological processes require that cells come into close contact with other cells and/or extracellular matrix. Such adhesion events may be required for cell activation, migration, proliferation and differentiation. Cell-cell and cell-matrix interactions are mediated through several families of Cell Adhesion Molecules (CAMs) including the selecting, integrins, cadherins and the immunoglobulins superfamily. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions. One family of adhesion molecules that is believed to play a particularly important role in regulating immune and inflammatory responses is the integrin family.

The integrin family is made up of structurally and functionally related glycoproteins consisting of α and β heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of Integrins", Medicinal Research Rev., 14, 195 (1995) and V. W. Engleman et al., "Cell Adhesion Integrins as Pharmaceutical Targets" in Ann. Repts. In Medicinal Chemistry, Vol. 31, J. A. Bristol, Ed.; Acad. Press, NY, 1996, p. 191). At least 14 different integrin α chains and 8 different integrin β chains have been identified (A. Sonnenberg, Current Topics in Microbiology and Immunology, 184, 7, (1993)). The members of the family are typically named according to their heterodimer composition although trivial nomenclature is widespread in this field. Thus the integrin termed α4β1 consists of the integrin α4 chain associated with the integrin β1 chain, and the integrin termed α4β7 consists of the integrin α4 chain associated with the integrin β7 chain; Not all the potential pairings of integrin α and β chains have yet been observed in nature and the integrin family has been subdivided based on the pairings that have been recognized (A. Sonnenberg, ibid; S. A. Mousa et al., Drugs Discovery Today, 2, 187 (1997)).

One particular integrin subgroup of interest involves the α4 chain, which can pair with two different β chains, β1 and β7. α4β1 (VLA-4, "very late antigen-4"; or CD49d/CD29) is an integrin expressed on all leukocytes, except platelets, including dendritic cells and macrophage-like cells and is a key mediator of the cell-cell and cell-matrix interactions of these cell types (see M. E. "VLA Proteins in the Integrin Family: Structures, Functions, and their Role on Leukocytes." Ann. Rev. Immunol., 8, 365 (1990)). The ligands for α4β1 include vascular cell adhesion molecule-1 (VCAM-1), the CS-1 domain of fibronectin (FN) and osteopontin. VCAM-1 is a member of the Ig superfamily and is expressed in vivo on endothelial cells at sites of inflammation. (See R. Lobb et al., "Vascular Cell Adhesion Molecule-1" in Cellular and Molecular Mechanisms of Inflammation, C. G. Cochrane and M. A. Gimbrone, Eds.; Acad. Press, San Diego, 1993, p. 151). VCAM-1 is produced by vascular endothelial cells in response to pro-inflammatory cytokynes (see A. J. H. Gearing and W. Newman, "Circulating adhesion molecules in disease.", Immunol. Today, 14, 506 (1993)). The CS-1 domain is a 25 aminoacid sequence that arises by alternative splicing within a region of fibronectin. (For a review, see R. O. Hynes "Fibronectins", Springer-Verlag, NY, 1990). A role for α4β1/CS-1 interactions in inflammatory conditions has been proposed (see M. J. Elices, "The integrin α4β1 (VLA4) as a therapeutic target" in Cell Adhesion and Human disease, Ciba Found. Symp., John Wiley & Sons, NY, 1995, p. 79). Osteopontin is expressed by a number of cell types including osteoclasts, osteoblasts, macrophages, activated T-cells, smooth muscle cells and epithelial cells (C. M. Giachelli et al., "Molecular and cellular biology of osteopontin.: Potential role in cardiovascular disease". Trends Card. Med., 5, 88 (1995)).

α4β7 (also referred to as LPAM-1 and α4βp) is an integrin expressed on leukocytes and is a key mediator of leukocyte trafficking and homing in the gastrointestinal tract (see C. M. Parker et al., Proc. Nat. Acad. Sci. USA, 89, 1924 (1992)). The ligands for α4β7 include mucosal addressing cell adhesion molecule-1 (MadCAM-1) and, upon activation of a4p7, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hammann et al., J. Immunol., 152, 3282 (1994)). MadCAM-1 can be induced in vitro by proinflammatory stimuli (See E. E. Sikarosky et al., J. Immunol., 151, 5239 (1993)). MadCAM-1 is selectively expressed at sites of lymphocyte extravasation and specifically binds to the integrin α4β7.

Neutralizing anti-α4 antibodies or blocking peptides that inhibit the interaction between α4β1 and/or α4β7 and their ligands have proven efficacious both prophylactically and therapeutically in several animal models of inflammation and in humans (X. -D. Yang et al., Proc. Nat. Acad. Sci.

USA, 90, 10494 (1993), P. L. Chisholm et al., Eur. J. Immunol., 23, 682 (1993), T. A. Yednock et al., Nature, 356, 63 (1992), R. R. Lobb et al., J. Clin. Invest., 94, 1722 (1994), J. Relton, Drug News Perspect., 14, 346 (2001), N. Turbridy et al., Neurology, 53, 466 (1999)). The primary mechanism of action of such antibodies appears to be the inhibition of lymphocyte and monocyte interactions with CAMs associated with components of the extracellular matrix and vascular endothelium, thereby limiting leukocyte migration to extravascular sites of injury or inflammation and/or limiting the priming and/or activation of leukocytes.

Since the discovery of their key role in mediating inflammatory pathophysiology, α4β1 and α4β7 have received considerable attention as drug design targets. Important advances have been made in identifying potent and selective candidates for further development strongly suggesting that α4β1 and α4β7 should be tractable small molecule targets (S. P. Adams' et al., "Inhibitors of Integrin Alpha 4 Beta 1 (VLA-4)" in Ann. Repts. In Medicinal Chemistry, Vol. 34, W. K. Hagmann, Ed.; Acad. Press, NY, 1999, p. 179).

There still remains a need for low molecular weight, specific inhibitors of α4β1 and. α4β7-dependent cell adhesion that have improved pharmacokinetic and pharmacodynamic properties such as oral bioavailability and significant duration of action. Such compounds would prove to be useful for the treatment, prevention or suppression of various pathologies mediated by α4β1 and α4β7 binding and cell adhesion and activation.

Compounds with related structures have been described as calcitonin mimetics and protein tyrosine phosphatase inhibitors in two patents.

In the patent application WO9937604 (U.S. Ser. No. 99/01151) urea derivatives are described, which are represented by the following general formula.

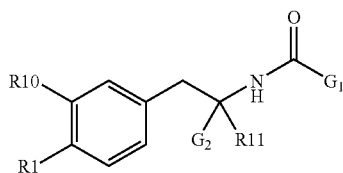

Wherein:
R1 is substituted aryl and substituted alkylaryl.
n and m can be 0
Z and X are independently selected from the group NH, O, S or NR.
R3 is 2,5 disubstituted aryl wherein the substituents are each independently alkyl or aryl.

These compounds clearly differ from those of the present invention in terms of the definition of groups R3 and R1 and the mechanism of action and the indications claimed.

In addition, another patent application WO9911606 (U.S. Ser. No. 98/17327) discloses compounds represented by formula:

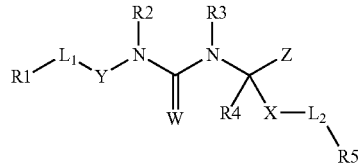

Wherein:
G1 may be —NR8R9
G2 is CONHR3, H, CH$_2$OH, CH═CHR3
R8 is a substituted phenyl, naphtyl and heterocyclic ring.

These compounds are also different from the compounds claimed in the present invention because G2 is always an amide, hydrogen, primary alcohol or alkene.

WO 00/67746, WO 00/51974, WO 00/43415, WO 00/73260, WO 98/58902, WO 98/04247, WO 99/26921, WO 98/53818 and WO 00/71572 disclose compounds that inhibit the binding of α4β1 and/or α4β7 integrins to their receptors and their use in the treatment or prevention of diseases mediated by α4β1 and/or α4β7 binding and/or by cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, atopic dermatitis, myocarditis, inflammatory bowel disease including ulcerative colitis and Crohn's disease, certain types of toxic and immune-based nephritis, contact dermal hypersensitivity, psoriasis, tumor metastasis, atherosclerosis and cerebral ischemia.

The present invention provides a compound according to Formula I:

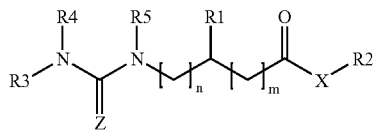

Formula I or a pharmaceutically acceptable salt thereof, wherein:
R1 is $C_{3-10}$alkyl, $C_{3-10}$alkenyl, $C_{3-10}$alkynyl, cycloalkyl, cycloalkyl-$C_{1-10}$alkyl, cycloalkyl-$C_{2-10}$alkenyl, cycloalkyl-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl, aryl-$C_{1-10}$alkyl, aryl-$C_{2-10}$alkenyl, aryl-$C_{2-10}$alkynyl, heteroaryl, heteroaryl-$C_{1-10}$alkyl, heteroaryl-$C_{2-10}$alkenyl, or heteroaryl-$C_{2-10}$alkynyl; wherein said alkyl, alkenyl, and alkynyl groups or moieties are unsubstituted or substituted with one to four substituents, which may be the same or different and are independently selected from Ra; and wherein said cycloalkyl, heterocyclyl, aryl and heteroaryl groups or moieties are unsubstituted or substituted with one to four substituents, which may be the same or different and are independently selected from Rb;

R2 is hydrogen, $C_{1-8}$alkyl, $C_{0-2}$alkylcycloalkyl, $C_{0-2}$alkylaryl, $C_{0-2}$alkylheteroaryl, cycloalkyl-$C_{0-2}$alkyl, aryl-$C_{0-2}$alkyl or heteroaryl-$C_{0-2}$alkyl, wherein said aryl and heteroaryl groups or moieties are unsubstituted or substituted with one to four substituents, which may be the same or different and are independently selected from Ra;

R3 and R4 are independently hydrogen or $C_{1-4}$alkyl;

R2 and R3, together with the atoms to which they are attached, may form a 4-8 membered ring;

R5 is $C_{1-6}$alkyl, cycloalkyl, cycloalkyl-$C_{1-4}$alkyl, heterocyclyl, heterocyclyl-$C_{1-4}$alkyl, aryl, aryl-$C_{1-4}$alkyl, heteroaryl, or heteroaryl-$C_{1-4}$alkyl; wherein said alkyl groups or moieties are unsubstituted or substituted with one to four substituents, which may be the same or different and are independently selected from Ra; and wherein said cycloalkyl, heterocyclyl, aryl and heteroaryl groups or moieties are unsubstituted or substituted with one to four substituents, which may be the same or different and are independently selected from Rb;

L1 is —S—, —S(O)—, —S(O)$_2$—, —C(O)—, —C(O)O—, —C(S)—, —N(Rc)—, —CH$_2$—, —CH$_2$N(Rc)—, —CON(Rc)—, —CSN(Rc)—, —N(Rc)CO—, —N(Rc)CS—, —S(O)$_2$N(Rc)— or —N(Rc)S(O)$_2$—;

L2 is a covalent bond, —O—, —S—, —S(O)—, —S(O)$_2$—, —C(O)—, —C(O)O—, —OC(O)—, —C(S)—, —N(Rc)—, —CON(Rc)—, —OC(O)N(Rc), —CSN(Rc)—, —N(Rc)CO—, —N(Rc)C(O)O—, —N(Rc)CS—, —S(O)$_2$N(Rc)—, —N(Rc)S(O)$_2$—, —N(Rc)CON(Rc)—, or —N(Rc)CSN(Rc)—, wherein if two Rc substituents are present, these may be the same or different;

W is O, S, NH, N(Rc), or NCN;

X is —(CH$_2$)$_n$aryl-, or —(CH$_2$)$_n$heteroaryl-; wherein said aryl and heteroaryl moieties are unsubstituted or substituted with one to four substituents, which may be the same or different and are independently selected from Rb;

Y is monocyclic aryl, or monocyclic heteroaryl containing one or two heteroatoms selected from N, O and S, wherein said aryl and heteroaryl moieties are unsubstituted or substituted with one to four substituents, which may be the same or different and are independently selected from Rb;

Z is —C(O)ORd, —P(O)$_2$ORd, —S(O)$_2$ORd, —S(O)$_2$N(Rd)(Rd), —C(O)NH$_2$, —C(O)N(Re)S(O)$_2$Rd, —S(O)$_2$N(Re)C(O)Rd, -5-tetrazolyl, or —C(O)Rd; wherein if two Rd groups are present these may be the same or different;

Ra is —OH, —ORe, —NO$_2$, halogen, —S(O)Re, —S(O)$_2$Re, —SRe, —S(O)$_2$ORe, —S(O)NReRe —S(O)$_2$NReRe, —NReRe, —O(CReRe)mNReRe, —C(O)Re, —CO$_2$Re, —CO$_2$(CReRe)mCONReRe, —OC(O)Re, —CN, —C(O)NReRe, —NReC(O)Re, —OC(O)NReRe, —NReC(O)ORe, —NReC(O)NReRe, —CRe(N—ORe), —CFH$_2$, —CF$_2$H, or —CF$_3$; wherein if two or more Re groups are present these may be the same or different;

Rb is a group selected from —OH, —ORe, —NO$_2$, halogen, —S(O)Re, —S(O)$_2$Re, —SRe, —S(O)$_2$ORe, —S(O)NReRe —S(O)$_2$NReRe, —NReRe, —O(CReRe)mNReRe, —C(O)Re, —CO$_2$Re, —CO$_2$(CReRe)mCONReRe, —OC(O)Re, —CN, —C(O)NReRe, —NReC(O)Re, —OC(O)NReRe, —NReC(O)ORe, —NReC(O)NReRe, —CRe(N—ORe), —CFH$_2$, —CF$_2$H, —CF$_3$, C$_{1-6}$alkyl, C$_{2-4}$alkenyl, C$_{2-4}$alkynyl, cycloalkyl, cycloalkyl-C$_{1-4}$alkyl, heterocyclyl, heterocyclyl-C$_{1-4}$alkyl, aryl, aryl-C$_{1-4}$alkyl, heteroaryl or heteroaryl-C$_{1-4}$alkyl; wherein said alkyl, alkenyl, alkynyl, cycloalkyl, heterocyclyl, aryl and heteroaryl groups or moieties are unsubstituted or substituted with one to four substituents which may be the same or different and are independently selected from Ra;

Rc is hydrogen, C$_{1-10}$ alkyl or cycloalkyl; wherein said alkyl or cycloalkyl groups or moieties are unsubstituted or substituted with one to four substituents which may be the same or different and are selected from Ra;

Rd is hydrogen, C$_{1-6}$alkyl, cycloalkyl, cycloalkyl-C$_{1-4}$alkyl, heterocyclyl, heterocyclyl-C$_{1-4}$alkyl, aryl, aryl-C$_{1-4}$alkyl, heteroaryl, or heteroaryl-C$_{1-4}$alkyl; wherein said alkyl, cycloalkyl, heterocyclyl, aryl and heteroaryl groups or moieties are unsubstituted or substituted with one to four substituents which may be the same or different and are independently selected from Ra;

Re is hydrogen, or C$_{1-4}$alkyl.

n is an integer from 0 to 2;

m is an integer from 1 to 6;

As used herein, an alkyl group or moiety is a straight or branched group or moiety, which, unless otherwise specified, contains from 1 to 10 carbon atoms. A C$_{1-10}$ alkyl group or moiety is typically a C$_{1-6}$ alkyl group or moiety. A C$_{1-6}$ alkyl group or moiety is generally a C$_{1-4}$ alkyl group or moiety such as methyl, ethyl, n-propyl, i-propyl, n-butyl and t-butyl. A C$_{3-10}$ alkyl group or moiety is typically a C$_{3-6}$ alkyl group or moiety, for example propyl, butyl, pentyl or hexyl. A C$_{0-2}$ alkyl group or moiety may be a bond, a methyl group or an ethyl group. An alkyl group or moiety may be unsubstituted or substituted by one to four substituents, the substituents, unless otherwise specified, being selected from Ra. Where two or more substituents are present, these may be the same or different.

As used herein, an alkenyl group or moiety is a straight or branched group or moiety, which, unless otherwise specified, contains from 2 to 10 carbon atoms. One or more double bonds may be present in the alkenyl group or moiety, typically one double bond. A C$_{2-10}$ alkenyl group or moiety is typically ethenyl or a C$_{3-10}$ alkenyl group or moiety. A C$_{3-10}$ alkenyl group or moiety is typically a C$_{3-6}$ alkenyl group or moiety, for example propenyl, butenyl, pentenyl or hexenyl. A C$_{2-4}$ alkenyl group or moiety is ethenyl, propenyl or butenyl.

As used herein an alkynyl group or moiety is a straight or branched group or moiety which, unless otherwise specified, contains from 2 to 10 carbon atoms. One or more triple bonds, and optionally one or more double bonds may be present in the alkynyl group or moiety, typically one triple bond. A C$_{2-10}$ alkynyl group or moiety is typically ethynyl or a C$_{3-10}$ alkynyl group or moiety. A C$_{3-10}$ alkynyl group or moiety is typically a C$_{3-6}$ alkynyl group or moiety, for example propynyl, butynyl, pentynyl or hexynyl. A C$_{2-4}$ alkynyl group or moiety is ethynyl, propynyl or butynyl.

As used herein a cycloalkyl group or moiety is typically a 3- to 10-membered group or moiety, preferably a 3- to 6-membered group or moiety, which may be a monocyclic ring or which may consist of two or more fused rings. Examples of cycloalkyl groups or moieties include cyclopropyl, cyclopentyl and cyclohexyl.

The 4- to 8-membered ring which may be formed by R2 and R3 is a saturated or unsaturated, aromatic or non-aromatic ring which is typically a 5- or 6-membered ring. Typically, the only heteroatoms present are the two nitrogen atoms attached to R2 and R3. The ring may be unsubstituted or substituted in any position by one to four substituents, which are the same or different and are selected from Ra.

As used herein a heterocyclyl group or moiety is typically a non-aromatic, saturated or unsaturated, 3- to 10-membered group or moiety, typically a 5- or 6-membered group or moiety, containing one or more heteroatoms, for example 1, 2 or 3 heteroatoms, selected from N, O and S. Preferably it is unsaturated. A heterocyclyl group or moiety may be a monocyclic ring or may consist of two or more fused rings, at least one of which contains a heteroatom selected from N, O and S. Examples of heterocyclyl groups and moieties include piperidyl, piperazinyl, azetidinyl, aziridyl, morpholinyl, thiomorpholinyl, imidazolidinyl, quinuclidinyl, thioxanyl, thiazolidinyl, tetrahydrofuranyl, tetrahydrothiophenyl, 1,3-dioxanyl and 1,4-dioxanyl. A preferred heterocycly group or moiety is piperazinyl.

As used herein an aryl group or moiety typically contains from 6 to 10 carbon atoms. An aryl group or moiety may be a monocyclic ring, for example phenyl, or, unless otherwise specified, may consist of two or more fused rings, for example naphthyl. An aryl group or moiety is typically unsubstituted or substituted with one or two substituents.

Preferred substituents for an aryl group or moiety generally include nitro, chloro, methyl and methoxy groups.

As used herein a heteroaryl group or moiety is, typically a 5- to 10-membered group or moiety such as a 5- or 6-membered group or moiety and contains one or two, or unless otherwise specified may contain three or more, heteroatoms selected from N, O and S. A heteroaryl group may be a monocyclic ring such as pyridyl, thienyl, furanyl, pyrrolyl, imidazolyl, pyrazolyl, pyrazinyl, pyrimidinyl, pyridazinyl or triazolyl, or, unless otherwise specified, may consist of two or more fused rings, at least one of which contains a heteroatom selected from N, O and S. Examples of fused heteroaryl groups include benzothiazolyl, indolyl, indazolyl, purinyl, quinolyl, isoquinolyl, phthalazinyl, naphthyridinyl, quinoxalinyl, quinazolinyl and cinnolinyl. Preferred heteroaryl groups or moieties include pyridyl and thienyl. A heteroaryl group may be unsubstituted or substituted with one or two substituents. Preferred substituents for a heteroaryl group or moiety generally include nitro, chloro, methyl and methoxy groups.

As used herein a halogen is typically fluorine, chlorine or bromine.

Preferably, R1 is $C_{3-6}$alkyl, cycloalkyl, cycloalkyl-$C_{1-4}$ alkyl, heterocyclyl, heterocyclyl-$C_{1-4}$alkyl, aryl, aryl-$C_{1-4}$ alkyl, heteroaryl, heteroaryl-$C_{1-4}$alkyl; wherein said alkyl groups or moieties are unsubstituted; and wherein said cycloalkyl, heterocyclyl, aryl and heteroaryl groups or moieties are unsubstituted or substituted with one to four substituents, which may be the same or different and are independently selected from Rb. More preferably, R1 is cyclohexyl, cyclohexylmethyl, phenyl, benzyl, piperidinyl, piperidinylmethyl, piperazinyl, piperazinylmethyl, thienyl, thienylmethyl, tert-butyl or cyclopentyl wherein R1 is either unsubstituted or substituted with one or two groups Rb, unless R1 is tert-butyl in which case it is unsubstituted or substituted by one or two groups Ra. The most preferred groups Rb which may represent substituents on R1 include $C_{1-4}$ alkyl, nitro, halogen and —$OC_{1-4}$alkyl, more preferably methyl, nitro, chloro or methoxy.

Preferably, L1 is —$CH_2$—, —S—, —S(O)—, —S(O)$_2$—, —C(O)—, —NH—, —CON(Rc)—, or —S(O)$_2$N(Rc)—, the carbon and sulphur atoms being attached to the group Y in the latter two moieties. Typically, these preferred L1 moieties are selected from —$CH_2$—, —S(O)—, —S(O)$_2$—, —C(O)—, —NH—, —CON(Rc)—, and —S(O)$_2$N(Rc)— More preferably, L1 is —$CH_2$—, —S(O)—, —S(O)$_2$, —CON(Rc)—, or —S(O)$_2$N(Rc)—, wherein Rc is preferably hydrogen or $C_{1-4}$ alkyl, most preferably hydrogen. Typically, these more preferred L1 moieties are selected from —S(O)—, —S(O)$_2$—, —CON(Rc)—, and —S(O)$_2$N(Rc)—, wherein Rc is preferably hydrogen or $C_{1-4}$ alkyl, most preferably hydrogen.

When Y is monocyclic aryl it is preferably phenyl. When Y is monocyclic heteroaryl it is preferably thienyl or pyridyl, wherein the thienyl and pyridyl groups are typically attached at the 3-position. Most preferably Y is monocyclic aryl. The substituent L1-R1 may be in any position on the ring, typically the 2, 4 or 6-position. Y, in addition to being substituted with the group L1-R1, may also be substituted with one or more groups Rb. Y is generally substituted by none, one or two groups Rb, most preferably none or one group Rb. The group(s) Rb, if present, may be in any position on the ring. Preferably the substituent Rb on the group Y is represented by a group Ra, more preferably a halogen or a group —ORe, —OH or —$CF_3$, in particular a chlorine, bromine or —OMe group.

Typically, R2 is hydrogen, $C_{1-6}$-alkyl, cycloalkyl-$C_{0-2}$ alkyl, aryl-$C_{0-2}$alkyl or heteroaryl-$C_{0-2}$alkyl, wherein said aryl and heteroaryl groups and moieties are unsubstituted or substituted with one to four substituents which may be the same or different and are independently selected from Ra. R2 is preferably hydrogen, $C_{1-5}$ alkyl, cyclohexylmethyl, benzyl or cyclopropylmethyl, more preferably hydrogen, $C_{1-5}$ alkyl or cyclopropylmethyl. Typically, these preferred R2 substituents are selected from hydrogen and $C_{1-4}$ alkyl, more typically hydrogen and methyl. R3 is preferably hydrogen or methyl, most preferably hydrogen. R4 is preferably hydrogen or methyl, most preferably hydrogen. W is preferably O or S.

Typically, Z is —C(O)ORd, —C(O)NH$_2$, —C(O)N(Re) S(O)$_2$Rd, -5-tetrazolyl or —C(O)Rd, wherein if two Rd groups are present they may be the same or different. Z is preferably —C(O)ORd, —P(O)$_2$ORd, —S(O)$_2$ORd, —S(O)$_2$N(Rd)(Rd), —S(O)$_2$N(Re)C(O)Rd, -5-tetrazolyl, or —C(O)Rd, more preferably —C(O)ORd, wherein Rd is preferably hydrogen or $C_{1-6}$ alkyl. The most preferred groups Z are C(O)OH and —C(O)OMe.

X is preferably a group —$CH_2$aryl- or —$CH_2$-heteroaryl-, most preferably a benzyl group. The substitutuent L2-R5 may be in any position on the ring, typically the 2, 4 or 6-position. X, in addition to being substituted with the group L2-R5, may also be substituted with one or more groups Rb. The group(s) Rb, if present, may be in any position on the ring. Typically, X is not substituted by a group Rb, but if such a group is present it is typically a halogen, —$C_{1-6}$alkyl, —OH, —ORe or —$CF_3$, most preferably chlorine, bromine, methyl or —OMe.

L2 is preferably a covalent bond or a group —N(Rc) CO—, —OC(O)N(Rc)—, —N(Rc)— or —O—, the nitrogen and oxygen atoms being attached to the group X in the first two moieties. Typically, these preferred L2 definitions are selected from a covalent bond and —N(Rc)CO—, —OC(O)N(Rc)—and —O—, wherein Rc is typically hydrogen or $C_{1-4}$ alkyl. In particular, L2 is more preferably a group —N(Rc)CO— or —OC(O)N(Rc)—, —N(Rc)— or —O— wherein Rc is preferably hydrogen or $C_{1-4}$ alkyl, most preferably hydrogen. R5 is preferably an aryl, aryl-$C_{1-4}$ alkyl, heteroaryl or heteroaryl-$C_{1-4}$ alkyl group, more preferably an aryl or heteroaryl group such as phenyl, pyridyl or naphthyridinyl wherein the aryl or heteroaryl group is unsubstituted or substituted with one or two substituents Rb. Typically the aryl or heteroaryl group is substituted with two substituents Rb which may be in any position on the ring such as the 2 and 6 positions. The substituents Rb attached to R5 are preferably halogen, $C_{1-6}$ alkyl, —OH, —$CF_3$ or —ORe, more preferably chlorine, bromine, methyl or —OMe. The most preferred groups R5 include 2,6-dichlorophenyl, 2,6-dimethoxyphenyl, 3,5-dichloropyridyl, methyl, 4-methylpiperazine, 2-cyanophenyl, 2-methoxyphenyl, [2,6]naphtyridinyl, [2,7]naphtyridinyl, 3-cyano[1,6] naphtyridinyl. Typically, these most preferred R5 groups are selected from 2,6-dichlorophenyl, 2,6-dimethoxyphenyl and 3,5-dichloropyridyl.

Preferred examples of the group -L2-R5 include 2,6-dichlorophenyl, 2,6-dimethoxyphenyl, 3,5-dichloropyridyl, 2,6-dichlorophenoxy, 2,6-dimethoxyphenoxy, 3,5-dichloropyridyloxy, 2,6-dichlorobenzoylamino, 2,6-dimethoxybenzoylamino, 3,5-dichloropyridine-4-carbonylamino, N,N-dimethylcarbamoyl, 4-methylpiperazincarbamoyl, 2,6-dichlorobenzylamino, 3,5-dichloropyrdin-4-methylenamino, 2-cyanophenyl, 2-methoxyphenyl, [2,6] naphtyridinyloxy, [2,6]naphtyridinylamino, [2,7] naphtyridinyloxy, [2,7]naphtyridinylamino and 3-cyano[1, 6]naphtyridinylamino, in particular 2,6-dichlorobenzoylamino, 2,6-dimethoxybenzoylamino, 3,5-dichloropyridine-4-carbonylamino, 2,6-dichlorobenzylamino, 3,5-dichloropyridin-4-methylenamino, [2,6]naphtyridinyloxy, [2,6]naphtyridinylamino, [2,7]naphtyridinyloxy and [2,7]naphtyridinylamino. Typically, these preferred examples are selected from 2,6-dichlorophenyl, 2,6-dimethoxyphenyl, 3,5-dichloropyridyl, 2,6-dichlorophenoxy, 2,6-dimethoxyphenoxy, 3,5-dichloropyridyloxy, 2,6-dichlorobenzoylamino, 2,6-dimethoxybenzoylamino and 3,5-dichloropyridine-4-carbonylamino, in particular 2,6-dichlorobenzoylamino, 2,6-dimethoxybenzoylamino and 3,5-dichloropyridine-4-carbonylamino.

The compounds of Formula I of the present invention may include enantiomers depending on their asymmetry or diastereoisomers. The single isomers and mixtures of the isomers fall within the scope of the present invention.

Preferred compounds of formula I have S-configuration at the carbon atom alpha to the group Z.

Most preferred compounds of formula I for use in the present invention are the compounds of Formula Ia described hereinbelow, and pharmaceutically acceptable salts thereof:

Formula Ia

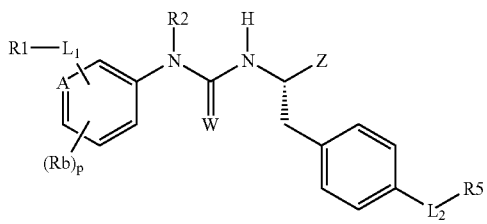

wherein R1, R2, R5, L1, L2, Rb, W and Z are as defined above, the preferred definitions of each of these substituents also being defined above, A represents a —CH— group or a nitrogen atom, and p is from 0 to 4, preferably 0, 1 or 2.

Particularly preferred compounds of formula Ia include:

(S)-2-{3-[2-(Cyclohexylmethylcarbamoyl)phenyl]ureido}-3-[4-(2,6-dichlorobenzoylamino)phenyl]propionic acid methyl ester (S)-2-{3-[2-(Cyclohexylmethylcarbamoyl)phenyl]ureido}-3-[4-(2,6-dichlorobenzoylamino)phenyl]propionic acid (S)-2-{3-[2-(Cyclohexylmethylcarbamoyl)-6-methoxyphenyl]ureido}-3-[4-(2,6-dichlorobenzoylamino)phenyl]propionic acid methyl ester (S)-2-{3-[2-(Cyclohexylmethylcarbamoyl)-6-methoxyphenyl]ureido}-3-[4-(2,6-dichlorobenzoylamino)phenyl]propionic acid (S)-3-[4-(2,6-Dichlorobenzoylamino)phenyl]-2-{3-[2-(methylphenylcarbamoyl)phenyl]ureido}propionic acid methyl ester (S)-3-[4-(2,6-Dichlorobenzoylamino)phenyl]-2-{3-[2-(methylphenylcarbamoyl)phenyl]ureido}propionic acid (S)-3-[4-(2,6-Dichlorobenzoylamino)phenyl]-2-{3-[2-(piperidine-1-carbonyl)phenyl]ureido}propionic acid methyl ester (S)-3-[4-(2,6-Dichlorobenzoylamino)phenyl]-2-{3-[2-(piperidine-1-carbonyl)phenyl]ureido}propionic acid (S)-3-[4-(2,6-Dichlorobenzoylamino)phenyl]-2-{3-[5-methoxy-2-(piperidine-1-carbonyl)phenyl]ureido}propionic acid methyl ester (S)-3-[4-(2,6-Dichlorobenzoylamino)phenyl]-2-{3-[5-methoxy-2-(piperidine-1-carbonyl)phenyl]ureido}propionic acid (S)-2-{3-[2-(Cyclohexylisopropylcarbamoyl)-5-methoxyphenyl]ureido}-3-[4-(2,6-dichlorobenzoylamino)phenyl]propionic acid methyl ester (S)-2-{3-[2-(Cyclohexylisopropylcarbamoyl)-5-methoxyphenyl]ureido}-3-[4-(2,6-dichlorobenzoylamino)phenyl]propionic acid (S)-3-[4-(2,6-Dichlorobenzoylamino)phenyl]-2-[3-(2-phenylaminophenyl)ureido]propionic acid methyl ester (S)-3-[4-(2,6-Dichlorobenzoylamino)phenyl]-2-[3-(2-phenylaminophenyl)ureido]propionic acid (S)-2-[3-(4-Benzenesulfonylphenyl)ureido]-3-[4-(2,6-dichlorobenzoylamino)phenyl]propionic acid methyl ester (S)-2-[3-(4Benzenesulfonylphenyl)ureido]-3-[4-(2,6-dichlorobenzoylamino)phenyl]propionic acid (S)-3-[4-(2,6-Dichlorobenzoylamino)phenyl]-2-{3-[4-(4-nitrobenzenesulfonyl)phenyl]ureido}propionic acid methyl ester (S)-3-[4-(2,6-Dichlorobenzoylamino)phenyl]-2-{3-[4-(4-nitrobenzenesulfonyl)phenyl]ureido}propionic acid (S)-3-[4-(2,6-Dichlorobenzoylamino)phenyl]-2-{3-[2-(4-methylpiperazine-1-carbonyl)phenyl]ureido}propionic acid (S)-2-{3-[2-(Butylthiophen-2-ylmethylsulfamoyl)phenyl]ureido}-3-[4-(2,6-dichlorobenzoylamino)phenyl]propionic acid (S)-3-[4-(2,6-Dichlorobenzoylamino)phenyl]-2-(3-{2-[(thiophen-2-ylmethyl)sulfamoyl]phenyl}ureido)propionic acid (S)-3-[4-(2,6-Dichlorobenzoylamino)phenyl]-2-[3-(2-phenylsulfamoylphenyl)ureido]propionic acid (S)-2-[3-(2-Benzenesulfonylphenyl)-3-methylureido]-3-[4-(2,6-dichlorobenzoylamino)phenyl]propionic acid (S)-2-[3-(2-Benzylcarbamoylphenyl)ureido]-3-[4-(2,6-dichlorobenzoylamino)phenyl]propionic acid (S)-2-[3-(2-Cyclohexylcarbamoylphenyl)ureido]-3-[4-(2,6-dichlorobenzoylamino)phenyl]propionic acid (S)-3-[4-(2,6-Dichlorobenzoylamino)phenyl]-2-[3-(2-phenylcarbamoylphenyl)ureido]propionic acid (S)-2-{3-[2-(Cyclohexylmethylcarbamoyl)phenyl]ureido}-3-[4-(2,6-dichlorobenzoylamino)phenyl]propionic acid (S)-2-[3-(2-tert-Butylcarbamoylphenyl)ureido]-3-[4-(2,6-dichlorobenzoylamino)phenyl]propionic acid (S)-3-[4-(2,6-Dichlorobenzoylamino)phenyl]-2-{3-[2,4-dichloro-6-(cyclohexylmethylcarbamoyl)phenyl]ureido}propionic acid (S)-2-{3-[2-(Cyclohexylmethylcarbamoyl)-6-methylphenyl]ureido}-3-[4-(2,6-dichlorobenzoylamino)phenyl]propionic acid (S)-2-{3-[2-(Cyclohexylmethylcarbamoyl)phenyl]-3-methylureido}-3-[4-(2,6-dichlorobenzoylamino)phenyl]propionic acid methyl ester (S)-2-{3-[2-(Cyclohexylmethylcarbamoyl)phenyl]-3-methylureido}-3-[4-(2,6-dichlorobenzoylamino)phenyl]propionic acid (S)-2-[3-(2-Benzenesulfonylphenyl)ureido]-3-[4-(2,6dichlorobenzoylamino)phenyl]propionic acid methyl ester (S)-2-[3-(2-Benzenesulfonylphenyl)ureido]-3-[4-(2,6-dichlorobenzoylamino)phenyl]propionic acid (S)-3-[4-(2,6-Dichlorobenzoylamino)phenyl]-2-{3-[2-(piperidine-1-sulfonyl)phenyl]ureido}propionic acid methyl ester (S)-3-[4-(2,6-Dichlorobenzoylamino)phenyl]-2-{3-[2-(pipedine-1-sulfonyl)phenyl]ureido}propionic acid (S)-2-{3-[2-(Cyclohexylmethylsulfamoyl)phenyl]ureido}-3-[4-(2,6-dichlorobenzoylamino)phenyl]propionic acid methyl ester (S)-2-{3-[2-(Cyclohexylmethylsulfamoyl)phenyl]ureido}-3-[4-(2,6-dichlorobenzoylamino)phenyl]propionic acid (S)-2-[3-(2-Benzylphenyl)ureido]-3-[4-(2,6-dichlorobenzoylamino)phenyl]propionic acid methyl ester (S)-2-[3-(2-Benzylphenyl)ureido]-3-[4-(2,6-dichlorobenzoylamino)phenyl]propionic acid (S)-3-[4-(2,6-Dichlorobenzoylamino)phenyl]-2-[3-(2-phenylsulfanylphenyl)ureido]propionic acid methyl ester (S)-3-[4-(2,6-Dichlorobenzoylamino)phenyl]-2-[3-(2-phenylsulfanylphenyl)ureido]propionic acid (S)-2-{3-[5-Chloro-2-(4-chlorobenzenesulfonyl)phenyl]ureido}-3-[4-(2,6-dichlorobenzoylamino)phenyl]propionic acid methyl ester (S)-2-{3-[5-Chloro-2-(4-chlorobenzenesulfonyl)phenyl]ureido}-3-[4-(2,6-dichlorobenzoylamino)phenyl]propionic acid (S)-2-[3-(2-Benzenesulfonyl-5-chlorophenyl)ureido]-3-[4-(2,6-dichlorobenzoylamino)phenyl]propionic acid methyl ester (S)-2-[3-(2-Benzenesulfonyl-5-chlorophenyl)ureido]-3-[4-(2,6-dichlorobenzoylamino)phenyl]propionic acid (S)-2-{3-[2,4-Dibromo-6-(cyclohexylmethylcarbamoyl)phenyl]ureido{-3-[4-(2,6-dichlorobenzoylamino)phenyl]propionic acid methyl ester (S)-2-{3-[2,4-Dibromo-6-(cyclohexylmethylcarbamoyl)phenyl]ureido}-3-[4-(2,6-dichlorobenzoylamino)phenyl]propionic acid (S)-3-[4-(2,6-Dichlorobenzoylamino)phenyl-2-{3-[2-(toluene-4-sulfonyl)-5-trifluoromethylphenyl]ureido}propionic acid methyl ester (S)-3-[4-(2,6-Dichlorobenzoylamino)phenyl]-2-{3-[2-(toluenesulfonyl)-5-trifluoromethylphenyl]ureido}propionic acid (S)-2-{3-[2-Chloro-5-(toluene-4-sulfonyl)phenyl]ureido}-3-[4-(2,6-dichlorobenzoylamino)phenyl]propionic acid methyl ester (S)-2-{3-[2-Chloro-5-(toluene-4-sulfonyl)phenyl]ureido}-3-[4-(2,6-dichlorobenzoylamino)phenyl]propionic acid (S)-2-{3-[5-Chloro-2-(2,5-dimethoxybenzenesulfonyl)phenyl]ureido}-3-[4-(2,6-dichlorobenzoylamino)phenyl]propionic acid methyl ester (S)-2-{3-[5-Chloro-2-(2,5-dimethoxybenzenesulfonyl)phenyl]ureido}-3-[4-(2,6-dichlorobenzoylamino)phenyl]propionic acid (S)-2-[3-(2-Benzenesulfonylpyridin-3-yl)ureido]-3-[4-(2,6-dichlorobenzoylamino)phenyl]propionic acid methyl ester (S)-2-[3-(2-Benzenesulfonylpyridin-3-yl)ureido]-3-[4-(2,6-dichlorobenzoylamino)phenyl]propionic acid (S)-2-[3-(2-Benzenesulfonylphenyl)ureido]-3-(2',6'-dimethoxybiphenyl-4-yl)propionic acid methyl ester (S)-2-[3-(2-Benzenesulfonylphenyl)ureido]-3-(2',6'-dimethoxybiphenyl-4-yl)propionic acid (S)-3-{4-[(3,5-Dichloropyridine-4-carbonyl)amino]phenyl}-2-{3-[2-(piperidine-1-sulfonyl)phenyl]ureido}propionic acid methyl ester (S)-3-{4-[(3,5-Dichloropyridine-4-carbonyl)amino]phenyl}-2-(3-2-(piperidine-1-sulfonyl)phenyl]ureido}propionic acid (S)-2-{3-[5-Chloro-2-(2,5-dimethoxybenzenesulfonyl)phenyl]ureido}-3-{4-[(3,5-dichloropyridine-4-carbonyl)amino]phenyl}propionic acid methyl ester (S)-2-{3-[5-Chloro-2-(2,5-dimethoxybenzenesulfonyl)phenyl]ureido}-3-{4-[(3,5-dichloropyridine-4-carbonyl)amino]phenyl}propionic acid (S)-2-{3-[2-(Cyclohexylmethylsulfamoyl)phenyl]ureido}-3-(4-[(3,5-dichloropyridine-4-carbonyl)amino]phenyl}propionic acid methyl ester (S)-2-{3-[2-(Cyclohexylmethylsulfamoyl)phenyl]ureido}-3-4-[(3,5-dichloropyridine-4-carbonyl)amino]phenyl}propionic acid (S)-2-[3-(2-Benzenesulfonyl-5-chlorophenyl)ureido]-3-{4-[(3,5-dichloropyridine-4-carbonyl)amino]phenyl}propionic acid methyl ester (S)-2-[3-(2-Benzenesulfonyl-5-chlorophenyl)ureido]-3-{4-[(3,5-dichloropyridine-4-carbonyl)amino]phenyl}propionic acid (S)-2-[3-(2-Benzenesulfonylphenyl)ureido]-3-{4-[(3,5-dichloropyridine-4-carbonyl)amino]phenyl}propionic acid methyl ester (S)-2-[3-(2-Benzenesulfonylphenyl)ureido]-3-{4-[(3,5-dichloropyridine-4-carbonyl)amino]phenyl}propionic acid (S)-3-[4-(2,6-Dichlorobenzoylamino)phenyl]-2-{3-[2-(toluene-4-sulfonyl)pyridin-3-yl]ureido}propionic acid methyl ester (S)-3-[4-(2,6-Dichlorobenzoylamino)phenyl]-2-{3-[2-(toluene-4-sulfonyl)pyridin-3-yl]ureido}propionic acid (S)-2-{3-[2-(4-Chlorobenzenesulfonyl)pyridin-3-yl]ureido}-3-[4-(2,6-dichlorobenzoylamino)phenyl]propionic acid methyl ester (S)-2-{3-[2-(4-Chlorobenzenesulfonyl)pyridin-3-yl]ureido}-3-[4-(2,6-dichlorobenzoylamino)phenyl]propionic acid (S)-3-[4-(2,6-Dichlorobenzoylamino)phenyl]-2-{3-methyl-3-[2-(piperidine-1-sulfonyl)phenyl]ureido}propionic acid methyl ester (S)-3-[4-(2,6-Dichlorobenzoylamino)phenyl]-2-{3-methyl-3-[2-(piperidine-1-sulfonyl)phenyl]ureido}propionic acid (S)-3-(4-{[1-(3,5-Dichloropyridin-4yl)methanoyl]amino}phenyl)-2-{3-[3-(1-phenylmethanoyl)phenyl]ureido}propionic acid (S)-2-[3-(2-Benzylphenyl)-3-methylureido]-3-(4-{[1-(3,5-dichloropyridin-4-yl)methanoyl]amino}-phenyl)propionic acid methyl ester (S)-2-[3-(2-Benzylphenyl)-3-methylureido]-3-(4-{[1-(3,5-dichloropyridin-4-yl)methanoyl]amino}-phenyl)propionic acid (S)-2-{3-[2-(Cyclohexylmethylcarbamoyl)phenyl]ureido}-3-(4-{[1-(3,5-dichloropyridin-4-yl)methanoyl]amino}phenyl)propionic acid (S)-2-{3-[2-(Cyclohexylmethylcarbamoyl)phenyl]-3-methylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-propylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-cyclopropylmethylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-pentylureido}-3-(4-{[1-(3,5-dichloropyridin-4-yl)methanoyl]amino}phenyl)propionic acid (S)-2-{3-Benzyl-3-[2-(cyclohexylmethylcarbamoyl)phenyl]ureido}-3-(4-{[1-(3,5-dichloropyridin-4-yl)methanoyl]amino}phenyl)propionic acid (S)-2-{3-Cyclohexylmethyl-3-[2-(cyclohexylmethylcarbamoyl)phenyl]ureido}-3-(4-{[1-(3,5-dichloropyridin-4-yl)methanoyl]amino}phenyl)propionic acid (S)-3-(4-{[1-(3,5-Dichloropyridin-4-yl)methanoyl]amino}phenyl)-2-{3-methyl-3-[2-(piperidine-1-sulfonyl)phenyl]ureido}propionic acid methyl ester.

(S)-3-(4-{[1-(3,5-Dichloropyridin-4-yl)methanoyl]amino}phenyl)-2-{3-methyl-3-[2-(piperidine-1-sulfonyl)phenyl]ureido}propionic acid.

(S)-3-(4-{[1-(3,5-Dichloropyridin-4-yl)methanoyl]amino}phenyl)-2-{3-[2-(4-methylpiperazine-1-sulfonyl)phenyl]ureido}propionic acid methyl ester (S)-3-(4-{[1-(3,5-Dichloropyridin-4-yl)methanoyl]amino}phenyl)-2-{3-[2-(4-methylpiperazine-1-sulfonyl)phenyl]ureido}propionic acid (S)-2-[3-(2-Cyclopentanesulfonylphenyl)ureido]-3-(4-{[1-(3,5-dichloropyridin-4-yl)methanoyl]amino}phenyl)propionic acid methyl ester (S)-2-[3-(2-Cyclopentanesulfonylphenyl)ureido]-3-(4-{[1-(3,5-dichloropyridin-4-yl)methanoyl]amino}phenyl)propionic acid (S)-3-(4-{[1-(3,5-Dichloropyridin-4-yl)methanoyl]amino}phenyl)-2-{3-[2-(2-methylpropane-2-sulfonyl)phenyl]ureido}propionic acid methyl ester (S)-3-(4-{[1-(3,5-Dichloropyridin-4-yl)methanoyl]amino}phenyl)-2-{3-[2-(2-methylpropane-2-sulfonyl)phenyl]ureido}propionic acid (S)-3-(4-{[1-(3,5-Dichloropyridin-4-yl)methanoyl]amino}phenyl)-2-{3-[2-(7-methylthieno[2,3-b]pyrazin-3-ylsulfanyl)phenyl]ureido}propionic acid methyl ester (S)-3-(4-{[1-(3,5-Dichloropyridin-4-yl)methanoyl]amino}phenyl)-2-{3-[2-(7-methylthieno[2,3-b]pyrazin-3-ylsulfanyl)phenyl]ureido}propionic acid (S)-3-(4-{[1-(3,5-Dichloropyridin-4-yl)methanoyl]amino}phenyl)-2-{3-[2-(3,5-dichloropyridin-4-ylsulfanyl)phenyl]ureido}propionic acid methyl ester (S)-3-(4-{[1-(3,5-Dichloropyridin-4-yl)methanoyl]amino}phenyl)-2-{3-[2-(3,5-dichloropyridin-4-ylsulfanyl)phenyl]ureido}propionic acid (S)-3-(4-{[1-(3,5-Dichloropyridin-4-yl)methanoyl]amino}phenyl)-2-{3-[2-(piperidine-1-sulfonyl)phenyl]ureido}propionic acid methyl ester (S)-3-(4-{[1-(3,5-Dichloropyridin-4-yl)methanoyl]amino}phenyl)-2-{3-[2-(piperidine-1-sulfonyl)phenyl]ureido}propionic acid (S)-3-(4-{[1-(3,5-Dichloropyridin-4-yl)methanoyl]amino}phenyl)2-{3-methyl-3-[2-(piperazine-1-sulfonyl)phenyl]ureido}propionic acid methyl ester (S)-3-(4-{[1-(3,5-Dichloropyridin-4-yl)methanoyl]amino}phenyl)-2-{3-methyl-3-[2-(piperazine-1-sulfonyl)phenyl]ureido}propionic acid (S)-2-[-(2-Benzenesulfonylphenyl)ureido]-3-(4-{[1-(2-chloro-6-methylpyridin-3-yl)methanoyl]amino}phenyl)propionic acid (S)-2-[3-(2-Benzenesulfonylphenyl)ureido]-3-(4-{[1-(2,6-dichloropyridin-3-yl)-methanoyl]amino}phenyl)propionic acid (S)-2-[3-(2-Benzenesulfonylphenyl)ureido]-3-(4-{[1-(3,5-dimethoxypyridin-4-yl)-methanoyl]amino}phenyl)propionic acid (S)-2-[3-(2-Benzenesulfonylphenyl)ureido]-3-(4-{[1-(3,5-dibromopyridin-4-yl)-methanoyl]amino}phenyl)propionic acid (S)-2-[3-(2-Benzenesulfonylphenyl)ureido]-3-[4-(2,6-dichlorobenzylamino)phenyl]propionic acid methyl ester (S)-2-[3-(2-Benzenesulfonylphenyl)ureido]-3-[4-(2,6-dichlorobenzylamino)phenyl]propionic acid (S)-2-[3-(2-Benzenesulfonylphenyl)ureido]-3-{4-[(3,5-dichloropyridin-4-ylmethyl)amino]phenyl}propionic acid methyl ester (S)-2-[3-(2-Benzenesulfonylphenyl)ureido]-3-{4-[(3,5-dichloropyridin-4-ylmethyl)amino]phenyl}propionic acid (S)-2-[3-(2-Benzenesulfonylphenyl)ureido]-3-(4-dimethylcarbamoyloxyphenyl) propionic acid methyl ester (S)-2-[3-(2-Benzenesulfonylphenyl)ureido]-3-(4-dimethylcarbamoyloxyphenyl) propionic acid 4-Methylpiperazine-1-carboxylic acid 4-{(S)-2-[3-(2-benzenesulfonylphenyl) ureido]-2-methoxycarbonylethyl}phenyl ester 4-Methylpiperazine-1-carboxylic acid 4-{(S)-2-[3-(2-benzenesulfonylphenyl)ureido]-2-carboxyethyl}phenyl ester 3,5-Dichloroisonicotinic acid 4-{(S)-2-[3-(2-benzenesulfonylphenyl)ureido]-2-methoxycarbonylethyl}phenyl ester 3,5-Dichloroisonicotinic acid 4-{(S)-2-[3-(2-benzenesulfonylphenyl)ureido]-2-carboxyethyl}phenyl ester (S)-3-(2'-Cyanobiphenyl-4-yl)-2-{3-[2-(piperidine-1-sulfonyl)phenyl]ureido}propionic acid methyl ester (S)-3-(2'-Cyanobiphenyl-4-yl)-2-{3-[2-(piperidine-1-sulfonyl)phenyl]ureido}propionic acid (S)-3-(2'-Methoxybiphenyl-4-yl)-2-{3-[2-(piperidine-1-sulfonyl)phenyl]ureido}propionic acid methyl ester (S)-3-(2'-Methoxybiphenyl-4-yl)-2-{3-[2-(piperidine-1-sulfonyl)phenyl]ureido}propionic acid (S)-2-[3-(2-Benzenesulfonylphenyl)ureido]-3-[4-([2,6]naphthyridin-1-ylamino)phenyl]propionic acid methyl ester (S)-2-[3-(2-Benzenesulfonylphenyl)ureido]-3-[4-([2,6]naphthyridin-1-ylamino)phenyl]propionic acid (S)-3-[4-([2,6]Naphthyridin-1-ylamino)phenyl]-2-{3-[2-(piperidine-1-sulfonyl)phenyl]ureido}propionic acid methyl ester (S)-3-[4-([2,6]Naphthyridin-1-ylamino)phenyl]-2-{3-[2-(piperidine-1-sulfonyl)phenyl]ureido}propionic acid (S-2-[3-(2-Benzylphenyl)-3-methylureido]-3-[4-([2,6]naphthyridin-1-ylamino)phenyl]propionic acid methyl ester (S)-2-[3-(2-Benzylphenyl)-3-methylureido]-3-[4-([2,6]naphthyridin-1-ylamino)phenyl]propionic acid (S)-2-[3-(2-Benzenesulfonylphenyl)ureido]-3-[4-([2,7]naphthyridin-1-ylamino)phenyl]propionic acid methyl ester (S)-2-[3-(2-Benzenesulfonylphenyl)ureido]-3-[4-([2,7]naphthyridin-1-ylamino)phenyl]propionic acid (S)-3-[4-([2,7]Naphthyridin-1-ylamino)-phenyl]-2-{3-[2-(piperidine-1-sulfonyl)phenyl]ureido}propionic acid methyl ester (S)-3-[4-([2,7]Naphthyridin-1-ylamino)-phenyl]-2-{3-[2-(piperidine-1-sulfonyl)phenyl]ureido}propionic acid (S)-2-[3-(2-Benzylphenyl)-3-methylureido]-3-[4-([2,7]naphthyridin-1-ylamino)phenyl]propionic acid methyl ester (S)-2-[3-(2-Benzylphenyl)-3-methylureido]-3-[4-([2,7]naphthyridin-1-ylamino)phenyl]propionic acid (S)-2-[3-(2-Benzenesulfonylphenyl)ureido]-3-[4-([2,6]naphthyridin-1-yloxy)phenyl]propionic acid methyl ester (S)-2-[3-(2-Benzenesulfonylphenyl)ureido]-3-[4-([2,6]naphthyridin-1-yloxy)phenyl]propionic acid (S)-3-[4-([2,6]Naphthyridin-1-yloxy)phenyl]-2-{3-[2-(piperidine-1-sulfonyl)phenyl]ureido}propionic acid methyl ester (S)-3-[4-([2,6]Naphthyridin-1-yloxy)phenyl]-2-{3-[2-(piperidine-1-sulfonyl)phenyl]ureido}propionic acid (S)-2-[3-(2-Benzenesulfonylphenyl)ureido]-3-[4-([2,7]naphthyridin-1-yloxy)phenyl]propionic acid methyl ester (S)-2-[3-(2-Benzenesulfonylphenyl)ureido]-3-[4-([2,7]naphthyridin-1-yloxy)phenyl]propionic acid (S)-3-[4-([2,7]Naphthyridin-1-yloxy)phenyl]-2-{3-[2-(piperidine-1-sulfonyl)phenyl]ureido}propionic acid methyl ester (S)-3-[4-([2,7]Naphthyridin-1-yloxy)phenyl]-2-{3-[2-(piperidine-1-sulfonyl)phenyl]ureido}propionic acid (S)-2-[3-(2-Benzylphenyl)-3-methylureido]-3-[4-([2,7]naphthyridin-1-yloxy)phenyl]propionic acid methyl ester (S)-2-[3-(2-Benzylphenyl)-3-methylureido]-3-[4-([2,7]naphthyridin-1-yloxy)phenyl]propionic acid (S)-2-[3-(2-Benzylphenyl)-3-methylthioureido]-3-(4-{[1-(3,5-dichloropyridin-4-yl)methanoyl]amino}phenyl)propionic acid methyl ester (S)-2-[3-(2-Benzylphenyl)-3-methylthioureido]-3-(4-{[1-(3,5-dichloropyridin-4-yl)methanoyl]amino}phenyl)propionic acid (S)-2-3-[2-(Cyclohexylmethylcarbamoyl)phenyl]-3-methylthioureido)3-(4-{[1-(3,5-dichloropyridin-4-yl)methanoyl]amino}phenyl)propionic acid methyl ester (S)-2-(3-[2-(Cyclohexylmethylcarbamoyl)phenyl]-3-methylthioureido)-3-(4-{[1-(3,5-dichloropyridin-4-yl)methanoyl]amino}phenyl)propionic acid (S)-3-(4-{[1-(3,5-Dichloropyridin-4-yl)methanoyl]amino}phenyl)-2-{3-[2-(piperidine-1-sulfonyl)phenyl]thioureido}propionic acid and pharmaceutically acceptable salts thereof.

In one embodiment of the invention, R1, R2, R3, R4, R5, L1, L2, W, X, Y, Z, Ra, Rb, Rc, Rd, Re, n and m are as defined above, with the proviso that either.

A) i) when Y is a 2,5 disubstituted aryl, then L2 is not a covalent bond, —O— —N(Rc)—, —(O)CO— or —OC(O)—; and ii) when Y is a 2,5 disubstituted aryl and L2 is —C(O)—, R5 may not be $C_{1-6}$ alkyl, cycloalkyl or cycloalkyl-$C_{1-4}$ alkyl; or B) Z is a group —C(O)O Rd, wherein Rd is as defined above; or C) when Y is substituted by one or more substituents other than L1-R1, said substituent(s), which may be the same or different, are selected from Ra; or D) when Y is phenyl or pyridyl, the moiety R1-L1 is other than alkyl, and —$CO_2R$ wherein R is a straight, branched or cyclic alkyl of from 1 to 7 carbon atoms.

Preferably, in proviso A above, when Y is a 2,5 disubstituted aryl, then L2 is not a covalent bond, —O—, —N(Rc)—, —(O)CO—, —OC(O)— or —C(O)—. The most preferred groups L2 in proviso A above, when Y is a 2,5 disubstituted aryl, are —N(Rc)CO— and —OC(O)N(Rc)—, wherein Rc is preferably hydrogen or $C_{1-4}$ alkyl, most preferably hydrogen. Most preferred compounds according to proviso A are those wherein Y is not a 2,5-disubstituted aryl. It is also preferred according to proviso A that Y either carries two groups Rb, one group Rb which is in the 3, 4 or 6-position, or that Y does not carry any Rb substituents.

In proviso B above, Z is preferably represented by —C(O)OH or —C(O)OMe.

In proviso C above, the substituent(s) on the group Y other than the substituent -L1-R1 are preferably a halogen or a group —ORe, —OH or —$CF_3$, in particular a chlorine, bromine or —OMe group.

Compounds according to proviso (D) are, for example, useful in the treatment and prevention of inflammatory bowel disease.

In this embodiment, the compounds of the invention may fulfill some or all of the requirements A to D above. Thus, in this embodiment the compounds of the invention can have requirements A and B, A and C, A and D, B and C, B and D, C and D, A, B and C, A, B and D, C, B and D or A, B, C and D.

The present invention also provides processes for preparing a compound of the invention. Thus a compound of Formula I in which Z is a —COOH group may be obtained by hydrolysis of an ester of formula (II):

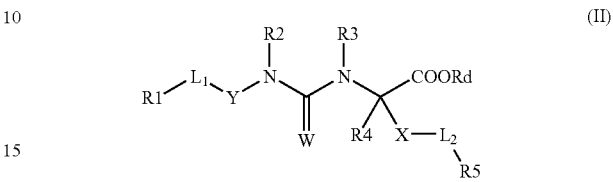

(II)

where Rd is defined as above with the exception the Rd is not hydrogen.

The hydrolysis may be performed using either an acid or a base depending on the nature of Rd, for example a base such as lithium, sodium or potassium hydroxide in an aqueous organic solvent mixture such as methanol, ethanol, tetrahydrofuran, diethyl ether, dioxane at a temperature of from 20° C. to 100° C. In the case of acid hydrolysis in an acid such as trifluoroacetic acid the reaction is performed at room temperature.

Esters of formula (II), wherein R2 and R3 are H, may be prepared by reaction of the corresponding amine of formula (III):

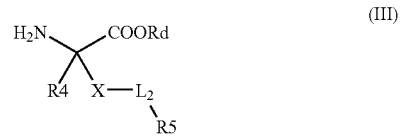

(III)

or a salt thereof with a corresponding isocyanate wherein W is O or isothiocyanate wherein W is S of formula (IV):

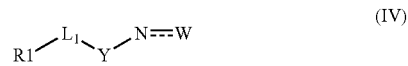

(IV)

The reaction may be carried out under standard conditions for this type of reaction. The reaction is preferably performed in an inert organic solvent such as dichloromethane, acetonitrile, toluene, dioxane, tetrahydrofuran, diethyl ether at a temperature of from room temperature to 50° C.

When the isocyanate or isothiocyanate of formula (IV) is not commercially available, these compounds could be prepared by standard conditions treating the corresponding amine (V):

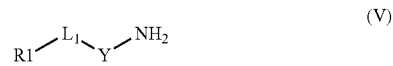

(V)

with triphosgene, diphosgene, phosgene or thiophosgene, in the presence of a base such as triethylamine, diisopropylethylamine, sodium bicarbonate e.g. in an inert organic solvent such as dichloromethane, tetrahydrofuran, dioxane, diethyl ether, e.g. or an aqueous mixture of an halogenated solvent such as chloroform, e.g. at a temperature of from 0° C. to 80° C.

Esters of formula (II) wherein R2 is as described above and R3 is an H, may be prepared by reaction of the corresponding amine (VI):

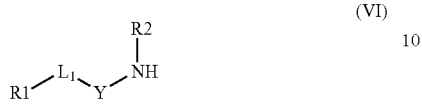

with isocyanates wherein W is O or isothiocyanates wherein W is S of formula (VII):

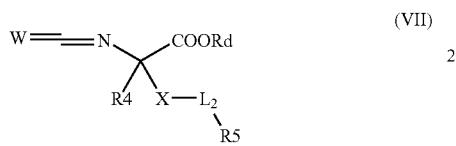

The reaction between the amine (VI) and the isocyanate or isothiocyanate (VII) may be carried out in an inert organic solvent such as dichloromethane, acetonitrile, dioxane, tetrahydrofuran, toluene, e.g. at a temperature of from room temperature to 130° C.

The isocyanate or isothiocyanate of formula (VII) may be obtained by reacting a corresponding amine (III) with triphosgene, diphosgene or phosgene in the presence of a base such as triethylamine, diisopropylethyl amine, DBU, e. g. in an inert organic solvent such as dichloromethane, tetrahydrofuran, dioxane at a temperature of from 0° C. to room temperature. Alternatively the isothiocyanate may be prepared by reacting a corresponding amine (III) with thiophosgene in the presence of a base such as sodium bicarbonate, triethylamine, e.g. in an aqueous mixture of solvents such as chloroform, dioxane, tetrahydrofuran, e.g. at a temperature of from 0° C. to room temperature.

Alternatively, esters of formula (II) wherein R2 and R3 are as described above, may be prepared by reaction of the corresponding amine (VII):

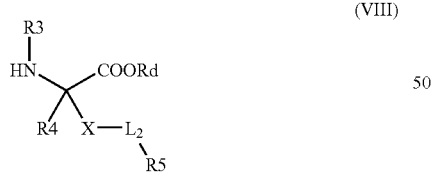

with the corresponding amine (VI) in the presence of triphosgene, diphosgene, thiophosgene or carbonyl diimidazole and a base such as triethylamine, diisopropylethylamine, DBU, sodium bicarbonate e.g. using an inert organic solvent such as dichloromethane, tetrahydrofuran, dioxane, diethyl ether, toluene, e.g. at a temperature of from 0° C. to 100° C.

Additionally, an amine of formula (VI) can also be derivatized to form a urea by reaction of amine (VI) with 4-nitrophenyl chloroformate in an inert solvent, such as dichloromethane, at a temperature of from −25° C. to about 0° C. Treatment of the resulting carbamate with an excess of a base, such as triethylamine, followed by addition of amine (VII) provides the corresponding ester of formula (II).

Alternatively, in another method for preparing ureas, an amine of formula (VIII) is added to a carbamyl chloride (IX):

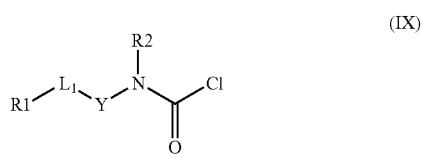

in an inert organic solvent, such as dichloromethane, acetonitrile, tetrahydofuran, e.g. at a temperature of from room temperature to 70° C.

Carbamyl chlorides of formula (IX) may be obtained by reacting the corresponding amine (VI), wherein R2 is other than H, with triphosgene, diphosgene or phosgene in the presence of a base such as triethylamine, diisopropylethylamine, DBU, e. g. in an inert organic solvent such as dichloromethane, tetrahydrofuran or dioxane at a temperature of from 0° C. to 80° C.

Amines of formula (VI) and (VIII), wherein R2 and R3 are different from H, could be prepared from the corresponding amines of formula (V) and (III) respectively by alkylation using the corresponding halide, sulphonate, sulphate derivative, e.g. preferably in an inert organic solvent such as toluene, dioxane, tetrahydrofuran, acetone, methyl isobutyl ketone, dimethylformamide, e.g. and in the presence of a base such as triethylamine, diisopropylethylamine, DBU, potassium carbonate, sodium hydroxide, cesium hydroxide, e.g. at a temperature of from room temperature to 130° C. Alternatively, a reductive alkylation process could be used employing the corresponding aldehyde and a borohydride, for example sodium triacetoxyborohydride or sodium cyanoborohydride, in a solvent such as dichloromethane, acetone; ethanol, methanol, trimethylorthoformate, in the presence of an acid, where necessary, such as acetic acid at a temperature of from room temperature to 80° C.

Amines of formula (V) that are not commercially available could be obtained by reduction of the corresponding nitro derivative of formula (X):

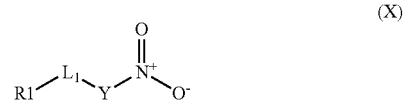

for example by catalytic hydrogenation using hydrogen in the presence of a metal catalyst, for example palladium on charcoal, Raney-Ni® in a solvent such as methanol, ethanol, ethyl acetate, tetrahydrofuran, e.g. or by chemical reduction using a metal such as, tin, iron, zinc, in the presence, in some cases, of an acid such as hydrochloric acid, ammonium chloride, e.g.

The nitro derivatives of formula (X) are either commercially available or known compounds or may be prepared from known starting materials by use of analogous processes to those used for the preparation of the known compounds.

Thus in an Example, a compound of formula (XI):

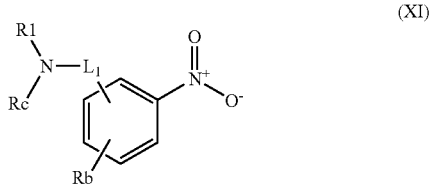

(XI)

wherein Xa is —CO— or —SO2—, can be prepared:

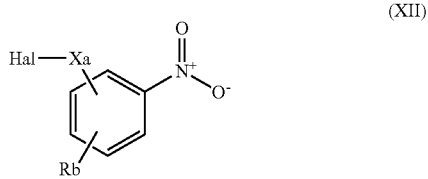

(XII)

by reaction of the corresponding haloderivabve (XII) with the corresponding amine of formula (XIII):

(XIII)

wherein R1 and Rc are as defined above.

This reaction may be carried out by standard conditions for these type of reactions. The reaction is preferably performed in an inert organic solvent such as dichloromethane, pyridine, tetrahydrofuran, in the presence of a base such as triethylamine, diisopropylethylamine, DBU, pyridine, potassium carbonate, sodium hydroxide, e.g., at a temperature of from 0° C. to 50° C.

Alternatively, compounds of Formula I in which Z is a —C(O)NH2 group may be obtained by standard conditions. By way of illustration, an ester of formula (II) can be treated with saturated solution of ammonia in methanol, ethanol or dioxane, e.g. at room temperature to provide the corresponding primary amide.

Additionally, compounds of Formula I or an intermediate thereof in which Z is a tetrazole group may be obtained by standard conditions treating the corresponding nitrile derivative of formula (XIV):

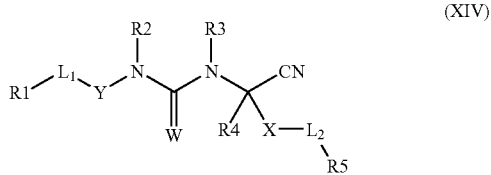

(XIV)

with sodium azide or tributyltinazide in an inert organic solvent such as dimethylformamide, toluene, xylene, tetrahydrofuran, e.g. in the presence, in some cases, of an acid such as ammonium chloride, e.g. at a temperature of from room temperature to 140° C.

Nitriles of formula (XIV) may be prepared from the corresponding primary amide by methods known per se, e.g. Z. Groznka, et al. *Roczniki Chemii Ann. Soc. Chim. Polonorum* (1971), 45, 967.

Compounds of Formula I in which Z is a —C(O)N(Re)SO2Rd group, wherein Rd and Re are as defined above, can be prepared by coupling a carboxylic acid of Fomula I, wherein Rd is H, with an sulfonamide derivative of formula (XV):

(XV)

wherein Rd and Re are as defined above, under conventional coupling conditions.

This coupling reaction is typically conducted using well-known coupling reagents such as carbodiimides, BOP reagent (benzotriazol-1-yloxytris(dimethylamino)phosphonium hexafluorophosphonate) and the like. Suitable carbodiimides include, by way of example, dicyclohexilcarbodiimide (DCC), 1-(3-dimethylaminopropyl)-3-ethylcarbodiimide (EDC) and the like. Additionally, well known coupling promoters, such as N-hydroxysuccinimide, 1-hydroxybenzotriazole and the like, may be used to facilitate the coupling reaction. This reaction is typically conducted by reacting an acid of Formula I, wherein Rd is H, with the coupling reagent and the sulfonamide of formula (XV) in an inert organic solvent such as dichloromethane, chloroform, acetonitrile, tetrahydrofuran, dimethylformamide, e.g. in the presence of a base such as triethylamine, diisopropylethylamine, e.g. at temperature of from 0° C. to room temperature.

Alternatively, acids of Formula I, wherein Rd is H, can be converted into an acid halides using methods known per se, which is then coupled with a sulfonamide derivative of formula (XV). This reaction is conducted in the presence of a suitable base, by way of example, triethylamine, diisopropylethylamine, N-methylmorpholine, sodium hydride, sodium hydroxide in a solvent such as dichloromethane, tetrahydrofuran, dioxane, water, at temperature of from 0° C. to 100° C.

Compounds of formula I in which Z is a —C(O)Rd group, wherein Rd is as defined above, may be prepared by reacting a Weinreb type amide of formula (XVI):

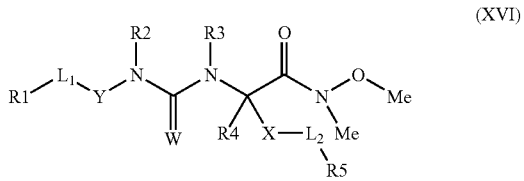

(XVI)

with an organometallic agent such as a Grignard reagent or an organolithium reagent of formula RdMgX or RdLi respectively where Rd is as defined above. Suitable solvents for the reaction are aprotic organic solvents such as diethyl ether, tetrahydrofuran, e.g. and at a temperature of from −78° C. to room temperature. The Grignard reagent and the organolithium reagent are either commercially available or they can be prepared by methods well known in the art. For example, RdLi can be prepared by treating an organic halide of formula RdX where X is an halo group with an organic base such as butyllithium.

Weinreb type amides (XVI) can be prepared by coupling the corresponding acid of formula I, wherein Rd is H, with N-methoxy-N-methylamine by methods of coupling known per se.

Compounds of formula I in which W is a NCN group may be prepared from the corresponding thiourea of formula (XVII):

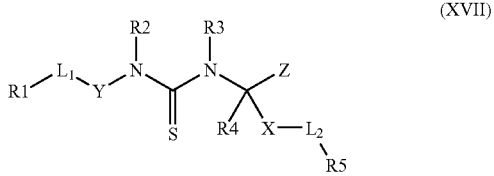

by reaction with CNNH2 in the presence of coupling agents such as carbodiimides. Suitable carbodiimides include, by way of example, dicyclohexilcarbodiimide (DCC), 1-(3-dimethylaminopropyl)-3-ethylcarbodiimide (EDC) and the like. The reaction is carried out in an inert organic solvent, such as dichloromethane, chloroform, acetonitrile, tetrahydrofuran, dimethylformamide, e.g. in the presence of a base such as triethylamine, diisopropylethylamine, e.g. at temperature of from 0° C. to room temperature.

Additionally, compounds of Formula I in which W is a N(Rc) group, wherein Rc is as described above, may be prepared from the corresponding carbodiimide of formula (XVIII):

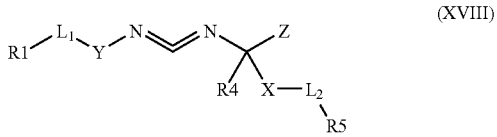

and an amine of formula NH(Rc), wherein Rc is as defined above, using methods known per se, e.g. N. Yamamoto, et al. *Chem. Lett.* (1994), 12, 2299.

Carbodiimides of formula (XVIII) can be prepared from the corresponding urea or thiourea derivatives by methods known per se, e.g: R. Appel, et al. *Chem. Ber.* (1971), 104, 1335.

A compound of Formula I in which R2 and R3 form a ring may be prepared by reacting the corresponding urea of Formula I, wherein R2 and R3 are H, with a double alkylating agent such as 1,2-dibromoethane, 1,3-dibromopropane, e.g. The reaction is preferably performed in an inert organic solvent such as tetrahydrofuran, dimethylformamide, dioxane, e.g. in the presence of a base such as sodium hydride, e.g. at a temperature of from room temperature to 100° C.

Intermediates of formula (III) are known compounds or may be prepared from known starting materials by methods well known in the literature (WO 98/58902, WO 99/10312, WO 99/10313, WO 99/36393, WO 00/43372).

In any of the heregoing general description of the synthesis of compounds of Formula I, intermediate compounds at any stage may contain protecting groups to protect functionalities which would otherwise react under the conditions described. Such protecting groups are added and removed at appropriate stages during the synthesis of compounds of Formula I and the chemistries of such protections and deprotections are well described in the prior art (for example: T. W. Green and P. G. M. Wuts, "Protecting Groups in Organic Synthesis"; John Wiley and Sons, Inc.; Third Edition, 1999).

Where it is desired to obtain a particular enantiomer of a compound of Formula I this may be produced from the corresponding mixture of enantiomers using a suitable conventional procedure for resolving enantiomers. Thus for example, diastereomeric derivatives, e.g. salts, may be produced by reaction of a mixture of enantiomers of Formula I e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt. In another resolution process a racemate of Formula I may be separated using chiral High Performance Liquid Chromatography.

Alternatively, if desired, a particular enantiomer may be obtained by using an appropiate chiral intermediate in one of the processes described above.

The compounds of Formula I can be converted by methods known per se into pharmaceutically acceptable salts, preferably acid addition salts by treatment with organic or inorganic acids such as fumaric, tartaric, citric, succinic or hydrochloric acid. Also compounds of Formula I in which there is the presence of an acidic group may be converted into pharmacologically acceptable salts by reaction with an alkali metal hydroxide such as sodium or potassium hydroxide or an organic base. The acid or alkali addition salts so formed may be interchanged with suitable pharmaceutically acceptable counterions using processes known per se.

Pharmacological Action

The present invention also provides a method for treating a subject afflicted with a pathological condition susceptible to amelioration by antagonism of α4β1 and/or α4β7 integrins, which comprises administering to the subject an effective amount of a compound of the invention, or a pharmaceutically acceptable salt thereof, as well as the use of a compound of the invention in the manufacture of a medicament for the treatment of a pathological condition susceptible of being improved or prevented by antagonism of α4β1 and/or α4β7 integrins.

Those of skill in the art are well aware of the pathological conditions susceptible to amerlioration by antagonism of α4β1 and/or α4β7 integrins. Such conditions include, for example, conditions susceptible to amelioration by administration of a known anti-α4 antibody. The compounds of the invention can therefore be used to ameliorate any pathological condition susceptible to amelioration by an anti-α4 antibody.

The following assays demonstrate the activity of the compounds.

U-937 Cell Adhesion to Human VCAM-1 (α4β1 Binding Assay)

Recombinant human soluble VCAM-1 (R&D Systems Ltd., UK) at 2 μg/ml in PBS was immobilized overnight onto microtiter plates. Unbound VCAM-1 was washed away and VCAM-1 coated plates were blocked with bovine serum albumin (BSA) 2,5% in PBS for 2 h at room temperature. U-937 cells were labelled with 5-carboxyfluorescein diacetate (5-CFDA) in order to detect bound cells to the wells. Test compounds were added to the wells followed by U-937 cells and the adhesion assay was performed for 1 h at 37° C. Following incubation, the wells were emptied and washed. Inhibition of binding was measured by the quantity of fluorescence bound to the plate for each of the various concentrations of test compound, as well as for controls containing no test compound, with a Cytofluor 2300 fluorescence measurement system.

RPMI 8866 Cell Adhesion to Mouse MAdCAM-1 ($\alpha 4\beta 7$ Binding Assay)

Recombinant mouse MAdCAM-1 was coated on a 96-well plate overnight. Unbound MAdCAM-1 was washed away and plates were blocked with 0,5% BSA. Cells were labelled with BCECF-AM and added to ligand-coated wells. Test compounds were added to the wells followed by RPMI 8866 and the adhesion assay was performed for 45 min at room temperature. Following incubation, the wells were emptied and washed. Inhibition of binding was measured by the quantity of fluorescence bound to the plate for each of the various concentrations of test compound, as well as for controls containing no test compound, with a Cytofluor 2300 fluorescence measurement system.

Compounds of the invention generally have $IC_{50}$ values in the $\alpha 4\beta 1$ and $\alpha 4\beta 7$ assays below 10 µM. The compounds of the Examples typically had $IC_{50}$ values of 1 µM and below. Most preferred compounds of the current invention displayed $IC_{50}$ values of below 100 nM in one or both of the adhesion assays.

The following Examples have $IC_{50}$ values in the $\alpha 4\beta 1$ assays between 1 µM and 100 nM: 6, 8, 14, 19, 24, 25, 26, 27, 28, 29, 30, 34, 46, 50, 52, 56, 60, 100, 104, 108, 112, 114, 118, 120, 126, 132, 138, 142.

The following Examples have $IC_{50}$ values in the $\alpha 4\beta 1$ assays below 100 nM: 2, 20, 21, 22, 23, 32, 36, 38, 40, 42, 44, 48, 54, 58, 62, 64, 66, 68, 70, 72, 74, 76, 77, 79, 80, 81, 82, 83, 84, 85, 86, 88, 90, 92, 94, 96, 98, 102, 103, 105, 106, 110, 116, 122, 124, 128, 130, 134, 136, 140, 144, 146, 147.

The following Examples have $IC_{50}$ values in the $\alpha 4\beta 7$ assays between 10 µM and 1 µM: 23, 38, 40, 74, 76, 114.

The following Examples have $IC_{50}$ values in the $\alpha 4\beta 7$ assays between 1 µM and 100 nM: 62, 64, 66, 68, 70, 88, 106.

The following Examples have $IC_{50}$ values in the $\alpha 4\beta 7$ below 100 nM: 82, 83, 90.

The ability of the compounds of Formula I to antagonize the actions of $\alpha 4\beta 1$ and/or $\alpha 4\beta 7$ integrins make them useful for inhibiting cell (e.g. leukocyte) adhesion processes, including cell activation, migration, proliferation and differentiation, thus preventing or reversing the symptoms of immune or inflammatory disorders and of other pathological conditions known to be mediated by the binding of $\alpha 4\beta 1$ and/or $\alpha 4\beta 7$ to their various respective ligands. The subject in need of treatment is typically a mammal, in particular a human.

Preferably, said pathological condition, disease or disorder is selected from multiple sclerosis, asthma, allergic rhinitis, allergic conjunctivitis, inflammatory lung diseases, rheumatoid arthritis, polydermatomyositis, septic arthritis, type I diabetes, organ transplantation rejection, restenosis, autologous bone marrow transplantabon, inflammatory sequelae of viral infections, atopic dermatitis, myocarditis, inflammatory bowel disease including ulcerative colitis and Chron's disease, certain types of toxic and immune-based nephritis, contact dermal hypersensitivity, psoriasis, tumor metastasis, atherosclerosis and cerebral ischemia.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per Kg, and most preferably 0.1 to 10 mg per kg, in single or divided doses. On the other hand, it may be necessary to use dosages outside these limits in some cases.

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Another aspect of the present invention provides pharmaceutical compositions comprising a a compound of the invention, or a pharmaceutically acceptable salt thereof. Accordingly, the method of treatment or use of the present invention may also involve pharmaceutical compositions which comprise any compound of the invention, or a pharmaceutically acceptable salt thereof.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients. Accordingly, the pharmaceutical compositions of the present invention encompass any composition made by admixing a compound of the invention additional active ingredient(s), and pharmaceutically acceptable excipients.

The expression "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (opthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dose unit form in which case solid pharmaceutical carriers are obviously employed. If desired, tablets may be coated by standard aqueous or nonaqueous techniques.

Compositions for parenteral injection may be prepared from soluble salts, which may be or may not be freeze-dried and which may be dissolved in pyrogen free aqueous media or other appropriate parenteral injection fluid.

For administration by inhalation, the compounds of the present invention are conveniently delivered in the form of an aerosol spray presentation from pressurized packs of nebulisers. The compounds may also be delivered as powders, which may be formulated and the powder composition may be inhaled with the aid of an insufflation powder inhaler device. The preferred delivery systems for inhalation are metered dose inhalation (MDI) aerosol, which may be formulated as a suspension or solution of compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of the invention include transdermal devices, aerosols, creams, ointments, lotions, dusting powders, and the like.

EXAMPLES

The syntheses of the compounds of the invention and of the intermediates for use therein are illustrated by the following Examples, including Preparation Examples (Preparations 1–28), which do not limit the scope of the invention in any way.

$^1$H Nuclear Magnetic Resonance Spectra were recorded on a Varian Gemini-2000 (300 MHz) spectrometer. Low Resolution Mass Spectra (m/z) were recorded on a Micromass ZMD mass spectrometer using ESI. Melting points were recorded using a Perkin Elmer DSC-7 apparatus. The chromatographic separations were obtained using a Waters 2690 system equipped with a Symmetry C18 (2.1×10 mm, 3.5 mM) column. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

Preparation 1

(S)-3-[4-(2,6-Dichlorobenzoylamino)phenyl]-2-isocyanatepropionic acid methyl ester To a stirred solution of triphosgene (0.24 g, 0.83 mmol) in dichloromethane (10 ml) at 0° C. was slowly added a solution of (S)-2-amino-3-[4-(2,6-dichlorobenzoylamino)-phenyl]propionic acid methyl ester hydrochloride (1 g, 2.43 mmol) and triethylamine (0.24 g, 2.43 mmol). The resulting mixture was stirred at 0° C. for 15 min. Then, triethylamine (0.49 g, 4.86 mmol) was added at 0° C. and the reaction mixture was stirred at 0° C. for an additional 30 min. After 3 h stirring at room temperature, the solvent was removed under reduced pressure without external heating. The resulting crude was treated with ethyl acetate and the solid was filtered off. The filtrated solvent was removed under reduced pressure and the resulting crude oil (0.9 g, 90%) was used in the next reaction without further purification.

Preparation 2

2-Amino-N-cyclohexyl-N-methylbenzenesulfonamide

To a stirred solution of cyclohexylmethylamine (0.57 g, 5 mmol) in pyridine (8 ml) was added slowly at 0° C. 2-nitrobenzenesulfonyl chloride (1.10 g, 5 mmol) and the reaction mixture was allowed to warm to room temperature and stirred overnight. The pyridine was removed under reduced pressure and the crude mixture obtained was diluted with ethyl acetate and washed with hydrochloric acid solution (25 ml), water (25 ml), brine (25 ml) and dried over sodium sulphate. The solvent was removed under reduced pressure and the resulting crude oil (1.40 g) was dissolved in ethanol and hydrogenated in the presence of a catalytic amount of Raney-Ni®. The catalyst was removed by filtration through Celite® and the solvent was eliminated under reduced pressure to yield a yellow solid (0.80 g, 60%).

δ (DMSO-d6): 7.45 (d, 1H), 7.26 (t, 1H), 6.82 (d, 1H), 6.60 (t, 1H), 3.64 (m, 1H), 2.68 (s, 3H), 1.70 (m, 2H), 1.38 (m, 8H).

Preparation 3

2-(Piperidine-1-sulfonyl)phenylamine

The title compound (0.59 g, 58%) was obtained as a brown solid from piperidine and 2-nitrobenzenesulfonyl-chloride following the same procedure as described in preparation 2.

δ (DMSO-d6): 7.40 (d, 1H), 7.35 (t, 1H), 6.82 (d, 1H), 6.64 (t, 1H), 2.90 (m, 4H), 1.43 (m, 6H).

Preparation 4

Methyl[2-(piperidine-1-sulfonyl)phenyl]amine

A mixture of compound from preparation 3 (0.5 g, 2.08 mmol), dimethyl sulphate (0.31 g, 2.49 mmol) and potassium carbonate (4.16 g, 4.16 mmol) in acetone (4 ml) was heated under reflux overnight. The solvent was removed under reduced pressure and the crude mixture was partitioned between water and ethyl acetate. The organic layer was dried over sodium sulphate and the solvents removed under reduced pressure. The crude was purified by flash chromatography (hexanes:ethyl acetate, 1:1) to yield the title compound (0.26 g, 50%) as a yellow solid.

δ (DMSO-d6): 7.42 (d, 2H), 6.75 (m, 2H), 6.26 (m, 1H), 3.05 (m, 4H), 2.81 (d, 3H), 1.50 (m, 6H).

Preparation 5

(2-Benzenesulfonylphenyl)methylamine

The title compound (0.07 g, 32%) was obtained as a yellow solid from 2-benzenesulfonylphenylamine following the same procedure as described in preparation 4.

δ (DMSO-d6): 7.98 (d, 2H), 7.80 (d, 1H), 7.65 (m, 3H), 7.42 (t, 1H), 6.75 (m, 2H), 6.34 (m, 1H), 2.80 (d, 3H).

Preparation 6

2-Amino-N-cyclohexyl-N-methylbenzamide

A solution of 2-nitrobenzoyl chloride (1.0 g, 5.4 mmol) in dichloromethane (1 ml) was added dropwise to a stirred solution of cyclohexylmethylamine (0.068 g, 6 mmol), triethylamine (1.12 ml, 8 mmol) and a catalytic amount of 4-dimethylaminopyridine in dichloromethane (4 ml) at 0° C.

After 1 h at 0° C., the reaction mixture was allowed to warm to room temperature and stirred overnight. The reaction mixture was diluted with dichloromethane and washed with hydrochloric acid 1N (10 ml), sodium hydroxide 2N (10 ml) and brine (10 ml). The organic layer was dried (MgSO$_4$) and concentrated under reduced pressure to yield N-cyclohexyl-N-methyl-2-nitrobenzamide (1.05 g, 74%) that was used in the next step without further purification.

A solution of the crude N-cyclohexyl-N-methyl-2-nitrobenzamide (1.05 g, 4 mmol) and a catalytic amount of Raney-Ni® in methanol (25 ml) was stirred overnight under hydrogen at room temperature. The catalyst was removed by filtration and the filtrate was concentrated under reduced pressure. The resulting crude was dissolved in dichloromethane and washed with saturated aqueous sodium bicarbonate. The organic layer was dried (MgSO$_4$) and the solvents removed under reduced pressure to give (0.89 g, 96%) of the title compound as a white solid.

δ(CDCl3): 7.11 (m, 2H), 6.64 (m, 2H), 2.89 (s, 3H), 1.80–0.90 (m, 11H).

Preparation 7

N-Cyclohexyl-N-methyl-2-methylaminobenzamide

A mixture of N-cyclohexyl-N-methylamine (0.17 g, 0.62 mmol) and 1-methyl-1H-benzo[d][1,3]oxazine-2,4-dione (0.25, 0.56 mmol) in dioxane (7.5 ml) was heated at 100° C. overnight. The solvent was removed under reduced pressure and the crude material was purified by flash chromatography (hexanes ethyl acetate, 1:1) to yield the title compound (0.28 g, 97%) as an orange solid.

δ (CDCl3): 7.34 (m, 1H), 7.05 (d, 1H), 6.64 (d, 2H), 4.90 (bs, 1H), 2.92 (s, 3H), 2,90 (m, 1H), 2.80 (s, 3H), 1.80 to 1.00 (m, 10H).

Preparation 8

2-(4-Methylpiperazine-1-sulfonyl)phenylamine

The title compound (2.1 g, 80%) was obtained as a white solid from N-methylpiperazine and 2-nitrobenzenesulfonyl chloride following the same procedure as described in Preparation 2.

δ (DMSO-d6): 7.38 (m, 2H), 6.84 (d, 1H), 6.64 (t, 1H), 6.04 (bs, 2H), 2.94 (m, 4H), 2.36 (m, 4H), 2.14 (s, 3H).

Preparation 9

4-(2-Aminobenzenesulfonyl)piperazine-1-carboxylic acid tert-butyl ester

The title compound (2 g, 82%) was obtained as a white solid from piperazine-1-carboxylic acid tert-butyl ester and 2-nitrobenzenesulfonyl chloride following the same procedure as described in Preparation 2.

δ (DMSO-d6): 7.34 (m, 2H), 6.80 (d, 1H), 6.58 (t, 1H), 6.04 (bs, 2H), 3.29 (m, 4H), 2.82 (m, 4H), 1.30 (s, 9H).

Preparation 10

4-(2-Methylaminobenzenesulfonyl)piperazine-1-carboxylic acid tert-butyl ester

The title compound (0.24 g, 20%) was obtained as a white solid from compound of the Preparation 9 following the same procedure as described in Preparation 4.

δ (DMSO-d6): 7.44 (m, 2H), 6.72 (m, 2H), 6.24 (m, 1H), 3.39 (m, 4H), 2.92 (m, 4H), 2.80 (d, 3H), 1.30 (s, 9H).

Preparation 11

(2-Benzylphenyl)methylamine

The title compound (0.15 g, 28%) was obtained as a white solid from 2-benzylamine following the same procedure as described in Preparation 4.

δ (DMSO-d6): 7.18 (m, 6H), 6.58 (d, 1H), 6.44 (m, 2H), 5.04 (m, 1H), 3.74 (s, 2H), 2.65 (d, 3H).

Preparation 12

N-Cyclohexyl-N-methyl-2-propylaminobenzamide

The title compound (0.24 g, 73%) was obtained as a yellow solid fromN-cyclohexyl-N-methylamine and 1-Propyl-1H-benzo[d][1,3]oxazine-2,4-dione following the same procedure as described in Preparation 7.

δ (DMSO-d6): 7.20 (t, 1H), 6.95 (d, 1H), 6.60 (m, 1H), 5.80 (m, 1H), 5.00 (m, 1H), 3.00 (m, 2H), 2.80 (s, 3H), 1.60 (m, 1OH), 1.05 (m, 2H), 0.90 (m, 3H).

Preparation 13

N-Cyclohexyl-2-(cyclopropylmethylamino)-N-methylbenzamide

The title compound (0.29 g, 75%) was obtained as a yellow solid fromN-cyclohexyl-N-methylamine and 1-Cyclopropylmethyl-1H-benzo[d][1,3]oxazine-2,4-dione following the same procedure as described in Preparation 7.

δ (DMSO-d6): 7.20 (t, 1H), 7.00 (d, 1H), 6.64 (m, 2H), 5.10 (m, 1H), 2.95 (m, 3H), 2.80 (s, 3H), 1.70 (m, 8H), 1.15 (m, 3H), 0.44 (m, 2H), 0.18 (m, 2H).

Preparation 14

N-Cyclohexyl-N-methyl-2-pentylaminobenzamide

The title compound (1 g, 67%) was obtained as a yellow solid from N-cyclohexyl-N-methylamine and 1-Pentyl-1H-benzo[d][1,3]oxazine-2,4-dione following the same procedure as described in Preparation 7.

δ (DMSO-d6): 7.20 (t, 1H), 6.95 (d, 1H), 6.60 (m, 2H), 5.00 (s, 1H), 3.05 (m, 2H), 2.80 (s, 3H), 1.65 (m, 10H), 1.30 (m, 4H), 1.10 (m, 2H), 0.90 (m, 3H).

Preparation 15

N-Cyclohexyl-2-(cyclohexylmethylamino)-N-methylbenzamide

The title compound (0.3 g, 67%) was obtained as a orange solid from N-cyclohexyl-N-methylamine and 1-Cyclohexylmethyl-1H-benzo[d][1,3]oxazine-2,4-dione following the same procedure as described in Preparation 7.

δ (DMSO-d6): 7.18 (t, 1H), 6.94 (d, 1H), 6.58 (m, 2H), 5.20 (m, 1H), 3.04 (m, 2H), 2.84 (m, 2H), 2.80 (s, 3H), 1.64 (m, 12H), 1.14 (m, 8H).

Preparation 16

2-Benzylamino-N-cyclohexyl-N-methylbenzamide

The title compound (0.35 g, 82%) was obtained as a white solid fromN-cyclohexyl-N-methylamine and 1-Benzyl-1H-benzo[d][1,3]oxazine-2,4-dione following the same procedure as described in Preparation 7.

δ (DMSO-d6): 7.32 (m, 5H), 7.15 (t, 1H), 7.00 (d, 1H), 6.58 (m, 2H), 5.74 (m, 1H), 4.34 (d, 2H), 2.82 (m, 1H), 2.80 (s, 3H), 1.62 (m, 8H), 1.02 (m, 2H).

Preparation 17

2-Cyclopentanesulfonylphenylamine

A solution of cyclopentyl mercaptane (0.36 g, 3.54 mmol) in tetrahydrofuran (4 ml) was added dropwise to a stirred solution of NaH (0.14 g, 4.29 mmol) in tetrahydrofuran (2 ml) at 0° C. After 30 min. at 0° C., a solution of fluoronitrobenzene (0.5 g, 3.54 mmol) in tetrhydrofuran (4 ml) was added and the reaction mixture was allowed to stir at room temperature for an additional 5 h. The reaction mixture was poured into a saturated solution of $NH_4Cl$, extracted with ethyl acetate (100 ml) and washed with brine (10 ml). The organic layer was dried ($MgSO_4$) and concentrated under reduced pressure to yield 1-cyclopentylsulfanyl-2-nitrobenzene (0.79 g, 100%) that was used in the next step without further purification.

A solution of the crude 1-cyclopentylsulfanyl-2-nitrobenzene (0.79 g, 3.54 mmol) and magnesium monoperoxiftalate in a mixture of $CH_2Cl_2$ (41 ml) and MeOH (8 ml) was stirred overnight at room temperature. The solvent was removed under reduced pressure and the resulting crude was dissolved in $CH_2Cl_2$ (100 ml) and whased with sodium bicarbonate saturated solution (10 ml) and brine (10 ml). The organic layer was dried ($MgSO_4$) and the solvents removed under reduced pressure. The crude material was purified by flash chromatography (hexanes:diethyl ether, 1:1) to yield 1-cyclopentanesulfonyl-2-nitrobenzene (0.66 g, 80%) as a white solid.

δ (DMSO-d6): 8.24 (m, 2H), 4.14 (m, 1H), 1.92 (m, 4H), 1.62 (m, 4H).

A solution of 1-cyclopentanesulfonyl-2-nitrobenzene (0.66 g, 2.6 mmol) and $SnCl_2$ (2.4 g, 10.34 mmol) in EtOH (10 ml) was heated under reflux for 2 h. The solvent was removed under reduced pressure and the resulting crude was dissolved in AcOEt (100 ml) and washed with sodium hydroxide 2N (30 ml) and brine (10 ml). The organic layer was dried ($MgSO_4$) and the solvents removed under reduced pressure to give the title compound (0.38 g, 66%) as a white solid.

δ (DMSO-d6): 7.42 (d, 1H), 7.36 (t, 1H), 6.82 (d, 1H), 6.64 (t, 1H), 3.72 (m, 1H), 1.90 (m, 4H), 1.60 (m, 4H).

Preparation 18

2-(2-Methylpropane-2-sulfonyl)phenylamine

The title compound (0.2 g, 95%) was obtained as a white solid from tert-butyl mercaptane and fluoronitrobenzene following the same procedure as described in Preparation 17.

δ (DMSO-d6): 7.28 (m, 2H), 6.74 (d, 1H), 6.58 (t, 1H), 6.16 (bs, 2H), 1.18 (m, 9H).

Preparation 19

(S)-2-Amino-3-[4-(3-cyano[1,6]naphthyridin-2-ylamino)phenyl]propionic acid methyl ester hydrochloride A solution of (S)-3-(4-Aminophenyl)-2-tert-butoxycarbonylaminopropionic acid methyl ester (0.25 g, 0.84 mmol), 2-chloro[1,6]naphthyridine-3-carbonitrile (0.15 g, 0.77 mmol) (prepared according to the method of E. M. Hawes et al., *J. Med. Chem.* 1973,16, 849) and diisopropylethylamine (0.11 g, 0.84 mmol) in EtOH (1 ml) were heated under reflux for 3 h. The solvent was removed under reduced pressure and the resulting crude was purified by flash chromatography ($CH_2Cl_2$:AcOEt, 1:1) to yield (S)-2-tert-Butoxycarbonylamino-3-[4-(3-cyano[1,6]naphthyridin-2-ylamino)phenyl]propionic acid methyl ester (0.12 g, 34%) as a yellow solid.

(S)-2-tert-Butoxycarbonylamino-3-[4-(3-cyano[1,6] naphthyridin-2-ylamino)phenyl]propionic acid methyl ester (0.12 g) was disolved in dioxane (2 ml) and treated with saturated solution of hydrogen chloride in dioxane (2 ml) for 2 h at room temperature. The solvent was removed under reduced pressure to yield the title compound (0.1 g, 96%) as a white solid.

δ (DMSO-d6): 9.92 (bs, 1H), 9.29 (s, 1H), 9.16 (s, 1H), 8.62 (d, 1H), 8.56 (m, 2H), 7.80 (d, 2H), 7.62 (d, 1H), 7.26 (d, 2H), 4.38 (m, 1H), 3.75 (s, 3H), 3.15 (m, 2H).

Preparation 20

(S)-3-(4-Aminophenyl)-2-[3-(2-benzenesulfonylphenyl)ureido] propionic acid methyl ester A mixture of 2-benzenesulfonylphenylamine (1.88 g, 8.04 mmol) and diphosgene (0.48 ml, 4.02 mmol) in dioxane (25 ml) was heated at 60° C. for 16 h. The solvent was removed under reduced pressure. A solution of the crude isocyanate (8.04 mmol) in dichloromethane (14 ml) was slowly added to a solution of (S)-4-nitrophenylalanine methyl ester hydrochloride (2.31 g, 8.84 mmol) and triethylamine (3.7 ml, 26.52 mmol) in dichloromethane (14 ml) and the resulting reaction mixture was stirred at room temperature overnight. The reaction mixture was diluted with dichloromethane (100 ml) and washed with hydrochloric acid 1N (3×50 ml), saturated aqueous $NaHCO_3$ (3×50 ml) and brine (1×50 ml). The organic layer was dried ($MgSO_4$) and concentrated under reduced pressure to yield (S)-2-[3-(2-Benzenesulfonylphenyl)ureido]-3-(4-nitrophenyl) propionic acid methyl ester (3.64 g, 94%) that was used in the next step without further purification.

δ (CDCl3): 8.82 (s, 1H), 8.11 (m, 3H), 7.95 (d, 1H), 7.83 (d, 2H), 7.50 (m, 4H), 7.35 (d, 2H), 7.18 (t, 1H), 5.58 (d, 1H), 4.82 (m, 1H), 3.77 (s, 3H), 3.23 (m, 2H).

A solution of (S)-2-[3-(2-Benzenesulfonylphenyl)ureido]-3-(4-nitrophenyl) propionic acid methyl ester (3.64 g, 7.53 mmol) in ethanol (70 ml) was hydrogenated in the presence of a catalytic amount of Raney-Ni®. The catalyst was removed by filtration through Celite® and the solvent was eliminated under reduced pressure. The crude product was dissolved in dichloromethane (100 ml) and washed with saturated aqueous $NaHCO_3$ (3×50 ml). The organic layer was dried ($MgSO_4$) and concentrated under reduced pressure to yield the title compound (3.1 g, 91%) as a yellow solid.

δ (DMSO-d6): 8.41 (s, 1H), 8.01 (d, 1H), 7.88 (m, 3H), 7.76 (d, 1H), 7.61 (m, 1H), 7.50 (m, 3H), 7.18 (t, 1H), 6.84 (d, 2H), 6.43 (d, 2H), 4.89 (bs, 2H), 4.19 (m, 1H), 3.58 (s, 3H), 2.73 (m, 2H).

Preparation 21

(S)-2-[3-(2-Benzenesulfonylphenyl)ureido]-3-(4-hydroxyphenyl) propionic acid methyl ester A solution of 2-benzenesulfonylphenyl isocyanate (600 mg, 2.31 mmol, prepared as described in Preparation 20) in dichloromethane (4 ml) was slowly added to a solution of L-tyrosine methyl ester hydrochloride (589 mg, 2.54 mmol) and triethylamine (0.64 ml, 4.62 mmol) in dichloromethane (4 ml) and the resulting reaction mixture was stirred at room temperature overnight. The reaction mixture was diluted with dichloromethane (50 ml) and washed with hydrochloric acid 1N (2×20 ml), saturated aqueous NaHCO$_3$ (2×20 ml) and brine (1×20 ml). The organic layer was dried (MgSO$_4$) and concentrated under reduced pressure to yield the title compound (930 mg, 89%) as a viscous oil.

δ (CDCl3): 8.78 (s, 1H), 8.08 (d, 1H), 7.98 (d, 1H), 7.82 (d, 2H), 7.45 (m, 4H), 7.15 (t, 1H), 6.98 (d, 2H), 6.70 (d, 2H), 5.43 (d, 1H), 4.77 (m, 1H), 3.78 (s, 3H), 3.02 (m, 2H).

Preparation 22

3,5-Dimethoxyisonicotinic acid

A solution of 3,5-dimethoxypyridine (600 mg, 4.3 mmol) (prepared according to the method of Testaferri, L. et al Tetrahedron, 1985, 41, 1373) in THF (2.6 ml) was added to a solution of LDA [generated from n-BuLi (1.9 ml, 2.5 M in hexane, 4.73 mmol) and diisopropylamine (0.6 ml, 5.16 mmol)] in THF (2.6 ml) at −78° C. under nitrogen. The reaction mixture was stirred for 30 minutes at −78° C., transferred via cannula to a suspension of crushed solid CO$_2$ (30 g) in toluene (100 ml) under vigorous stirring and warmed to room temperature. The reaction is quenched by addition of water (20 ml) to and 1M NaOH (10 ml) and the aqueous layer separated, acidified to pH 4 with glacial acetic acid and extracted with 10% MeOH in dichloromethane (3×50 ml). The combined organic layers were dried (MgSO$_4$) and the solvent removed under vacuum to give the title compound (502 mg, 63%) as a white solid.

δ (DMSO-d6): 7.90 (s, 2H), 3.75 (s, 6H).

Preparation 23

(S)-2-Amino-3-(2'-cyanobiphenyl-4-yl) propionic acid methyl ester hydrochloride

Trifluoromethanesulfonic anhydride (3.27 ml, 19.47 mmol) was slowly added to a solution of Boc-L-tyrosine methyl ester (5.0 g, 16.93 mmol) and pyridine (4.11 ml, 50.79 mmol) in dichloromethane (145 ml) at 0° C. and the resulting orange solution was stirred at room temperature for 4 h. The reaction was quenched by addition of NaHCO$_3$ solution (150 ml) and the organic layer was separated, washed with saturated aqueous NaHCO$_3$ (2×100 ml) and brine (1×100 ml), and dried (MgSO$_4$). The solvent was concentrated under reduced pressure to yield (S)-2-tert-butoxycarbonylamino-3-(4-trifluoromethanesulfonyloxyphenyl) propionic acid methyl ester (6.52 g, 90%) that was used in the next step without further purification.

δ (CDCl3): 7.23 (m, 4H), 5.02 (m, 1H), 4.60 (m, 1H), 3.71 (s, 3H), 3.07 (m, 2H), 1.40 (m, 2H).

In a dry 100 ml round bottom flask fitted with a reflux condenser vented through a three way valve attached to a vacuum source and nitrogen gas was added (S)-2-tert-butoxycarbonylamino-3-(4-trifluoromethanesulfonyloxyphenyl) propionic acid methyl ester (3.26 g, 7.63 mmol), LiCl (3.56 g, 83.93 mmol), and Pd(PPh$_3$)$_4$ (0.44 g, 0.38 mmol) followed by 36 ml of dry dioxane. The mixture was stirred for 5 minutes and then hexamethyiditin (5.0 g, 15.26 mmol) was added. The reaction mixture was degassed and heated at 80° C. for 20 h. The mixture was then cooled to room temperature, diluted with 75 ml of hexane and stirred to give a precipitate. The suspension was filtered through Celite® and concentrated in vacuo to give a gum. The residue was purified by flash chromatography (15:1 to 3:1 hexanes/EtOAc) to give 1.23 g (36%) of (S)-2-tert -butoxycarbonylamino-3-(4-trimethylstannylphenyl) propionic acid methyl ester.

δ (CDCl3): 7.48 (d, 2H), 7.10 (d, 2H), 5.00 (d, 1H), 4.60 (m, 1H), 3.63 (s, 3H), 3.10 (m, 2H), 1.45 (m, 9H), 0.30 (s, 9H).

In a dry 25 ml round bottom flask fitted with a reflux condenser vented through a three way valve attached to a vacuum source and nitrogen gas, 2-bromobenzonitrile (557 mg, 3.06 mmol), tris(dibenzylideneacetone)dipalladium (0), (51 mg, 0.056 mmol), LiCl (353 mg, 8.34 mmol), and AsPh$_3$ (68 mg, 0.22 mmol) were added, followed by 13 ml of N-methylpyrrolidinone. The mixture was degassed and stirred for 10 minutes. A solution of (S)-2-tert-butoxycarbonylamino-3-(4-trimethylstannylphenyl) propionic acid methyl ester (1.23 g, 2.78 mmol) in N-methylpyrrolidinone (4.5 ml) was then added and the reaction was heated at 80° C. for 5 h and left overnight at room temperature. The reaction mixture was diluted with EtOAc (25 ml), quenched by addition of 10 ml of saturated KF solution and stirred for 20 minutes. The reaction mixture was partitioned between water (40 ml) and EtOAc (100 ml). The organic layer was separated, washed with water (6×40 mil and dried (MgSO$_4$). The solvents were removed under reduced pressure and the resulting crude was purified by flash chromatography (9:1 to 7:3 hexanes/EtOAc) to give (S)-2-tert-butoxycarbonylamino-3-(2'-cyano-biphenyl-4-yl) propionic acid methyl ester (570 mg, 54%) as a white solid.

δ (CDCl3): 7.78 (d, 1H), 7.63 (d, 1H), 7.50 (m, 4H), 7.24 (d, 2H), 5.04 (d, 1H), 4.63 (m, 1H), 3.75 (s, 3H), 3.18 (m, 2H), 1.42 (s, 9H).

3 ml of a saturated solution of HCl in dioxane were added to a solution of (S)-2-tert-butoxycarbonylamino-3-(2'-cyano-biphenyl-4-yl) propionic acid methyl ester (513 mg, 1.35 mmol) in dioxane (4 ml) and the resulting mixture was stirred at room temperature for 3 h. The solvent was concentrated in vacuo to yield the title compound (425 mg, 99%) that was used in the next step without further purification.

δ (DMSO-d6): 8.75 (bs, 3H), 7.98 (d, 1H), 7.80 (t, 1H), 7.60 (m, 4H), 7.40 (d, 2H), 4.36 (t, 1H), 3.71. (s, 3H), 3.23 (m, 2H).

Preparation 24

(S)-2-Amino-3-(2'-methoxybiphenyl-4-yl)-propionic acid methyl ester hydrochloride (S)-2-tert-Butoxycarbonylamino-3-(4-trifluoromethanesulfonyloxyphenyl) propionic acid methyl ester (1.88 g, 4.39 mmol, prepared as described in Preparation 23, was dissolved in glyme (58 ml) and water (4 ml). To this solution 2-methoxyphenylboronic acid (2.0 g, 13.16 mmol), tetrakistriphenylphosphine palladium (0) (2.79 g, 2.41 mmol) and potassium carbonate (2.12 g, 15.37 mmol) were added. The reaction mixture was degassed and then heated at 80° C. for 6 h. The mixture was diluted with EtOAc (100 ml), washed with saturated aqueous NaHCO$_3$ (100 ml) and brine (100 ml) and dried over MgSO$_4$. The mixture was filtered and concentrated in vacuo. The residue was purified by flash chromatography over silica gel (9:1 to 4:1 hexanes/EtOAc) to give (S)-2-tert-butoxycarbonylamino-3-(2'-methoxy-biphenyl-4-yl)-propionic acid methyl ester (1.1 g, 65%) as a white solid.

δ (CDCl3): 7.48 (d, 2H), 7.30 (d, 2H), 7.15 (m, 2H), 7.00 (m, 2H), 5.00 (bs, 1H), 4.60 (m, 1H), 3.90 (s, 3H), 3.80 (s, 3H), 3.10 (d, 2H), 1.43 (s, 9H).

7 ml of a saturated solution of HCl in dioxane were added to a solution of (S)2-tert-butoxycarbonylamino-3-(2'-methoxy-biphenyl-4-yl) propionic acid methyl ester (1.1 g, 2.83 mmol) in dioxane (4.5 ml) and the resulting mixture was stirred at room temperature for 3 h. The solvent was concentrated in vacuo to yield the title compound (898 mg, 99%) that was used in the next step without further purification.

Preparation 25

(S)-2-Amino-3-[4-([2,6]naphthyridin-1-ylamino) phenyl] propionic acid methyl ester (S)-3-(4-Amino-phenyl)-2-tert-butoxycarbonylamino propionic acid methyl ester (574 mg, 1.95 mmol), 1-Chloro-2,6-naphthyridine (350 mg, 2.13 mmol) (prepared according to the method of Van der Plas, H. C. et al *J. Heterocyclic Chem.* 1981, 18, 1349) and DIPEA (372 μl, 2.13 mmol) in 2-ethoxyethanol (0.5 ml) were stirred at 130° C. under $N_2$ overnight. The reaction mixture was partitioned between EtOAc (70 ml) and saturated aqueous $NaHCO_3$ (30 ml). The phases were separated and the aqueous layer re-extracted with EtOAc (3×30 ml). The combined organic extracts were dried ($MgSO_4$) and the solvents eliminated in vacuo. The residue was purified by flash chromatography (5:1 to 1:1 hexanes/EtOAc) to give (S)-2-tert-butoxycarbonylamino-3-[4-([2,6]naphthyridin-1-ylamino)phenyl] propionic acid methyl ester (385 mg, 47%) as an orange foam.

δ (CDCl3): 9.20 (s, 1H), 8.64 (d, 1H), 8.21 (d, 1H), 7.63 (m, 3H), 7.18 (m, 4H), 5.00 (d, 1H), 4.60 (m, 1H), 3.70 (s, 3H), 3.08 (m, 2H), 1.41 (s, 9H).

A solution of (S)-2-tert-butoxycarbonylamino-3-[4-([2,6] naphthyridin-1-ylamino)phenyl] propionic acid methyl ester (405 mg, 0.96 mmol) in dichloromethane (11.5 ml) was, treated with trifluoroacetic acid (11.5 ml) and stirred at room temperature for 2 h. The volatiles were removed in vacuo and the residue was partitioned between EtOAc (80 ml) and saturated aqueous $NaHCO_3$ (30 ml). The phases were separated and the aqueous layer re-extracted with EtOAc (3×30 ml). The combined organic extracts were dried ($MgSO_4$) and evaporated in vacuo to afford the title compound (308 mg, 100%) as a dark viscous oil.

δ (CDCl3): 9.20 (s, 1H), 8.64 (d, 1H), 8.22 (d, 1H), 7.70 (m, 3H), 7.20 (m, 4H), 3.78 (s, 3H), 3.70 (m, 1H), 3.10 (m, 1H), 2.85 (m, 1H).

Preparation 26

(S)-2-Amino-3-[4-([2,7]naphthyridin-1-ylamino) phenyl] propionic acid methyl ester The title compound was obtained as an orange viscous oil (42%) from (S)-3-(4-amino-phenyl)-2-tert-butoxycarbonylamino propionic acid methyl ester and 1-Chloro-2,7-naphthyridine (prepared according to the method of Failli, A. A., U.S. Pat. No. 4,859,671) following the same procedure as described in Preparation 25.

δ (DMSO-d6): 9.81 (s, 1H), 9.55.(s, 1H), 8.63 (d, 1H), 8.16 (d, 1H), 7.72 (m, 3H), 7.17 (m, 3H), 3.64 (s, 3H), 3.60 (m, 1H), 2.80 (m, 2H).

Preparation 27

(S)-2-Amino-3-[4-([2,6]naphthyridin-1-yloxy)phenyl] propionic acid methyl ester

To a solution of N-(tert-butyloxycarbonyl) tyrosine methyl ester (359 mg, 1.22 mmol) in DMF (2.5 ml) 1-Chloro-2,6-naphthyridine (200 mg, 1.22 mmol) and cesium carbonate (416 mg, 1.28 mmol) were added and the reaction mixture was stirred at 45° C. under $N_2$ for 48 h. The reaction mixture was partitioned between dichloromethane (50 ml) and water (50 ml) and the organic layer separated, washed with water (3×50 ml), dried ($MgSO_4$) and the solvent evaporated in vacuo. The residue was purified by flash chromatography (7:3 to 1:1 hexanes/EtOAc) to afford (S)-2-tert-butoxycarbonylamino-3-[4-([2,6]naphthyridin-1-yloxy)phenyl] propionic acid methyl ester (280 mg, 54%).

δ (CDCl3): 9.25 (s, 1H), 8.77 (d, 1H), 8.15 (d, 1H), 8.09 (d, 1H), 7.42 (d, 1H), 7.20 (m, 4H), 5.04 (d, 1H), 4.60 (m, 1H), 3.76 (s, 3H), 3.12 (m, 2H), 1.42 (m, 9H).

A solution of (S)-2-tert-butoxycarbonylamino-3-[4-([2,6] naphthyridin-1-yloxy)phenyl]propionic acid methyl ester (271 mg, 0.64 mmol) in dichloromethane (7.5 ml) was treated with trifluoroacetic acid (7.5 ml) and stirred at room temperature for 2 h. The volatiles were removed in vacuo and the residue was partitioned between EtOAc (60 ml) and saturated aqueous $NaHCO_3$ (25 ml). The phases were separated and the aqueous layer re-extracted with EtOAc (3×25 ml). The combined organic extracts were dried ($MgSO_4$) and evaporated in vacuo to afford the title compound (206 mg, 100%) as an oil that was used in the next step without further purification.

Preparation 28

(S)-2-Amino-3-[4-([2,7]naphthyridin-1-yloxy)phenyl] propionic acid methyl ester

The title compound was obtained as a viscous oil (76%) from N-(tert-butyloxycarbonyl) tyrosine methyl ester and 1-Chloro-2,7-naphthyridine following the same procedure as described in Preparation 27.

Example 1

(S)-2-(3-[2-(Cyclohexymethylcarbamoyl)phenyl] ureido)-3-[4-(2,6-dichloro-benzoylamino)phenyl] propionic acid methyl ester A solution of 2-amino-N-cyclohexyl-N-methylbenzamide (0.3 g, 1.27 mmol) and isocyanate from Preparation 1 (0.5 g, 1.27 mmol) in dichloromethane (20 ml) was stirred at room temperature overnight. The volatiles were removed in vacuo and the residue was partitioned between ethyl acetate (50 ml) and water (100 ml). The phases were separated and the aqueous layer re-extracted with ethyl acetate (2×50 ml). The combined organic extracts were washed consecutively with saturated sodium bicarbonate (50 ml), brine (50 ml), dried over sodium sulphate, filtered and evaporated under reduced pressure. The crude oil obtained was purified by flash chromatography (hexanes:ethyl acetate 1:1) to afford the title compound (0.4 g, 50%) as a white solid.

δ (DMSO-d6): 10.72 (s, 1H), 7.90 (m, 3H), 7.57 (m, 5H), 7.20 (m, 5H), 4.47 (m, 1H), 3.65 (s, 3H), 3.40 (m, 1H), 2.90 (m, 2H), 2.83 (s, 3H), 1.60 (m, 8H), 0.90 (m, 2H).

Example 2

(S)-2{-3-[2-(Cyclohexylmethylcarbamoyl)phenyl]
ureido}-3-[4-(2,6-dichlorobenzoyl amino)phenyl]
propionic acid A solution of the solid above (0.4 g, 0.64 mmol) and LiOH H$_2$O (0.06 g, 1.54 mmol) in tetrahydrofuran (5 ml) and H$_2$O (5 ml) was stirred at room temperature for 2 h. The organic solvent was removed under reduced pressure and the resulting aqueous solution was acidified with citric acid 5% until pH 6. The precipitate was collected by filtration to obtain the title (0.30 g, 77%) compound as a pale yellow solid.

m.p.: 183° C.

δ (DMSO-d6): 12.75 (bs, 1H), 10.68 (s, 1H), 7.90 (m, 3H), 7.58 (m, 5H), 7.18 (m, 5H), 4.40 (m, 1H), 3.38 (m, 1H), 2.90 (m, 2H), 2.86 (s, 3H), 1.54 (m, 8H), 0.90 (m, 2H).

Example 3

(S)-2-{3-[2-(Cyclohexylmethylcarbamoyl)-6-methoxyphenyl]ureido}-3-[4-(2,6-dichlorobenzoylamino)
phenyl]propionic acid methyl ester The title compound was obtained as a white solid from the compound of Preparation 1 and 2-amino-N-cyclohexyl-3-methoxy-N-methylbenzamide following the procedure described in Example 1.

δ (DMSO-d6, mixture of rotamers): 10.70 (s, 1H), 7.50 (m, 6H), 7.05 (m, 4H), 6.60 (m, 2H), 4.35 and 4.15 (bs, 1H, major/minor), 3.75 and 3.70 (s, 3H, major/minor), 3.47 (s, 3H), 3.20 (m, 1H), 2.83 (m, 2H), 2.70 and 2.60 (s, 3H, major/minor), 1.40 (m, 8H), 0.90 (m, 2H).

Example 4

(S)-2-{3-[2-(Cyclohexylmethylcarbamoyl)-6-methoxyphenyl]ureido}-3-[4-(2,6-dichlorobenzoylamino)
phenyl]propionic acid The title compound (40%) was prepared from the compound of Example 3 by hydrolysis in a similar manner to Example 2.

m.p.: 175° C.

δ (DMSO-d6, mixture of rotamers): 12.80 (bs, 1H), 10.71 (s, 1H), 7.47 (m, 6H), 7.16 (m, 3H), 7.01 (d, 1H), 6.73 (d, 1H), 6.54 and 6.45 (m, 1H, major/minor), 4.34 and 4.21 (bs, 1H, major/minor), 3.79 and 3.77 (s, 3H, major/minor), 2.95 (m, 2H), 2.80 and 2.65 (s, 3H, major/minor), 1.50 (m, 8H), 1.00 (m, 2H).

Example 5

(S)-3-[4-(2,6-Dichlorobenzoylamino)phenyl]-2-{3-
[2-(methylphenylcarbamoyl)phenyl]
ureido}propionic acid methyl ester The title compound was obtained as a white solid from the compound of Preparation 1 and 2-amino-N-methyl-N-phenylbenzamide following the procedure described in Example 1.

δ (CDCl$_3$): 8.62 (s, 1H), 8.10 (d, 1H), 7.56 (d, 2H), 7.32 (m, 4H), 7.20 (m, 6H), 7.05 (d, 2H), 6.80 (d, 1H), 6.65 (t, 1H), 5.45 (d, 1H), 4.84 (m, 1H), 3.79 (s, 3H), 3.48 (s, 3H), 3.18 (m, 2H).

Example 6

(S)-3-[4-(2,6-Dichlorobenzoylamino)phenyl]-2-{3-
[2-(methylphenylcarbamoyl)phenyl]
ureido}propionic acid The title compound (62%) was prepared from the compound of Example 5 by hydrolysis in a similar manner to Example 2.

m.p.: 178° C.

δ (DMSO-d6): 10.66 (s, 1H), 8.23 (s, 1H), 7.78 (d, 1H), 7.52 (m, 6H), 7.05 (m, 7H), 6.70 (d, 1H), 6.55 (d, 1H), 6.20 (t, 1H), 4.30 (m, 1H), 3.32 (s, 3H), 3.05 (m, 2H).

Example 7

(S)-3-[4-(2,6-Dichlorobenzoylamino)phenyl]-2-{3-
[2-(piperidine-1-carbonyl)phenyl]ureido}propionic
acid methyl ester The title compound was obtained as a white solid from the compound of Preparation 1 and (2-aminophenyl)piperidin-1-ylmethanone following the procedure described in Example 1.

δ (CDCl$_3$): 8.10 (s, 1H), 8.00 (d, 1H), 7.55 (d, 2H), 7.30 (m, 3H), 7.08 (m, 5H), 6.70 (m, 1H), 5.54 (d, 1H), 4.80 (m, 1H), 3.75 (s, 3H), 3.52 (m, 4H), 3.12 (m, 2H), 1.60 (m, 6H).

Example 8

(S)-3-[4-(2,6-Dichlorobenzoylamino)phenyl]-2-{3-
[2-(piperidine-1-carbonyl)phenyl]ureido}propionic
acid The title compound (45%) was prepared from the compound of Example 7 by hydrolysis in a similar manner to Example 2.

m.p.: 191° C. δ (DMSO-d6): 10.64 (s, 1H), 8.10 (s, 1H), 7.84 (d, 2H), 7.54 (m, 5H), 7.14 (m, 4H), 6.98 (t, 1H), 6.60 (m, 1H), 4.30 (m, 1H), 3.40 (m, 4H), 2.95 (m, 2H), 1.45 (m, 6H).

Example 9

(S)-3-[4-(2,6-Dichlorobenzoylamino)phenyl]-2-{3-
[5-methoxy-2-(piperidine-1-carbonyl)phenyl]
ureido}propionic acid methyl ester The title compound was obtained as a white solid from the compound of Preparation 1 and (2-amino-3-methoxyphenyl)piperidin-1-ylmethanone following the procedure described in Example 1.

δ (DMSO-d6): 10.70 (s, 1H), 7.60 (m, 5H), 7.19 (m, 3H), 7.00 (d, 1H), 6.75 (d, 1H), 6.68 (m, 1H), 4.42 (m, 1H), 3.80 (s, 3H), 3.65 (s, 3H), 3.43 (m, 2H), 3.10 (m, 2H), 2.95 (m, 2H), 1.40 (m, 6H).

Example 10

(S)-3-[4-(2,6-Dichlorobenzoylamino)phenyl]-2-{3-
[5-methoxy-2-(piperidine-1-carbonyl)phenyl]
ureido}propionic acid The title compound (25%) was prepared from the compound of Example 9 by hydrolysis in a similar manner to Example 2.

m.p.: 176° C.

δ (DMSO-d6): 12.80 (bs, 1H), 10.70 (s, 1H), 7.35 (m, 5H), 7.14 (m, 3H), 7.05 (d, 1H), 6.72 (d, 1H), 6.50 (m, 1H), 4.34 (m, 1H), 3.80 (s, 3H), 3.53 (m, 2H), 3.05 (m, 4H), 1.45 (m, 6H).

Example 11

(S)-2-{3-[2-(Cyclohexylisopropylcarbamoyl)-5-methoxyphenyl]ureido}-3-[4-(2,6-dichlorobenzoylamino)phenyl]propionic acid methyl ester The title compound was obtained as a white solid from the compound of Preparation 1 and 2-amino-N-cyclohexyl-N-isopropyl-3-methoxybenzamide following the procedure described in Example 1.

δ (DMSO-d6): 10.70 (s, 1H), 7.59 (m, 6H), 5.15 (m, 3H), 6.98 (d, 1H), 2.65 (m, 2H), 4.45 (m, 1H), 3.70 (s, 3H), 3.62 (s, 3H), 3.46 (m, 1H), 3.25 (m, 1H), 2.90 (m, 2H), 1.37 (m, 11H), 0.90 (m, 5H).

Example 12

(S)-2-{3-[2-(Cyclohexylisopropylcarbamoyl)-5-methoxyphenyl]ureido}-3-[4-(2,6-dichlorobenzoylamino)phenyl]propionic acid The title compound (40%) was prepared from the compound of Example 11 by hydrolysis in a similar manner to Example 2.

m.p.: 181° C.

δ (DMSO-d6): 10.70 (s, 1H), 7.57 (m, 6H), 7.17 (m, 3H), 6.98 (d, 1H), 6.69 (m, 1H), 6.51 (m, 1H), 4.35 (m, 1H), 3.45 (m, 1H), 2.95 (m, 3H), 1.50 (m, 11H), 1.02 (m, 5H).

Example 13

(S)-3-[4-(2,6-Dichlorobenzoylamino)phenyl]-2-[3-(2-phenylaminaphenyl)ureido]propionic acid methyl ester The title compound was obtained as a white solid from the compound of Preparation 1 and N-phenylbenzene-1,2-diamine following the procedure described in Example 1.

δ (DMSO-d6): 10.70 (s, 1H), 8.21 (s, 1H), 7.95 (d, 1H), 7.60 (m, 4H), 7.50 (m, 1H), 7.35 (s, 1H), 7.22 (d, 1H), 7.15 (m, 5H), 7.20 (t, 1H), 6.90 (t, 1H), 6.70 (m, 3H), 4.52 (m, 1H), 3.65 (s, 3H), 3.00 (dd, 1H), 2.90 (dd, 1H).

Example 14

(S)-3-[4-(2,6-Dichlorobenzoylamino)phenyl]-2-[3-(2-phenylaminophenyl)ureido]propionic acid The title compound (52%) was prepared from the compound of Example 13 by hydrolysis in a similar manner to Example 2.

m.p.: 174° C.

δ (DMSO-d6): 10.65 (s, 1H), 8.60 (bs, 1H), 7.90 (d, 1H), 7.52 (m, 6H), 7.15 (m, 6H), 6.90 (m, 2H), 6.75 (m, 3H), 4.25 (m, 1H), 2.94 (m, 2H).

Example 15

(S)-2-[3-(4-Benzenesulfonylphenyl)ureido]-3-[4-(2,6-dichlorobenzoylamino)phenyl]propionic acid methyl ester The title compound was obtained as a white solid from the compound of Preparation 1 and 4-benzenesulfonylphenylamine following the procedure described in Example 1.

δ (DMSO-d6): 10.70 (s, 1H), 9.27 (s, 1H), 7.90 (d, 2H), 7.82 (d, 2H), 7.59 (m, 10H), 7.18 (d, 2H), 6.61 (d, 1H), 4.52 (m, 1H), 3.70 (s, 3H), 3.10 (m, 2H).

Example 16

(S)-2-[3-(4-Benzenesulfonylphenyl)ureido]-3-[4-(2,6-dichlorobenzoylamino)phenyl]propionic acid The title compound (30%) was prepared from the compound of Example 15 by hydrolysis in a similar manner to Example 2.

m.p.: 222° C.

δ (DMSO-d6): 10.62 (s, 1H), 7.90 (d, 2H), 7.75 (d, 2H), 7.54 (m, 12H), 7.18 (d, 2H), 4.25 (m, 1H), 3.00 (m, 2H).

Example 17

(S)-3-[4-(2,6-Dichlorobenzoylamino)phenyl]-2-{3-[4-(4-nitrobenzenesulfonyl)phenyl]ureido}propionic acid methyl ester The title compound was obtained as a white solid from the compound of Preparation 1 and 4-(4-nitrobenzenesulfonyl)phenylamine following the procedure described in Example 1.

δ (DMSO-d6): 10.72 (s, 1H), 9.38 (s, 1H), 8.40 (d, 2H), 8.14 (d, 2H), 7.85 (d, 2H), 7.58 (m, 7H), 7.20 (d, 2H), 6.64 (d, 1H), 4.56 (m, 1H), 3.65 (s, 3H), 3.00 (m, 2H).

Example 18

(S)-3-[4-(2,6-Dichlorobenzoylamino)phenyl]-2-{3-[4-(4-nitrobenzenesulfonyl)phenyl]ureido}propionic acid The title compound (45%) was prepared from the compound of Example 17 by hydrolysis in a similar manner to Example 2.

m.p.: 223° C.

d (DMSO-d6): 10.71 (s, 1H), 9.52 (s, 1H), 8.40 (d, 2H), 8.16 (d, 2H), 7.85 (d, 2H), 7.60 (m, 7H), 7.20 (d, 2H), 6.52 (d, 1H), 4.38 (m, 1H), 3.00 (m, 2H).

Examples 19–23

These compounds were synthesized from the title compound of Preparation 1 and using the corresponding reactant respectively, following the procedure as described in Example 1 and Example 2. The ESI/MS data, HPLC retention times and yields are summarized in table 1.

TABLE 1

| Example | Y | Molecular Formula | ESI/MS m/e [M + H]+ | Retention Time (min) | Yield (%) |
|---|---|---|---|---|---|
| 19 | (2-(4-methylpiperazine-1-carbonyl)phenyl)amino | $C_{29}H_{29}Cl_2N_5O_5$ | 599 | 13.4 | 40 |
| 20 | (2-(N-butyl-N-(thiophen-2-ylmethyl)sulfamoyl)phenyl)amino | $C_{32}H_{32}Cl_2N_4O_6S_2$ | 704 | 18.6 | 10 |
| 21 | (2-(N-(thiophen-2-ylmethyl)sulfamoyl)phenyl)amino | $C_{28}H_{24}Cl_2N_4O_6S_2$ | 648 | 16.8 | 32 |
| 22 | (2-(N-phenylsulfamoyl)phenyl)amino | $C_{29}H_{24}Cl_2N_4O_6S$ | 628 | 16.8 | 60 |
| 23 | N-methyl-2-(phenylsulfonyl)aniline | $C_{30}H_{25}Cl_2N_3O_6S$ | 627 | 10.1 | 43 |

Example 24

(S)-2-[3-(2-Benzylcarbamoylphenyl)ureido]-3-[4-(2,6-dichlorobenzoylamino)phenyl]propionic acid a) To a solution of 2-amino-N-benzylbenzamide (0.23 g, 1 mmol) in dichloromethane (2 ml) was added a solution of isocyanate from Preparation 1 (0.39 g, 1 mmol) in dichloromethane (4 ml) at room temperature. After 48 h, the reaction mixture was filtered and the solid obtained was dissolved in dichloromethane (50 ml), washed with hydrochloric acid 1M solution and brine (2×50 ml), dried (MgSO$_4$) and concentrated in vacuo.

b) The crude material from a) was dissolved in tetrahydrofuran (6 ml) and water (6 ml). LiOH (0.024 g, 1 mmol) was then added and the reaction mixture was stirred at room temperature for 3 h. After removal under reduced pressure of tetrahydrofuran and addition of concentrated hydrochloric acid (0.3 ml), the crude acid was obtained as a white solid. Filtration and purification by flash chromatography (chloroform: methanol 10:1) yielded the title compound (0.25 g, 41%) as a white solid.

m.p.: 165° C.

δ (DMSO-d6): 12.70 (bs, 1H), 10.69 (s, 1H), 10.03 (s, 1H), 9.20 (t, 1H), 8.18 (d, 1H), 7.52 (m, 7H), 7.28 (m, 8H), 6.94 (t, 1H), 4.49 (d, 2H), 4.27 (m, 1H), 3.01 (m, 1H), 2.88 (m, 1H).

Example 25

(S)-2-[3-(2-Cyclohexylcarbamoylphenyl)ureido]-3-[4-(2,6-dichlorobenzoylamino)phenyl]propionic acid The title compound was obtained as a white solid from the compound of Preparation 1 and 2-amino-N-cyclohexylbenzamide following the procedure described in Example 24.

m.p.: 178° C.

δ (DMSO-d6): 10.67 (s, 1H), 9.86 (s, 1H), 8.37 (d, 1H), 8.13 (d, 1H), 7.52 (m, 7H), 7.29 (m, 3H), 6.93 (t, 1H), 4.25 (m, 1H), 3.75 (m, 1H), 3.04 (m, 1H), 2.84 (m, 1H), 1.78 (m, 4H), 1.59 (m, 1H), 1.29 (m, 5H).

Example 26

(S)-3-[4-(2,6-Dichlorobenzoylamino)phenyl]-2-[3-(2-phenylcarbamoylphenyl)ureido]propionic acid The title compound was obtained as a white solid from the compound of Preparation 1 and 2-amino-N-phenylbenzamide following the procedure described in Example 24.

m.p.: 184° C.

δ (DMSO-d6): 10.66 (s, 1H), 10.40 (s, 1H), 9.26 (s, 1H) 8.12 (d, 1H), 7.72 (m, 2H), 7.61 (m, 1H), 7.55 (m, 4H), 7.45 (m, 1H), 7.34 (m, 4H), 7.22 (m, 2H), 7.10 (t, 1H), 7.02 (t, 1H), 4.26 (m, 1H), 3.03 (m, 1H), 2.83 (m, 1H).

Example 27

(S)-2-{3-[2-(Cyclohexylmethylcarbamoyl)phenyl]ureido}-3-[4-(2,6-dichlorobenzoylamino)phenyl]propionic acid The title compound was obtained as a white solid from the compound of Preparation 1 and 2-amino-N-cyclohexylmethylbenzamide following the procedure described in Example 24.

m.p.: 201° C.

δ (DMSO-d6): 16.65 (s, 1H), 9.99 (s, 1H), 8.59 (m, 1H), 8.15 (d, 1H), 7.48 (m, 6H), 7.31 (t, 2H), 7.21 (m, 2H), 6.92 (t, 1H), 4.19 (m, 1H), 3.06 (m, 3H), 2.86 (m, 1H), 1.65 (m, 6H), 1.13 (m, 3H), 0.92 (m, 2H).

Example 28

(S)-2-[3-(2-tert-Butylcarbamoylphenyl)ureido]-3-[4-(2,6-dichlorobenzoylamino)phenyl]propionic acid The title compound was obtained as a white solid from the compound of Preparation 1 and 2-amino-N-tert-butylbenzamide following the procedure described in Example 24.

m.p.: 191° C.

δ (DMSO-d6): 10.66 (s, 1H), 9.57 (s, 1H), 7.99 (d, 1H), 7.92 (s, 1H), 7.55 (m, 7H), 7.29 (t, 1H), 7.23 (m, 2H), 6.92 (t, 1H), 4.23 (m, 1H), 3.02 (m, 1H), 2.83 (m, 1H), 1.37 (s, 9H).

Example 29

(S)-3-[4-(2,6-Dichlorobenzoylamino)phenyl]-2-{3-[2,4-dichloro-6-(cyclohexylmethylcarbamoyl)phenyl]ureido}propionic acid The title compound was obtained as a white solid from the compound of Preparation 1 and 2-amino-3,5-dichloro-N-cyclohexyl-N-methylbenzamide following the procedure described in Example 24.

m.p.: 202° C.

δ (DMSO-d6, mixture of rotamers): 12.85 (bs, 1H), 10.68 and 10.65 (s, 1H, minor/major), 8.24 (m, 1H), 7.66 (s, 1H), 7.51 (m, 5H), 7.28 (m, 1H), 7.17 (m, 2H), 6.56 (m, 1H), 4.21 (m, 1H), 3.59 (m, 1H), 2.90 (m, 2H), 2.80 and 2.65 (s, 3H, minor/major), 1.80–0.80 (m, 10H).

Example 30

(S)-2-{3-[2-(Cyclohexylmethylcarbamoyl)-6-methylphenyl]ureido}-3-[4(2,6-dichlorobenzoylamino)phenyl]propionic acid The title compound was obtained as a white solid from the compound of Preparation 1 and 2-amino-N-cyclohexyl-3,N-dimethylbenzamide following the procedure described in Example 24.

m.p.: 193° C.

δ (DMSO-d6, mixture of rotamers): 12.70 (bs, 1H), 10.69 (s, 1H), 7.75 (m, 1H), 7.56 (m, 5H), 7.18 (m, 4H), 6.95 (m, 1H), 6.49 (m, 1H), 4.35 (m, 1H), 3.36 (m, 1H), 3.00 (m, 2H), 2.82 and 2.75 (s, 3H, minor/major), 2.12 (s, 3H), 1.75–0.70 (m, 10H).

Example 31

(S)-2-{3-[2-(Cyclohexylmethylcarbamoyl)phenyl]-3-methylureido}-3-[4-(2,6-dichloro-benzoylamino)phenyl]propionic acid methyl ester A solution of the compound from Preparation. 7 (0.15 g, 0.63 mmol) and the isocyanate from Preparation 1 (0.25 g, 0.63 mmol) in acetonitrile (5 ml) was heated at 70° C. for 4 h. The volatiles were removed in vacuo and the residue was partitioned between ethyl acetate (10 ml) and water (25 ml). The phases were separated and the aqueous layer re-extracted with ethyl acetate (2×10 ml). The combined organic extracts were washed consecutively with saturated sodium bicarbonate (10 ml), brine (10 ml), dried with sodium sulphate, filtered and evaporated under reduced pressure. The obtained crude oil was purified by flash chromatography (hexanes:ethyl acetate 1:1) to afford the title compound as a yellow solid (0.1 g, 25%).

δ (DMSO-d6): 10.70 (s, 1H), 7.59 (m, 5H), 7.18 (m, 7H), 4.30 (m, 2H), 3.10 (s, 3H), 2.98 (s, 3H), 2.95 (m, 2H), 1.55 (m, 8H), 0.85 (m, 2H).

Example 32

(S)-2-{3-[2-(Cyclohexylmethylcarbamoyl)phenyl]-3-methylureido}-3-[4-(2,6-dichlorobenzoylamino)phenyl]propionic acid The title compound (0.06 g, 62%) was prepared from the compound of Example 31 by hydrolysis in a similar manner to Example 2.

m.p.: 201° C.

δ (DMSO-d6): 10.67 (s, 1H), 7.60 (m, 5H), 7.40 (m, 2H), 7.25 (m, 5H), 4.28 (m, 2H), 3.00 (m, 8H), 1.76 (m, 2H), 1.16 (m, 3H), 1.35 (m, 3H), 1.00 (m, 2H).

Example 33

(S)-2-{3-[4-(4-Chlorobenzenesulfonyl)thiophen-3-yl]ureido}-3-[4-(2,6-dichlorobenzoylamino)phenyl]propionic acid methyl ester The title compound was obtained as a white solid from the compound of Preparation 1 and 4-(4-chlorobenzenesulfonyl)thiophen-3-ylamine following the procedure described in Example 31.

δ (CDCl₃): 8.15 (s, 1H), 8.07 (d, 1H), 7.77 (d, 2H), 7.72 (d, 1H), 7.60 (d, 2H), 7.40 (m, 6H), 7.18 (d, 2H), 5.55 (d, 1H), 4.82 (m, 1H), 3.79 (s, 3H), 3.17 (m, 2H).

Example 34

(S)-2-{3-[4-(4-Chlorobenzenesulfonyl)thiophen-3-yl]ureido}-3-[4-(2,6-dichlorobenzoylamino)phenyl]propionic acid The title compound (40%) was prepared from the compound of Example 33 by hydrolysis in a similar manner to Example 2.

m.p.: 202° C.

δ (DMSO-d6): 10.70 (s, 1H), 8.45 (d, 1H), 8.23 (s, 1H), 8.07 (d, 2H), 7.89 (d, 1H), 7.56 (m, 8H), 7.23 (d, 2H), 4.32 (m, 1H), 3.05 (m, 1H), 2.86 (m, 1H).

Example 35

(S)-2-[3-(2-Benzenesulfonylphenyl)ureido]-3-[4-(2,6-dichlorobenzoylamino)phenyl]propionic acid methyl ester To a stirred solution of triphosgene (0.084 g, 0.28 mmol) in dichloromethane (1 ml) at 0° C. was slowly added a solution of 2-benzenesulfonylphenylamine (0.2 g, 0.87 mmol) in dichloromethane (1 ml) and the mixture was stirred at 0° C. for 15 minutes. After that, triethylamine (0.17 g, 1.74 mmol) in dichloromethane (2 ml) was added dropwise at 0° C. and the reaction was allowed to stir at room temperature for 3 h. To this solution a mixture of (S)-2-amino-3-[4-(2,6-dichlorobenzoylamino)phenyl]propionic acid methyl ester hydrochloride (0.35 g, 0.87 mmol) and triethylamine (0.9 g, 0.87 mmol) in dichloromethane (2 ml) was slowly added and the resulting reaction mixture was stirred at room temperature overnight. The volatiles were removed under reduced pressure and the residue was purified by column chromatography (Flash Biotage, dichloromethane:ethyl acetate 3:1) to yield the title compound (0.26 g, 50%) as a white solid.

δ (DMSO-d6): 10.75 (s, 1H), 8.50 (s, 1H), 8.16 (d, 1H), 7.92 (m, 4H), 7.60 (m, 9H), 7.25 (m, 3H), 4.40 (m, 1H), 3.70 (s, 3H), 3.08 (dd, 1H), 2.90 (dd, 1H).

Example 36

(S)-2-[3-(2-Benzenesulfonylphenyl)ureido]-3-[4-(2,6-dichlorobenzoylamino)phenyl]propionic acid The title compound (0.15 g, 58%) was prepared from the compound of Example 35 by hydrolysis in a similar manner to Example 2.

m.p.: 227° C.

δ (DMSO-d6): 10.75 (s, 1H), 8.49 (s, 1H), 8.06 (d, 1H), 7.99 (d, 1H), 7.92 (d, 2H), 7.83 (d, 1H), 7.59 (m, 9H), 7.28 (d, 2H), 7.22 (t, 1H), 4.31 (m, 1H), 3.06 (dd, 1H), 2.86 (dd, 1H).

Example 37

(S)-3-[4-(2,6-Dichlorobenzoylamino)phenyl]-2-{3-[2-(piperidine-1-sulfonyl)phenyl]ureido}propionic acid methyl ester The title compound was obtained as a white solid from the compound of Preparation 3 and (S)-2-amino-3-[4-(2,6-dichlorobenzoylamino)phenyl]propionic acid methyl ester hydrochloride following the procedure described in Example 35.

δ (DMSO-d6): 10.75 (s, 1H), 8.46 (s, 1H), 8.05 (d, 1H), 7.92 (d, 1H), 7.55 (m, 7H), 7.20 (m, 3H), 4.42 (m, 1H), 3.68 (s, 3H), 3.10 (dd, 1H), 2.90 (m, 5H), 1.40 (m, 6H).

Example 38

(S)-3-[4-(2,6-Dichlorobenzoylamino)phenyl]-2-{3-[2-(piperdine-1-sulfonyl)phenyl]ureido}propionic acid The title compound (20%) was prepared from the compound of Example 37 by hydrolysis in a similar manner to Example 2.

m.p.: 225° C.

δ (DMSO-d6): 12.72 (bs, 1H), 10.71 (s, 1H), 7.92 (m, 2H), 7.55 (m, 7H), 7.25 (d, 2H), 7.16 (t, 1H), 4.33 (m, 1H), 3.07 (dd, 1H), 2.87 (m, 5H), 1.43 (m, 4H), 1.35 (m, 2H).

Example 39

(S)-2-{3-[2-(Cyclohexylmethylsulfamoyl)phenyl]ureido}-3-[4-(2,6-dichlorobenzoylamino)phenyl]propionic acid methyl ester The title compound was obtained as a white solid from the compound of Preparation 2 and (S)-2-amino-3-[4-(2,6-dichlorobenzoylamino)phenyl]propionic acid methyl ester hydrochloride following the procedure described in Example 35.

δ (DMSO-d6): 10.70 (s, 1H), 8.35 (s, 1H), 8.06 (d, 1H), 7.90 (d, 1H), 7.70 (d, 1H), 7.52 (m, 6H), 7.22 (d, 2H), 7.10 (t, 2H), 4.45 (m, 1H), 3.68 (s, 3H), 3.52 (m, 1H), 3.10 (dd, 1H), 2.85 (dd, 1H), 2.60 (s, 3H), 1.52 (m, 4H), 1.15 (m, 6H).

Example 40

(S)-2-{3-[2-(Cyclohexylmethylsulfamoyl)phenyl]ureido}-3-[4-(2,6-dichlorobenzoylamino)phenyl]propionic acid The title compound (52%) was prepared from the compound of Example 39 by hydrolysis in a similar manner to Example 2.

m.p.: 185° C.

δ (DMSO-d6): 10.70 (s, 1H), 8.32 (s, 1H), 7.89 (d, 2H), 7.71 (d, 1H), 7.56 (m, 4H), 7.49 (m, 2H), 7.24 (d, 2H), 7.11 (t, 1H), 4.34 (m, 1H), 3.47 (m, 3H), 3.07 (dd, 1H), 2.82 (dd, 1H), 2.52 (s, 3H), 1.45 (m, 3H), 1.20 (m, 4H), 1.02 (m, 3H).

Example 41

(S)-2-[3-(2-Benzylphenyl)ureido]-3-[4-(2,6-dichlorobenzoylamino)phenyl]propionic acid methyl ester The title compound was obtained as a white solid from 2-benzylphenylamine and (S)-2-amino-3-[4-(2,6-dichlorobenzoylamino)phenyl]propionic acid methyl ester hydrochloride following the procedure described in Example 35.

δ (DMSO-d6): 10.72 (s, 1H), 8.10 (s, 1H), 7.65 (m, 6H), 7.19 (m, 7H), 6.95 (m, 4H), 4.55 (m, 1H), 3.91 (s, 2H), 3.68 (s, 3H), 3.00 (m, 2H).

Example 42

(S)-2-[3-(2-Benzylphenyl)ureido]-3-[4-(2,6-dichlbrobenzoylamino)phenyl]propionic acid The title compound (43%) was prepared from the compound of Example 41 by hydrolysis in a similar manner to Example 2.

m.p.: 232° C.

δ (DMSO-d6): 10.68 (s, 1H), 8.18 (s, 1H), 7.74 (d, 1H), 7.54 (m, 6H), 7.15 (m, 8H), 6.92 (m, 1H), 6.70 (d, 1H), 4.30 (m, 1H), 3.92 (dd, 2H), 3.00 (m, 2H).

Example 43

(S)-3-[4-(2,6-Dichlorobenzoylamino)phenyl]-2-[3-(2-phenylsulfanylphenyl)ureido]propionic acid methyl ester The title compound was obtained as a white solid from 2-phenylsulfanylphenylamine and (S)-2-amino-3-[4-(2,6-dichlorobenzoylamino)phenyl]propionic acid methyl ester hydrochloride following the procedure described in Example 35.

δ (DMSO-d6): 10.71 (s, 1H), 8.45 (s, 1H), 8.10 (d, 1H), 7.60 (m, 6H), 7.32 (m, 5H), 7.15 (m, 4H), 7.00 (t, 1H), 4.45 (m, 1H), 3.64 (s, 3H), 3.00 (m, 2H).

Example 44

(S)-3-[4-(2,6-Dichlorobenzoylamino)phenyl]-2-[3-(2-phenylsulfanylphenyl)ureido]propionic acid The title compound (60%) was prepared from the compound of Example 43 by hydrolysis in a similar manner to Example 2.

m.p.: 220° C.

δ (DMSO-d6): 10.70 (s, 1H), 8.42 (s, 1H), 8.15 (d, 1H), 7.58 (m, 6H), 7.32 (m, 5H), 7.12 (m, 4H), 7.00 (t, 1H), 4.28 (m, 1H), 3.00 (dd, 1H), 2.86 (dd, 1H).

Example 45

(S)-2-{3-[5-Chloro-2-(4-chlorobenzenesulfonyl) phenyl]ureido}-3-[4-(2,6-dichlorobenzoylamino) phenyl]propionic acid methyl ester The title compound was obtained as a white solid from 5-chloro-2-(4-chlorobenzenesulfonyl)phenylamine and (S)-2-amino-3-[4-(2,6-dichlorobenzoylamino)phenyl]propionic acid methyl ester hydrochloride following the procedure described in Example 35.

δ (DMSO-d6): 10.72 (s, 1H), 7.33 (bs, 1H), 8.48 (s, 1H), 8.25 (s, 1H); 7.95 (m, 4H), 7.60 (m, 5H), 7.28 (m, 4H), 4.32 (m, 1H), 3.70 (s, 3H), 3.02 (dd, 1H), 2.90 (dd, 1H).

Example 46

(S)-2-{3-[5-Chloro-2-(4-chlorobenzenesulfonyl) phenyl]ureido}-3-[4-(2,6-dichlorobenzoylamino) phenyl]propionic acid The title compound (80%) was prepared from the compound of Example 45 by hydrolysis in a similar manner to Example 2.

m.p.: 239° C.

δ (DMSO-d6): 10.70 (s, 1H), 8.60 (s, 1H), 8.12 (m, 6H), 7.61 (m, 7H), 7.25 (m, 3H), 4.21 (m, 1H), 3.10 (dd, 1H), 2.85 (dd, 1H).

Example 47

(S)-2-[3-(2-Benzenesulfonyl-5-chlorophenyl)ureido]-3-[4-(2,6-dichlorobenzoylamino)phenyl]propionic acid methyl ester The title compound was obtained as a white solid from 2-benzenesulfonyl-5-chlorophenylamine and (S)-2-amino-3-[4-(2,6-dichlorobenzoylamino)phenyl]propionic acid methyl ester hydrochloride following the procedure described in Example 35.

δ (DMSO-d6): 10.74 (s, 1H), 8.60 (s, 1H), 8.35 (d, 1H), 7.92 (m, 4H), 7.60 (m, 7H), 7.26 (m, 4H), 4.40 (m, 1H), 3.70 (s, 3H), 3.10 (dd, 1H), 2.90 (dd, 1H).

Example 48

(S)-2-[3-(2-Benzenesulfonyl-5-chlorophenyl)ureido]-3-[4-(2,6-dichlorobenzoyl amino)phenyl]propionic acid The title compound (25%) was prepared from the compound of Example 47 by hydrolysis in a similar manner to Example 2.

m.p.: 242° C.

δ (DMSO-d6): 10.72 (s, 1H), 8.58 (s, 1H), 7.80 (m, 4H), 7.53 (m, 7H), 7.15 (m, 4H), 4.30 (m, 1H), 3.00 (m, 2H).

Example 49

(S)-2-{3-[2,4-Dibromo-6-(cyclohexylmethylcarbamoyl)phenyl]ureido}-3-[4-(2,6-dichlorobenzoylamino) phenyl]propionic acid methyl ester The title compound was obtained as a white solid from 2-Amino-3,5-dibromo-N-cyclohexyl-N-methyl-benzamide and (S)-2-amino-3-[4-(2,6-dichlorobenzoylamino)phenyl] propionic acid methyl ester hydrochloride following the procedure described in Example 35.

δ (CDCl3, mixture of rotamers): 7.98 (m, 1H), 7.67 (m, 3H), 7.24 (m, 7H), 6.76 (m, 1H), 4.32 (m, 1H), 3.67 and 3.53 (s, 3H, major/minor), 3.49 (m, 1H), 3.04 (m, 2H), 2.86 and 2.58 (s, 3H, major/minor), 1.80–0.80 (m, 10H).

Example 50

(S)-2-{3-[2,4-Dibromo-6-(cyclohexylmethylcarbamoyl)phenyl]ureido}-3-[4-(2,6-dichlorobenzoylamino)phenyl]propionic acid The title compound (65%) was prepared from the compound of Example 49 by hydrolysis in a similar manner to Example 2.
m.p.: 193° C.
δ (DMSO-d6, mixture of rotamers): 12.85 (bs, 1H), 10.70 (s, 1H), 8.19 and 8.13 (s, 1H, major/minor), 7.91 (s, 1H), 7.57 (m, 6H), 7.18 (m, 2H), 6.62 (m, 1H), 4.40 (m, 1H), 4.19 (m, 1H), 2.98 (m, 2H), 2.76 and 2.64 (s, 3H, major/minor), 1.80–0.80 (m, 10H).

Example 51

(S)-3-[4-(2,6-Dichlorobenzoylamino)phenyl]-2-{3-[2-(toluene-4-sulfonyl)-5-trifluoromethylphenyl]ureido}propionic acid methyl ester A mixture of 2-(toluene-4-sulfonyl)-5-trifluoromethylphenylamine (0.2 g, 0.63 mmol) and diphosgene (0.061 g, 0.31 mmol) in dioxane (2 ml) was heated at 60° C. for 16 h. The solvent was removed under reduced pressure. The crude isocyanate was slowly added to a solution of (S)-2-amino-3-[4-(2,6-dichlorobenzoylamino)phenyl]propionic acid methyl ester hydrochloride (0.25 g, 0.63 mmol) and triethylamine (0.063 g, 0.63 mmol) in dichloromethane (2 ml) and the resulting reaction mixture was stirred at room temperature overnight. The precipitate obtained was collected by filtration, washed several times with dichloromethane and dried under vacuum to yield the title compound (0.36 g, 82%) as a white solid.
δ (DMSO-d6): 10.74 (s, 1H), 8.65 (s, 1H), 8.42 (d, 1H), 8.30 (d, 1H), 8.20 (d, 1H), 7.86 (d, 2H), 7.65 (d, 2H), 7.58 (m, 6H), 7.30 (m, 4H), 4.40 (m, 1H), 3.70 (s, 3H), 3.00 (m, 2H), 2.39 (s, 3H).

Example 52

(S)-3-[4-(2,6-Dichlorobenzoylamino)phenyl]-2-{3-[2-(toluene-4-sulfonyl)-5-trifluoromethylphenyl]ureido}propionic acid The title compound (60%) was prepared from the compound of Example 51 by hydrolysis in a similar manner to Example 2.
m.p.: 233° C.
δ (DMSO-d6): 10.72 (s, 1H), 8.65 (s, 1H), 8.32 (s, 1H), 8.20 (d, 1H), 7.88 (d, 2H), 7.56 (m, 7H), 7.32 (d, 2H), 7.25 (d, 2H), 4.20 (m, 1H), 3.10 (dd, 1H) 2.90 (dd, 1H), 2.37 (s, 3H).

Example 53

(S)-2-{3-[2-Chloro-5-(toluene-4-sulfonyl)phenyl]ureido}-3-[4-(2,6-dichlorobenzoylamino)phenyl]propionic acid methyl ester The title compound was obtained as a white solid from 2-chloro-5-(toluene-4-sulfonyl)phenylamine and (S)-2-amino-3-[4(2,6-dichlorobenzoylamino)phenyl]propionic acid methyl ester hydrochloride following the procedure described in Example 51.
δ (DMSO-d6): 10.78 (s, 1H), 8.61 (s, 1H), 8.40 (d, 2H), 7.95 (m, 2H), 7.82 (m, 2H), 7.70 (d, 2H), 7.60 (m, 3H), 7.30 (m, 5H), 4.35 (m, 1H), 3.70 (s, 3H), 3.10 (dd, 1H), 2.90 (dd, 1H), 2.40 (s, 3H).

Example 54

(S)-2-{3-[2-Chloro-5-(toluene-4-sulfonyl)phenyl]ureido}-3-[4-(2,6-dichlorobenzoylamino)phenyl]propionic acid The title compound (32%) was prepared from the compound of Example 53 by hydrolysis in a similar manner to Example 2.
m.p.: 241° C.
δ (DMSO-d6): 10.70 (s, 1H), 8.59 (s, 1H), 8.19 (bs, 1H), 7.92 (m, 4H), 7.70 (d, 2H), 7.60 (m, 5H), 7.28 (m, 5H), 4.18 (m, 1H), 3.10 (dd, 1H), 2.90 (dd, 1H), 2.40 (s, 3H).

Example 55

(S)-2-{3-[5-Chloro-2-(2,5-dimethoxybenzenesulfonyl)phenyl]ureido}-3-[4-(2,6-dichlorobenzoylamino)phenyl]propionic acid methyl ester The title compound was obtained as a white solid from 5-chloro-2-(2,5-dimethoxybenzenesulfonyl)phenylamine and (S)-2-amino-3-[4-(2,6-dichlorobenzoylamino)phenyl]propionic acid methyl ester hydrochloride following the procedure described in Example 51.
δ (DMSO-d6): 10.68 (s, 1H), 8.65 (s, 1H), 8.34 (d, 1H), 8.18 (s, 1H), 7.90 (d, 1H), 7.73 (s, 1H), 7.52 (m, 5H), 7.20 (m, 5H), 4.38 (m, 1H), 3.89 (s, 3H), 3.62 (s, 3H), 3.58 (s, 3H), 2.95 (m, 2H).

Example 56

(S)-2-{3-[5-Chloro-2-(2,5-dimethoxybenzenesulfonyl)phenyl]ureido}-3-[4-(2,6-dichlorobenzoylamino)phenyl]propionic acid The title compound (43%) was prepared from the compound of Example 55 by hydrolysis in a similar manner to Example 2.
m.p.: 180° C.
δ (DMSO-d6): 10.65 (s, 1H), 8.57 (s, 1H), 8.34 (s, 1H), 7.95 (bs, 1H), 7.85 (d, 1H), 7.75 (s, 1H), 7.45 (m, 5H), 7.15 (m, 5H), 4.24 (m, 1H), 3.73 (s, 3H), 3.62 (s, 3H), 2.95 (m, 2H).

Example 57

(S)-2-[3-(2-Benzenesulfonylpyridin-3-yl)ureido]-3-[4-(2,6-dichlorobenzoylamino)phenyl]propionic acid methyl ester The title compound is obtained as a white solid from 2-benzenesulfonylpyridin-3-ylamine and (S)-2-amino-3-[4-(2,6-dichlorobenzoylamino)phenyl]propionic acid methyl ester hydrochloride following the procedure described in Example 51.
δ (DMSO-d6): 10.75 (s, 1H), 8.92 (s, 1H), 8.48 (d, 1H), 8.35 (d, 1H), 8.22 (s, 1H), 7.98 (m, 2H), 7.60 (m, 9H), 7.23 (m, 2H), 4.44 (m, 1H), 3.68 (s, 3H), 3.00 (m, 2H).

Example 58

(S)-2-[3-(2-Benzenesulfonylpyridin-3-yl)ureido]-3-[4-(2,6-dichlorobenzoylamino)phenyl]propionic acid The title compound (71%) was prepared from the compound of Example 57 by hydrolysis in a similar manner to Example 2.
m.p.: 181° C.
δ (DMSO-d6): 10.69 (s, 1H), 8.94 (s, 1H), 8.43 (d, 1H), 8.19 (s, 1H), 8.03 (m, 3H), 7.68 (m, 9H), 7.27 (d, 2H), 4.30 (m, 1H), 3.00 (m, 2H).

Example 59

(S)-2-[3-(2-Benzenesulfonylphenyl)ureido]-3-(2',6'-dimethoxybiphenyl-4-yl) propionic acid methyl ester The title compound is obtained as a white solid from 2-benzenesulfonylphenylamine and (S)-2-amino-3-(2',6'-dimethoxybiphenyl-4-yl)propionic acid methyl ester hydrochloride following the procedure described in Example 51.
δ (CDCl$_3$): 8.68 (s, 1H), 8.04 (dd, 1H), 7.81 (d, 1H), 7.46 (m, 4H), 7.27 (m, 6H), 6.63 (d, 2H), 5.53 (d, 1H), 4.81 (m, 1H), 3.78 (s, 3H), 3.72 (s, 6H), 3.19 (d, 2H).

Example 60

(S)-2-[3-(2-Benzenesulfonylphenyl)ureido]-3-(2',6'-dimethoxybiphenyl-4-yl) propionic acid The title compound (92%) was prepared from the compound of Example 59 by hydrolysis in a similar manner to Example 2.
m.p.:119° C.
δ (DMSO-d6): 12.70 (bs, 1H), 8.55 (s, 1H), 8.15 (d, 1H), 8.00 (m, 3H), 7.82 (d, 1H), 7.56 (m, 4H), 7.24 (m, 6H), 6.71 (d, 2H), 4.34 (m, 1H), 3.68 (s, 6H), 3.17 (m, 1H), 2.93 (m, 1H).

Example 61

(S)-3-{4-[(3,5-Dichloropyridine-4-carbonyl)amino]phenyl}-2-{3-[2-(piperidine-1-sulfonyl)phenyl]ureido}propionic acid methyl ester The title compound is obtained as a white solid from the compound of Preparation 3 and (S)-2-Amino-3-{4-[(3,5-dichloropyridinecarbonyl)amino]phenyl}propionic acid methyl ester triflouroacetate following the procedure described in example Example 51.
δ (DMSO-d6): 10.82 (s, 1H), 8.81 (s, 2H), 8.42 (s, 1H), 8.08 (d, 1H), 7.92 (d, 1H), 7.63 (m, 4H), 7.28 (m, 3H), 4.42 (m, 1H), 3.68 (s, 3H), 2.98 (m, 6H), 1.43 (m, 6H).

Example 62

(S)-3-{4-[(3,5-Dichloropyridine-4-carbonyl)amino]phenyl}-2-{3-[2-(piperidine-1-sulfonyl)phenyl]ureido}propionic acid The title compound (92%) was prepared from the compound of Example 61 by hydrolysis in a similar manner to example Example 2.
m.p.: 223° C.
δ (DMSO-d6): 10.84 (s, 1H), 8.80 (s, 2H), 8.39 (s, 1H), 7.90 (d, 2H), 7.56 (m, 4H), 7.20 (m, 3H), 4.38 (m, 1H), 2.95 (m, 6H), 1.42 (m, 6H).

Example 63

(S)-2-{3-[5-Chloro-2-(2,5-dimethoxybenzenesulfonyl)phenyl]ureido}-3-{4-[(3,5-dichloropyridine-4-carbonyl)amino]phenyl}propionic acid methyl ester The title compound is obtained as a white solid from 5-Chloro-2-(2,5-dimethoxybenzenesulfonyl)phenylamine and (S)-2-Amino-3-{4[(3,5-dichloropyridine-4-carbonyl)amino]phenyl}propionic acid methyl ester triflouroacetate following the procedure described in Example 51.
δ (DMSO-d6): 10.85 (s, 1H), 8;82 (s, 2H), 8.62 (s, 1H), 8.36 (d, 1H), 8.12 (s, 1H), 7.84 (d, 1H), 7.70 (s, 1H), 7.56 (d, 2H), 7.23 (m, 5H), 4.38 (m, 1H), 8.83 (s, 3H), 3.60 (s, 3H); 3.56 (s, 3H), 2.85 (m, 2H).

Example 64

(S)-2-{3-[5-Chloro-2-(2,5-dimethoxybenzenesulfonyl)phenyl]ureido}-3-{4-[(3,5-dichloropyridine-4-carbonyl)amino]phenyl}propionic acid The title compound (91%) was prepared from the compound of Example 63 by hydrolysis in a similar manner to Example 2.
m.p.: 168° C.
δ (DMSO-d6): 10.82 (s, 1H), 8.78 (s, 2H), 8.58 (s, 1H), 8.18 (s, 1H), 7.89 (d, 1H), 7.72 (s, 1H), 7.50 (d, 2H), 7.15 (m, 5H), 4.28 (m, 1H), 3.80 (s, 3H), 3.65 (s, 3H), 2.94 (m, 2H).

Example 65

(S)-2-{3-[2-(Cyclohexylmethylsulfamoyl)phenyl]ureido}-3-{4-[(3,5-dichloropyridine-4-carbonyl)amino]phenyl}propionic acid methyl ester The title compound is obtained as a white solid from the compound of Preparation 2 and (S)-2-Amino-3-{4-[(3,5-dichloropyridine-4-carbonyl)amino]phenyl}propionic acid methyl ester triflouroacetate following the procedure described in Example 51.
δ (DMSO-d6): 10.90 (s, 1H), 8.60 (s, 2H), 8.39 (s, 1H), 8.15 (d, 1H), 7.86 (d, 1H), 7.70 (d, 1H), 7.56 (m, 3H), 7.24 (d, 2H), 7.12 (t, 1H), 4.43 (m, 1H), 3.66 (s, 3H), 3.62 (m, 1H), 3.00 (m, 2H), 2.62 (s, 3H), 1.50 (m, 4H), 1.20 (m, 6H).

Example 66

(S)-2-{3-[2-(Cyclohexylmethylsulfamoyl)phenyl]ureido}-3-{4-[(3,5-dichloropyridine-4-carbonyl)amino]phenyl}propionic acid The title compound (85%) was prepared from the compound of Example 65 by hydrolysis in a similar manner to Example 2.
m.p.: 214° C.
δ (DMSO-d6): 10.90 (s, 1H), 8.68 (s, 2H), 8:30 (s, 1H), 7.90 (m, 2H), 7.64 (d, 1H), 7.56 (m, 3H), 7.24 (d, 2H), 7.15 (t, 1H), 4.38 (m, 1H), 3.60 (m, 1H), 3.00 (m, 2H), 2.64 (s, 3H), 1.52 (m, 4H), 1.20 (m, 6H).

Example 67

(S)-2-[3-(2-Benzenesulfonyl-5chlorophenyl)ureido]-
3-{4-[(3,5-dichloropyridine-4-carbonyl)amino]
phenyl}propionic acid methyl ester The title compound is obtained as a white solid from 2-Benzenesulfonyl-5-chlorophenylamine and (S)-2-Amino-3-{4-[(3,5-dichloropyridine-4-carbonyl)amino]phenyl}propionic acid methyl ester triflouroacetate following the procedure described in Example 51.

δ (DMSO-d6): 10.90 (s, 1H), 9.40 (bs, 1H), 8.82 (s, 2H), 8.60 (s, 1H), 8.38 (d, 1H), 8.00 (m, 4H), 7.62 (m, 5H), 7.30 (m, 3H), 4.42 (m, 1H), 3.70 (s, 3H), 3.00 (m, 2H).

Example 68

(S)-2-[3-(2-Benzenesulfonyl-5-chlorophenyl)ureido]-3-{4-[(3,5-dichloropyridine-4-carbonyl)amino]
phenyl}propionic acid The title compound (73%) was prepared from the compound of Example 67 by hydrolysis in a similar manner to Example 2.

m.p.: 204° C.

δ (DMSO-d6): 12.80 (bs, 1H), 10.90 (s, 1H), 8.80 (s, 2H), 8.58 (s, 1H), 8.25 (d, 1H), 8.00 (m, 4H), 7.64 (m, 5H), 7.28 (m, 3H), 4.38 (s, 1H), 3.00 (m, 2H).

Example 69

(S)-2-[3-(2-Benzenesulfonylphenyl)ureido]-3-{4-[(3,5-dichloropyridine-4-carbonyl)amino]
phenyl}propionic acid methyl ester The title compound is obtained as a white solid from 2-Benzenesulfonylphenylamine and (S)-2-Amino-3-{4-[(3,5-dichloropyridine-4-carbonyl)amino]phenyl}propionic acid methyl ester triflouroacetate following the procedure described in Example 51.

δ (DMSO-d6): 10.90 (s, 1H), 8.84 (d, 2H), 8.52 (s, 1H), 8.20 (d, 1H), 7.90 (m, 4H), 7.60 (m, 6H), 7.26 (m, 3H), 4.40 (m, 1H), 3.70 (s, 3H), 3.00 (m, 2H).

Example 70

(S)-2-[3-(2-Benzenesulfonylphenyl)ureido]-3-{4-[(3,5-dichloropyridine-4-carbonyl)amino]
phenyl}propionic acid The title compound (56%) was prepared from the compound of Example 69 by hydrolysis in a similar manner to Example 2.

m.p.: 214° C.

δ (DMSO-d6): 10.90 (s, 1H), 8.80 (d, 2H), 8.48 (s, 1H), 7.92 (m, 5H), 7.50 (m, 6H), 7.26 (m, 3H), 4.30 (m, 1H), 3.00 (m, 2H).

Example 71

(S)-3-[4-(2,6-Dichlorobenzoylamino)phenyl]-2-{3-[2-(toluene-4-sulfonyl)pyridin-3-yl]ureido}propionic
acid methyl ester The title compound is obtained as a white solid from 2-(Toluene-4-sulfonyl)pyridin-3-ylamine and (S)-2-amino-3-[4-(2,6-dichlorobenzoylamino)phenyl]propionic acid methyl ester hydrochloride following the procedure described in Example 51.

δ (CDCl₃): 9.32 (s, 1H), 8.78 (d, 1H), 8.20 (d, 1H), 7.96 (d, 2H), 7.58 (m, 4H), 7.30 (m, 7H), 5.43 (d, 1H), 4.81 (m, 1H), 3.79 (s, 3H), 3.18 (m, 2H).

Example 72

(S)-3-[4-(2,6-Dichlorobenzoylamino)phenyl]-2-{3-[2-(toluene-4-sulfonyl)pyridin-3-yl]ureido}propionic
acid The title compound (75%) was prepared from the compound Example 71 by hydrolysis in a similar manner to Example 2.

m.p.: 180° C.

δ (DMSO-d6): 10.71 (s, 1H), 8.91 (s, 1H), 8.44 (d, 1H), 8.19 (s, 1H), 8.11 (m, 1H), 7.97 (m, 2H), 7.57 (m, 8H), 7.26 (d, 2H), 4.35 (m, 1H), 3.08 (m, 1H), 2.93 (m, 1H).

Example 73

(S)-2-{3-[2-(4-Chlorobenzenesulfonyl)pyridin-3-yl]
ureido}-3-[4-(2,6-dichlorobenzoylamino)phenyl]
propionic acid methyl ester The title compound is obtained as a white solid from 2-(4-Chlorobenzenesulfonyl)pyridin-3-ylamine and (S)-2-amino-3-[4-(2,6-dichlorobenzoylamino)phenyl]propionic acid methyl ester hydrochloride following the procedure described in Example 51.

δ (CDCl₃): 9.42 (s, 1H), 8.77 (d, 1H), 8.20 (d, 1H), 7.88 (d, 2H), 7.62 (d, 2H), 7.27 (m, 9H), 5.40 (d, 1H), 4.83 (m, 1H), 3.79 (s, 3H), 3.19 (m, 2H), 2.41 (s, 3H).

Example 74

(S)-2-{3-[2-(4-Chlorobenzenesulfonyl)pyridin-3-yl]
ureido}-3-[4-(2,6-dichlorobenzoylamino)phenyl]
propionic acid The title compound (84%) was prepared from the compound Example 73 by hydrolysis in a similar manner to Example 2.

m.p.: 181° C.

δ (DMSO-d6): 10.85 (s, 1H), 9.07 (s, 1H), 8.58 (d, 1H), 8.32 (s, 1H), 8.25 (s, 1H), 8.00 (d, 2H), 7.62 (m, 8H), 7.41 (d, 2H), 4.45 (m, 1H), 3.25 (m, 1H), 3.05 (m, 1H), 2.51 (s, 3H).

Example 75

(S)-3-[4-(2,6-Dichlorobenzoylamino)phenyl]-2-{3-methyl-3-[2-(piperidine-1-sulfonyl)phenyl]
ureido}propionic acid methyl ester Triphosgene (0.04 g, 0.13 mmol) was added at 0° C. to a solution of the compound of Preparation 4 (0.11 g, 0.42 mmol) in dichloromethane (2 ml) and diisopropylethylamine (0.16 g, 1.26 mmol. After 30 min stirring at 0° C. a solution of (S)-2-amino-3-[4-(2,6-dichlorobenzoylamino)phenyl]propionic acid methyl ester hydrochloride (0.17 g, 0.42 mmol) and diisopropylethylamine (0.22 g, 1.68 mmol) in dichloromethane (2 ml) was added. The reaction mixture was allowed to warm to room temperature and stirred overnight. The reaction mixture was diluted with ethyl acetate and washed with 5% citric acid (10 ml), water (10 ml) and brine (10 ml); dried with sodium sulphate filtered and evaporated under reduced pressure. The obtained crude oil was purified by flash chromatography (hexanes:ethyl acetate 1:3) to afford the title compound (0.11 g, 43%) as a white solid.

δ (CDCl$_3$): 8.32 (d, 1H), 7.95 (d, 1H), 7.55 (m, 4H), 7.38 (m, 4H), 6.93 (m, 3H), 4.63 (m, 1H), 4.42 (d, 1H), 3.72 (s, 3H), 3.15 (s, 3H), 3.10 (m, 6H), 1.60 (m, 4H), 1.22 (m, 2H).

Example 76

(S)-3-[4-(2,6-Dichlorobenzoylamino)phenyl]-2-{3-methyl-3-[2-(piperidine-1-sulfonyl)-phenyl]ureido}propionic acid The title compound (0.06 g, 55%) was prepared from the compound of Example 75 by hydrolysis in a similar manner to Example 2.

δ (DMSO-d6): 10.72 (s, 1H), 7.94 (d, 1H), 7.58 (m, 8H), 7.15 (m, 3H), 4.25 (s, 1H), 3.08 (s, 3H), 2.93 (m, 6H), 1.37 (m, 4H), 1.10 (m, 2H).

Example 77

(S)-3(4-{[1-(3,5-Dichloropyridin-4-yl)methanoyl]amino}phenyl)-2-{3-[3-(1-phenylmethanoyl)phenyl]ureido}propionic acid The title compound was obtained as a white solid from 1-(3-Aminophenyl)-1-phenylmethanone and (S)-2-Amino-3-{4-[(3,5-dichloropyridine-4-carbonyl)amino]phenyl}propionic acid methyl ester hydrochloride following the procedure described in Example 24.

δ (DMSO-d6): 10.95 (s, 1H), 9.00 (s, 1H), 8.80 (s, 2H), 7.70 (m, 10H), 7.25 (m, 3H), 6.50 (d, 1H), 4.50 (m, 1H), 3.00 (m, 2H).

Example 78

(S)-2-[3-(2-Benzylphenyl)-3-methylureido]-3-(4-{[1-(3,5-dichloropyridin-4-yl)methanoyl]amino}-phenyl)propionic acid methyl ester The title compound was obtained as a white solid from the compound of Preparation 11 and (S)-2-Amino-3-{4[(3,5-dichloropyridine-4-carbonyl)amino]phenyl}propionic acid methyl ester hydrochloride following the procedure described in Example 31.

δ (DMSO-d6): 10.79 (s, 1H), 8.74 (s, 2H), 7.44 (d, 2H), 7.32 to 6.82 (m, 12H), 4.36 (m, 1H), 3.68 (m, 2H), 3.56 (s, 3H), 2.84 (m, 2H), 2.72 (s, 3H).

Example 79

(S)-2-[3-(2-Benzylphenyl)-3-methylureido]-3-(4-{[1-(3,5-dichloropyridin-4-yl)methandyl]amino}-phenyl)propionic acid The title compound (14%) was prepared from the compound of Example 78 by hydrolysis in a similar manner to Example 2.

m.p.: 153° C.

δ (DMSO-d6): 10.89 (s, 1H), 8.80 (s; 2H), 7.52 (d, 2H), 7.29 to 7.02 (m, 12H), 4.30 (m, 1H), 3.76 (m, 2H), 2.95 (m, 2H), 2.81 (s, 3H).

Examples 80–86

These compounds were synthesized from compounds of the preparations 6, 7, 12, 13, 14, 15 and 16 and (S)-2-Amino-3-{4-[(3,5-dichloropyridine-4-carbonyl)amino]phenyl}propionic acid methyl ester hydrochloride, following the procedure as described in Example 31 and Example 32. The ESI/MS data, HPLC retention times and yields are summarized in table 2.

TABLE 2

| Example | R2 | Molecular Formula | ESI/MS m/e [M + H]$^+$ | Retention Time (min) | Yield (%) |
|---|---|---|---|---|---|
| 80 | H | C$_{30}$H$_{31}$Cl$_2$N$_5$O$_5$ | 613 | 16 | 30 |
| 81 | Me | C$_{31}$H$_{33}$Cl$_2$N$_5$O$_5$ | 627 | 16 | 21 |
| 82 | Pr | C$_{33}$H$_{37}$Cl$_2$N$_5$O$_5$ | 655 | 15 | 15 |
| 83 | cyclopropylmethyl | C$_{34}$H$_{37}$Cl$_2$N$_5$O$_5$ | 657 | 14.9 | 10 |
| 84 | Pn | C$_{35}$H$_{41}$Cl$_2$N$_5$O$_5$ | 683 | 10.6 | 20 |
| 85 | Bn | C$_{37}$H$_{37}$Cl$_2$N$_5$O$_5$ | 703 | 10.2 | 16 |
| 86 | cyclohexylmethyl | C$_{37}$H$_{43}$Cl$_2$N$_5$O$_5$ | 109 | 10.9 | 14 |

Example 87

(S)-3-(4-{[1-(3,5-Dichloropyridin-4-yl)methanoyl]amino}phenyl)-2-{3-methyl-3-[2-(piperidine-1-sulfonyl)phenyl]ureido}propionic acid methyl ester The title compound was obtained as a white solid from the compound of Preparation 4 and (S)-2-Amino-3-{4-[(3,5-dichloropyridine-4-carbonyl)amino]phenyl}-propionic acid methyl ester hydrochloride following the procedure described in Example 51.

δ (DMSO-d6): 10.92 (s, 1H), 8.82 (s, 2), 7.86 (d, 1H), 7.58 (m, 5H), 7.18 (m, 3H), 4.34 (m, 1H), 3.64 (s, 3H), 3.15 (s, 3H), 2.94 (m, 6H), 1.40 (m, 6H).

Example 88

(S)-3-(4-{[1-(3,5-Dichloropyridin-4-yl)methyanoyl]amino}phenyl)-2-{3-methyl-3-[2-(piperidine-1-sulfonyl)phenyl]ureido}propionic acid.

The title compound (20%) was prepared from the compound of Example 87 by hydrolysis in a similar manner to Example 2.

m.p.; 167° C.

δ (DMSO-d6): 10.88 (s, 1H), 8.80 (s, 2H), 7.86 (d, 1H), 7.58 (m, 5H), 7.16 (m, 3H), 4.24 (m, 1), 3.15 (s, 3H), 2.98 (m, 6H), 1.44 (m, 6H).

Example 89

(S)-3-(4-{[1-(3,5-Dichloropyridin-4-yl)methanoyl]
amino}phenyl)-2-{3-[2-(4-methylpiperazine-1-sulfo-
nyl)phenyl]ureido}propionic acid methyl ester The title compound was obtained as a white solid from the compound of Preparation 8 and (S)-2-Amino-3-{4-[(3,5-dichloropyridine-4-carbonyl)amino]phenyl}propionic acid methyl ester hydrochloride following the procedure described in Example 51.

δ (DMSO-d6): 10.94 (s, 1H), 8.82 (s, 2H), 8.38 (s, 1H), 8.05 (d, 1H), 7.86 (d, 1H), 7.64 (m, 4H), 7.22 (m, 3H), 4.42 (m, 1H), 3.64 (s, 3H), 2.95 (m, 6H), 2.26 (m, 4H), 2.12 (s, 3H).

Example 90

(S)-3-(4-{[1-(3,5-Dichloropyridin-4-yl)methanoyl]
amino}phenyl)-2-{3-[2-(4-methylpiperazine-1-sulfo-
nyl)phenyl]ureido}propionic acid The title compound (46%) was prepared from the compound of Example 89 by hydrolysis in a similar manner to Example 2.

m.p.: 189° C.

δ (DMSO-d6): 10.94 (s, 1H), 8.78 (s, 2H), 8.38 (s, 1H), 7.94 (d, 1H), 7.58 (m, 5H), 7.18 (m, 3H), 4.02 (m, 1H), 2.90 (m, 6H), 2.26 (m, 4H), 2.14 (s, 3H).

Example 91

(S)-2-[3-(2-Cyclopentanesulfonylphenyl)ureido]-3-
(4-{[1-(3,5-dichloropyridin-4-yl)methanoyl]
amino}phenyl)propionic acid methyl ester The title compound was obtained as a white solid from the compound of Preparation 17 and (S)-2-Amino-3-{4-[(3,5-dichloropyridine-4-carbonyl)amino]phenyl}propionic acid methyl ester hydrochloride following the procedure described in Example 51.

δ (DMSO-d6): 10.90 (s, 1H), 8.80 (s, 2H), 8.48 (s, 1H), 8.12 (d, 1H), 7.88 (d, 1H), 7.72 (d, 1H), 7.58 (m, 3H), 7.22 (m, 3H), 4.42 (m, 1H), 3.62 (s, 3H), 3.66 (m, 1H), 2.96 (m, 2H), 1.90 to 1.42 (m, 8H).

Example 92

(S)-2-[3-(2-Cyclopentanesulfonylphenyl)ureido]-3-
(4-{[1-(3,5-dichloropyridin-4-yl)methanoyl]
amino}phenyl)propionic acid The title compound (35%) was prepared from the compound of Example 91 by hydrolysis in a similar manner to Example 2.

m.p.: 233° C.

δ (DMSO-d6): 10.88 (s, 1H), 8.82 (s, 2H), 8.44 (s, 1H), 7.94 (d, 1H), 7.74 (d, 1H), 7.58 (m, 4H), 7.20 (m, 3H), 4.26 (m, 1H), 3.66 (m, 1H), 2.96 (m, 2H), 1.96 to 1.42 (m, 8H).

Example 93

(S)-3-(4-{[1-(3,5-Dichloropyridin-4-yl)methanoyl]
amino}phenyl)-2-{3-[2-(2-methylpropane-2-sulfo-
nyl)phenyl]ureido}propionic acid methyl ester The title compound was obtained as a white solid from the compound of Preparation 18 and (S)-2-Amino-3-{4-[(3,5-dichloropyridine-4-carbonyl)amino]phenyl}propionic acid methyl ester hydrochloride following the procedure described in Example 51.

δ (DMSO-d6): 10.82 (s, 1H), 8.74 (s, 2H), 8.68 (s, 1H), 8.18 (d, 1H), 7.84 (d, 1H), 7.56 (m, 4H), 7.18 (m, 3H), 4.38 (m, 1H), 3.58 (s, 3H), 2.94 (m, 2H).

Example 94

(S)-3-(4-{[1-(3,5-Dichloropyridin-4-yl)methanoyl]
amino}phenyl)-2-{3-[2-(2-methylpropane-2-sulfo-
nyl)phenyl]ureido}propionic acid The title compound (38%) was prepared from the compound of Example 93 by hydrolysis in a similar manner to Example 2.

m.p.: 228° C.

δ (DMSO-d6): 10.90 (s, 1H), 8.80 (s, 2H), 8.72 (s, 1H), 8.02 (d, 1H), 7.96 (m, 1H), 7.62 (m, 4H), 7.22 (m, 3H), 4.38 (m, 1H), 2.94 (m, 2H).

Example 95

(S)-3-(4-{[1-(3,5-Dichloropyridin-4-yl)methanoyl]
amino}phenyl)-2-{3-[2-(7-methylthieno[2,3-b]
pyrazin-3-ylsulfanyl)phenyl]ureido}propionic acid
methyl ester The title compound was obtained as a white solid from 2-(7-Methylthieno[2,3-b]pyrazin-3-ylsulfanyl)phenylamine and (S)-2-Amino-3-{4-[(3,5-dichloropyridine-4-carbonyl)amino]phenyl)propionic acid methyl ester hydrochloride following the procedure described in Example 51.

δ (DMSO-d6): 10.94 (s, 1H), 8.82 (s, 2H), 8.58 (s, 1H), 8.18 (m, 3H), 7.54 (m, 5H), 7.10 (m, 3H), 4.52 (m, 1H), 3.62 (s, 3H), 3.00 (m, 2H), 2.82 (s, 3H).

Example 96

(S)-3-(4-{[1-(3,5-Dichloropyridin-4-yl)methanoyl]
amino}phenyl)-2-(3-[2-(7-methylthieno[2,3-b]
pyrazin-3-ylsulfanyl)phenyl]ureido}propionic acid The title compound (60%) was prepared from the compound of Example 95 by hydrolysis in a similar manner to Example 2.

m.p.: 193° C.

δ (DMSO-d6): 10.94 (s, 1H), 8.81 (s, 2H), 8.58 (s, 1H), 8.16 (m, 3H), 7.56 (m, 4H), 7.20 (m, 4H), 4.42 (m, 1H), 2.94 (m, 2H), 2.78 (s, 3H).

Example 97

(S)-3-(4-{[1-(3,5-Dichloropyridin-4-yl)methanoyl]
amino}phenyl)-2-{3-[2-(3,5-dichloropyridin-4-ylsul-
fanyl)phenyl]ureido}propionic acid methyl ester The title compound was obtained as a white solid from 2-(3,5-Dichloropyridin-4-ylsulfanyl)phenylamine and (S)-

2-Amino-3-{4-[(3,5-dichloropyridine-4-carbonyl)amino]phenyl}propionic acid methyl ester hydrochloride following the procedure described in Example 51.

δ (DMSO-d6): 10.96 (s, 1H), 8.80 (s, 2H), 8.70 (s, 2H), 8.52 (s, 1H), 7.72 (d, 1H), 7.60 (d, 2H), 7.24 (m, 4H), 6.92 (m, 2H), 4.54 (m, 1H), 3.68 (s, 3H), 3.00 (m, 2H).

Example 98

(S)-3-(4-{[1-(3,5-Dichloropyridin-4-yl)methanoyl]amino}phenyl)-2-{3-[2-(3,5-dichloropyridin-4-ylsulfanyl)phenyl]ureido}propionic acid The title compound (40%) was prepared from the compound of Example 97 by hydrolysis; in a similar manner to Example 2.

m.p.: 211° C.

δ (DMSO-d6): 10.94 (s, 1H), 8.78 (s, 2H), 8.64 (s, 2H), 8.50 (s, 1H), 7.70 (d, 1H), 7.58 (d, 2H), 7.18 (m, 4H), 6.86 (m, 2H), 4.46 (m, 1H), 3.02 (m, 2H).

Example 99

(S)-3-(4-{[1-(3,5- Dichloropyridin-4-yl)methanoyl]amino}phenyl)-2-{3-[2-(piperidine-1-sulfonyl)phenyl]ureido}propionic acid methyl ester The title compound was obtained as a white solid from the compound of Preparation 3 and the compound of Preparation 19 following the procedure described in Example 51.

δ (DMSO-d6): 8.46 (s, 1H), 8.82 (d, 2H), 8.54 (d, 1H), 8.42 (s, 1H), 8.12 (d, 1H), 7.89 (d, 1H), 7.58 (m, 5H), 7.25 (m, 3H), 4.45 (m, 1H), 3.64 (s, 3H), 3.00 (m, 6H), 1.40 (m, 6H).

Example 100

(S)-3-(4-{[1-(3,5-Dichloropyridin-4-yl)methanoyl]amino}phenyl)-2-{3-[2-piperidine-1-sulfonyl)phenyl]ureido}propionic acid The title compound (23%) was prepared from the compound of Example 99 by hydrolysis in a similar manner to Example 2.

m.p.: >300° C.

δ (DMSO-d6): 11.32 (s, 1H), 9.00 (s, 1H), 8.78 (s, 1H), 8.62 (bs, 1H), 8.52 (d, 1H), 8.40 (s, 1H), 8.02 (d, 2H), 7.72 (d, 2H), 7.58 (m, 3H), 7.14 (m, 3H), 4.05 (m, 1H), 3.00 (m, 6H), 1.38 (m, 6H).

Example 101

(S)-3-(4-{[1-(3,5-Dichloropyridin-4-yl)methanoyl]amino}phenyl)-2-{3-methyl-3-[2-(piperazine-1-sulfonyl)phenyl]ureido}propionic acid methyl ester A mixture of compound from Preparation 10 (0.24 g, 0.62 mmol) and diphosgene (0.061 g, 0.31 mmol) in dioxane (2 ml) was heated at 60° C. for 16 h. The solvent was removed under reduced pressure. The crude isocyanate was slowly added to a solution of (S)-2-Amino-3-{4-[(3,5-dichloropyridine-4-carbonyl)amino]phenyl}propionic acid methyl hydrochloride (0.25 g, 0.63 mmol) and triethylamine (0.063 g, 0.63 mmol) in dichloromethane (2 ml) and the resulting reaction mixture was stirred at room temperature overnight. The precipitate obtained was collected by filtration, washed several times with dichloromethane and dried under vacuum. The resulting solid was treated with a saturated solution of hydrogen chloride in dioxane (2 ml) for 2 h at room temperature. The solvent was removed under reduced pressure to yield the title compound (0.1 g, 25%) as a white solid.

δ (DMSO-d6): 10.82 (s, 1H), 8.78 (s, 2H), 7.45 (m, 4H), 7.16 (d, 2H), 6.90 (d, 1H), 6.64 (m, 2H), 6.25 (m, 1H), 4.18 (m, 1H), 3.45 (s, 3H), 3.23 (m, 4H), 2.78 (m, 9H).

Example 102

(S)-3-(4-{[1-(3,5-Dichlaropyridin-4-yl)methanoyl]amino}phenyl)-2-{3-methyl-3-[2-(piperazine-1-sulfonyl)phenyl]ureido}propionic acid The title compound (10%) was prepared from the compound of Example 101 by hydrolysis in a similar manner to Example 2.

m.p.: 171° C.

δ (DMSO-d6): 10.78 (s, 1H), 8.78 (s, 2H), 7.44 (m, 4H), 6.98 (d, 2H), 6.74 (m, 2H), 6.28 (m, 1H), 6.10 (d, 1H), 3.80 (m, 1H), 3.25 (m, 4H), 2.74 (m, 9H).

Example 103

(S)-2-[3-(2-Benzenesulfonylphenyl)ureido]-3-(4-{[1-(2-chloro-6-methylpyridin-3-yl)methanoyl]amino}phenyl)propionic acid To a suspension of 2-chloro-6-methylnicotinic acid (75 mg, 0.44 mmol) in dichloromethane (1.5 ml) oxalyl chloride (42 µl, 0.484 mmol) and a drop of DMF were added and the resulting solution was stirred at room temperature for 4 h. The volatiles were removed under vacuum to give a solid that was dissolved in dichloromethane (2 ml). This solution was slowly added to a stirred solution of the amine from Preparation 20 (200 mg, 0.44 mmol), Et₃N (0.18 ml, 1.32 mmol) and a catalytic amount of 4-DMAP in dichloromethane (3 ml) and the reaction mixture was stirred overnight at room temperature. The reaction mixture was then diluted with dichloromethane (50 ml) and washed with saturated aqueous NaHCO₃ (2×30 ml) and brine (30 ml). The organic layer was dried (MgSO₄) and concentrated under reduced pressure. The residue was purified by flash chromatography (8:2 to 7:3 DCM/EtOAc) to yield (S)-2-[3-(2-benzenesulfonylphenyl)ureido]-3-(4-{[1-(2-chloro-6-methylpyridin-3-yl)methanoylamino}phenyl)propionic acid methyl ester (147 mg, 55%).

A solution of the solid above (147 mg, 0.242 mmol) and LiOH (7.0 mg, 0.30 mmol) in tetrahydrofuran (2.5 ml) and H₂O (2.5 ml) was stirred at room temperature for 2 h. The organic solvent was removed under reduced pressure and the resulting aqueous solution was acidified with acetic acid until pH 4. The precipitate was collected by filtration to obtain the title compound (120 mg, 84%).

m.p.: 210° C.

δ (DMSO-d6): 12.85 (bs, 1H), 10.57 (s, 1H), 8.50 (s, 1H), 8.08 (d, 1H), 7.92 (m, 4H), 7.84 (d, 1H), 7.59 (m, 6H), 7.41 (d, 1H), 7.26 (m, 3H), 4.30 (m, 1H), 3.07 (m, 1H), 2.86 (m, 1H), 2.52 (s, 3H).

Example 104

(S)-2-[3-(2-Benzenesulfonylphenyl)ureido]-3-(4-{[1-(2,6-dichloropyridin-3-yl)-methanoyl]amino}phenyl)propionic acid The title compound (37%) was prepared from 2,6-dichloronicotinic acid and the amine from Preparation 20 in a similar manner to Example 103.

m.p.: 207° C.

δ (DMSO-d6): 12.90 (bs, 1H), 10.67 (s, 1H), 8.49 (s, 1H), 8.17 (d, 1H), 8.05 (d, 1H), 7.95 (m, 4H), 7.84 (d, 1H), 7.73 (d, 1H), 7.62 (m, 3H), 7.53 (m, 3H), 7.24 (m, 3H), 4.28 (m, 1H), 3.06 (dd, 1H), 2.87 (dd, 1H).

Example 105

(S)-2-[3-(2-Benzenesulfonylphenyl)ureido]-3-(4-{[1-(3,5-dimethoxypyridin-4-yl)-methanoyl]amino}phenyl)propionic acid The title compound (39%) was prepared from the acid of Preparation 22 and the amine from Preparation 20 following the procedure described in Example 103.

m.p.: 196° C.

δ (DMSO-d6): 12.80 (bs, 1H), 10.41 (s, 1H), 8.48 (s, 1H). 8.21 (s, 2H), 7.92 (m, 4H), 7.85 (d, 1H), 7.61 (m, 6H), 7.23 (m, 3H), 4.29 (m, 1H), 3.88 (s, 6H), 3.06 (m, 1H), 2.82 (m, 1H).

Example 106

(S)-2-[3-(2-Benzenesulfonylphenyl)ureido]-3-(4-{[1-(3,5-dibromopyridin-4-yl)-methanoyl]amino}phenyl)propionic acid The title compound was prepared from 3,5-dibromoisonicotinic acid (prepared according to the method of Gu, Y. G. and Bayburt, E. K. Tetrahedron Lett., 1996, 37, 2565) and the amine from Preparation 20 following the procedure described in Example 103.

m.p.: 231° C.

δ (DMSO-d6): 12.90 (bs, 1H), 10.87 (s, 1H), 8.88 (s, 2H), 8.49 (s, 1H), 8.08 (d, 1H), 7.92 (m, 3H), 7.85 (d, 1H), 7.59 (m, 6H), 7.30 (m, 3H), 4.31 (m, 1H), 3.05 (m, 1H), 2.87 (m, 1H).

Example 107

(S)-2-[3-(2-Benzenesulfonylphenyl)ureido]-3-[4-(2,6-dichlorobenzylamino)phenyl]propionic acid methyl ester A solution of 2,6-dichlorobenzaldehyde (112 mg, 0.64 mmol) and the amine from Preparation 20 (300 mg, 0.66 mmol) in EtOH (2 ml) was heated at 50° C. for 1 h. The reaction mixture was then cooled to 0° C. and NaBH$_3$CN (166 mg, 2.64 mmol) was added. The reaction mixture was stirred at room temperature for 2 h before being partitioned between DCM (50 ml) and saturated aqueous NaHCO$_3$ (30 ml). The organic layer was separated, washed with saturated aqueous NaHCO$_3$ (2×30 ml) and brine (30 ml) and dried (MgSO$_4$). The solvent was removed in vacuo and the residue purified by flash chromatography (4:1 to 1:1 hexanes/EtOAc) to give the title compound (280 mg, 71%).

δ (CDCl3): 8.70 (d, 1H), 8.04 (d, 1H), 7.98 (d, 1H), 7.81 (d, 2H), 7.46 (m, 5H), 7.20 (m, 4H), 6.98 (d, 2H), 6.75 (d, 2H), 5.23 (d, 1H), 4.68 (m, 1H), 4.58 (s, 2H), 3.77 (s, 3H), 3.02 (m, 2H).

Example 108

(S)-2-[3-(2-Benzenesulfonylphenyl)ureido]-3-[4-(2,6-dichlorobenzylamino)phenyl]propionic acid The title compound (78%) was prepared from the compound of Example 107 by hydrolysis following the procedure described in Example 2.

m.p.: 116° C.

δ (DMSO-d6): 12.72 (bs, 1H), 8.47 (s, 1H), 7.94 (m, 4H), 7.81 (d, 1H), 7.52 (m, 6H), 7.39 (m, 1H), 7.21 (t, 1H), 7.03 (d, 2H), 6.66 (d, 2H), 5.67 (m, 1H), 4.37 (d, 2), 4.18 (m, 1H), 2.94 (dd, 1H), 2.71 (dd, 1H).

Example 109

(S)-2-[3-(2-Benzenesulfonylphenyl)ureido]-3-{4-[(3,5-dichloropyridin-4-ylmethyl)amino]phenyl}propionic acid methyl ester The title compound (50%) was prepared from 3,5-dichloropyridine-4-carboxaldehyde (prepared according to the method of Stewart A. O. et al WO99/62908) and the amine from Preparation 20 following the procedure described in Example 107.

δ (CDCl3): 8.78 (s, 1H), 8.46 (s, 2H), 8.08 (d, 1H), 7.96 (d, 1H), 7.83 (d, 2H), 7.45 (m, 4H), 7.22 (d, 1H), 7.16 (t, 1H), 7.00 (d, 2H), 6.69 (d, 2H), 5.22 (d, 1H), 4.71 (m, 1H), 4.59 (s, 2H), 3.76 (s, 3H), 3.01 (d, 2H).

Example 110

(S)-2-[3-(2-Benzenesulfonylphenyl)ureido]-3-{4-[(3,5-dichloropyridin-4-ylmethyl)amino]phenyl}propionic acid The title compound (80%) was prepared from the compound of Example 109 by hydrolysis following the procedure described in Example 2.

m.p.: 194° C.

δ (DMSO-d6): 12.75 (bs, 1H), 8.64 (s, 2H), 8.47 (s, 1H), 7.97 (m, 4H), 7.81 (d, 1H), 7.52 (m, 4H), 7.21 (t, 1H), 7.04 (d, 2H), 6.64 (d, 2H), 5.90 (t, 1H), 4.39 (d, 2H), 4.18 (m, 1H), 2.96 (m, 1H.), 2.73 (m, 1H).

Example 111

(S)-2-[3-(2-Benzenesulfonylphenyl)ureido]-3-(4-dimethylcarbamoyloxyphenyl) propionic acid methyl ester A solution of compound from Preparation 21 (300 mg, 0.66 mmol), dimethylcarbamyl chloride (0.12 ml, 1.32 mmol) and a catalytic amount of 4-DMAP in pyridine (1 ml) was heated overnight at 70° C. The solvent was removed in vacuo and the residue was dissolved in dichloromethane (40 ml), washed with saturated aqueous NaHCO$_3$ (3×30 ml) and dried (MgSO$_4$). The solvent was removed under reduced pressure and the resulting crude was purified by flash chromatography (1:1 to 3:7 hexanes/EtOAc) to give the title compound (281 mg, 81%) as an oil.

δ (CDCl3): 8.72 (s, 1H), 8.07 (d, 1H), 7.96 (d, 1H), 7.82 (d, 2H), 7.50 (m, 4H), 7.10 (m, 5H), 5.50 (d, 1H), 4.79 (m, 1H), 3.74 (s, 3H), 3.07 (bs, 5H), 2.97 (s, 3H).

Example 112

(S)-2-[3-(2-Benzenesulfonylphenyl)ureido]-3-(4-dimethylcarbamoyloxyphenyl) propionic acid The title compound (77%) was prepared from the compound of Example 111 by hydrolysis following the procedure described in Example 2.

m.p.: 115° C.

δ (DMSO-d6): 12.86 (bs, 1H), 8.49 (s, 1H), 8.08 (d, 1H), 8.00 (d, 1H), 7.97 (d, 2H), 7.82 (d, 1H), 7.66 (m, 1H), 7.48 (m, 3H), 7.28 (d, 2H), 7.20 (m, 1H), 7.07 (d, 2H), 4.31 (m, 1H), 3.07 (m, 1H), 3.04 (s, 3H), 2.91 (s, 3H), 2.88 (m, 1H).

Example 113

4-Methylpiperazine-1-carboxylic acid 4-{(S)-2-[3-(2-benzenesulfonylphenyl)ureido]-2-methoxycarbonylethyl}phenyl ester The title compound (83%) was prepared from 4-methyl-1-piperazinecarbonyl chloride hydrochloride and the compound from Preparation 21 following the procedure described in Example 111.

δ (CDCl3): 8.71 (s, 1H), 8.07 (s, 1H), 7.98 (s, 1H), 7.83 (d, 2H), 7.50 (m, 4H), 7.10 (m, 5H), 5.55 (d, 1H), 4.79 (m, 1H), 3.79 (s, 3H), 3.70 (bs, 4H), 3.12 (m, 2H), 2.60 (bs, 4H), 2.42 (s, 3H).

Example 114

4-Methylpiperazine-1-carboxylic acid 4-{(S)-2-[3-(2-benzenesulfonylphenyl)ureido]-2-carboxyethyl}phenyl ester The title compound (42%) was prepared from the compound of Example 113 by hydrolysis following the procedure described in Example 2.

m.p.: 160° C.

δ (DMSO-d6): 8.46 (s, 1H), 8.06 (d, 1H), 7.89 (m, 3H), 7.79 (d, 1H), 7.62 (d, 1H), 7.48 (m, 3H), 7.23 (m, 3H), 7.05 (m, 2H), 4.28 (m, 1H), 3.55 (m, 2H), 3.41 (m, 2H), 3.05 (m, 1H), 2.87 (m, 1H), 2.39 (bs, 4H), 2.22 (s, 3H).

Example 115

3,5-Dichloroisonicotinic acid 4-{(S)-2-[3-(2-benzenesulfonylphenyl)ureido]-2-methoxycarbonylethyl}phenyl ester The title compound (82%) was prepared from 3,5-dichloroisonicotinoyl chloride and the compound from Preparation 21 following the procedure described in Example 111.

δ (CDCl3): 8.82 (s, 1H), 8.63 (s, 2H), 8.08 (d, 1H), 7.96 (d, 1H), 7.82 (d, 2H), 7.50 (m, 4H), 7.20 (m, 5H), 5.43 (d, 1H), 4.81 (m, 1H), 3.78 (s, 3H), 3.18 (m, 2H).

Example 116

3,5-Dichloroisonicotinic acid 4-{(S)-2-[3-(2-benzenesulfonylphenyl)ureido]-2-carboxyethyl}phenyl ester The title compound (44%) was prepared from the compound of Example 115 by hydrolysis following the procedure described in Example 2.

m.p.: 186° C.

δ (DMSO-d6): 8.91 (s, 2H), 8.50 (s, 1H), 7.96 (m, 4H), 7.83 (d, 1H), 7.54 (m, 6H), 7.28 (m, 3H), 4.31 (m, 1H), 3.16 (m, 1H), 2.93 (m, 1H).

Example 117

(S)-3-(2'-Cyanobiphenyl-4-yl)-2-{3-[2-(piperdine-1-sulfonyl)phenyl]ureido}propionic acid methyl ester A solution of the compound from Preparation 3 (72 mg, 0.30 mmol) and diphosgene (18 μl, 0.15 mmol) in dioxane (1 ml) was heated at 60° C. for 16 h. The solvent was removed under reduced pressure. The crude isocyanate was dissolved in dichloromethane (1 ml) and this solution was slowly added to a solution of the compound from Preparation 23 (95 mg, 0.30 mmol) and triethylamine (0.10 ml, 0.7 mmol) in dichloromethane (1 ml) and the resulting reaction mixture was stirred at room temperature overnight. The reaction mixture was partitioned between dichloromethane (25 ml) and saturated aqueous $NaHCO_3$ (20 ml). The organic layer was separated and washed with saturated aqueous $NaHCO_3$ (2×20 ml) and brine (20 ml). The solvent was removed under vacuum and the residue purified by flash chromatography (8:2 to 6:4 hexanes/EtOAc) to yield the title compound (129 mg, 79%).

δ (CDCl3): 8.70 (s, 1H), 8.18 (d, 1H), 7.70 (m, 3H), 7.50 (m, 5H), 7.30 (d, 2H), 7.14 (t, 1H), 5.38 (d, 1H), 4.84 (m, 1H), 3.78 (s, 3H), 3.20 (m, 2H), 3.02 (m, 4H), 1.63 (m, 4H), 1.44 (m, 2H).

Example 118

(S)-3-(2'-Cyanobiphenyl-4-yl)-2-{3-[2-(piperidine-1-sulfonyl)phenyl]ureido}propionic acid The title compound (80%) was prepared from the compound of Example 117 by hydrolysis following the procedure described in Example 2.

m.p.: 140° C.

δ (DMSO-d6): 12.95 (bs, 1H), 8.43 (d, 1H), 8.01 (d, 1H), 7.95 (m, 2H), 7.79 (t, 1H), 7.60 (m, 6H), 7.44 (m, 2H), 7.16 (t, 1H), 4.43 (m, 1H), 3.21 (m, 2H), 2.94 (m, 4H), 1.42 (m, 4H), 1.30 (m, 2H).

Example 119

(S)-3-(2'-Methoxybiphenyl-4-yl)-2-{3-[2-(piperidine-1-sulfonyl)phenyl]ureido}propionic acid methyl ester The title compound (34%) was prepared from the compound from Preparation 24 following the procedure described in Example 117.

δ (CDCl3): 8.63 (s, 1H), 8.17 (d, 1H), 7.68 (d, 1H), 7.50 (m, 3H), 7.30 (m, 2H), 7.10 (m, 5H), 5.25 (d, 1H), 4.83 (m, 1H), 3.81 (s, 3H), 3.77 (s, 3H), 3.20 (m, 2H), 2.98 (m, 4H), 1.60 (m, 4H), 1.40 (m, 2H).

Example 120

(S)-3-(2'-Methoxybiphenyl-4-yl)-2-{3-[2-piperidine-1-sulfonyl)phenyl]ureido}propionic acid The title compound (82%) was prepared from the compound of Example 119 by hydrolysis following the procedure described in Example 2.

m.p.: 177° C.

δ (DMSO-d6): 12.89 (bs, 1H), 8.43 (s, 1H), 7.94 (m, 2H), 7.64 (d, 1H), 7.54 (t, 1H), 7.34 (m, 2H), 7.25 (m, 4H), 7.18 (m, 2H), 7.01 (t, 1H), 4.38 (m, 1H), 3.74 (s, 3H), 3.35 (bs, 4H), 3.11 (m, 1H), 2.83 (m, 1H), 1.43 (bs, 4H), 1.32 (bs, 2H).

Example 121

(S)-2-[3-(2-Benzenesulfonylphenyl)ureido]-3-[4-([2,6]naphthyridin-1-ylamino)phenyl]propionic acid methyl ester The title compound (73%) was prepared from the compound from Preparation 25 and 2-benzenesulfonylphenylisocyanate (prepared as described in Preparation 20) following the procedure described in Example 117.

δ (CDCl3): 9.18 (s, 1H), 8.81 (s, 1H), 8.64 (d, 1H), 8.18 (m, 2H), 7.94 (d, 1H), 7.85 (d, 2H), 7.68 (m, 3H), 7.50 (m, 4H), 7.20 (m, 5H), 5.61 (d, 1H), 4.85 (m, 1H), 3.78 (s, 3H), 3.16 (m, 2H).

Example 122

(S)-2-[3-(2-Benzenesulfonylphenyl)ureido]-3-[4-([2,6]naphthyridin-1-ylamino)phenyl]propionic acid The title compound (89%) was prepared from the compound of Example 121 by hydrolysis following the procedure described in Example 2.

m.p.: 192° C.

δ (DMSO-d6): 12.85 (bs, 1H), 9.37 (s, 1H), 9.24 (s, 1H), 8.69 (d, 1H), 8.53 (s, 1H), 8.42 (d, 1H), 8.12 (m, 2H), 7.98 (m, 3H), 7.87 (m, 3H), 7.58 (m, 4H), 7.30 (m, 4H), 4.33 (m, 1H), 3.08 (dd, 1H), 2.88 (dd, 1H).

Example 123

(S)-3-[4-([2,6]Naphthyridin-1-ylamino)phenyl]-2-{3-[2-(piperidine-1-sulfonyl)phenyl]ureido}propionic acid methyl ester The title compound (57%) was prepared from the compound from Preparation 25 and 2-(piperidine-1-sulfonyl)phenylisocyanate following the procedure described in Example 117.

δ (CDCl3): 9.35 (s, 1H), 9.22 (s, 1H), 8.70 (d, 1H), 8.42 (m, 2H), 8.10 (m, 2H), 7.98 (d, 1H), 7.86 (d, 2H), 7.65 (d, 1H), 7.59 (t, 1H), 7.20 (m, 4H), 4.44 (m, 1H), 3.67 (s, 3H), 2.95 (m, 6H), 1.42 (m, 3H), 1.30 (m, 3H).

Example 124

(S)-3-[4-([2,6]Naphthyridin-1-ylamino)phenyl]-2-{3-[2-(piperidine-1-sulfonyl)phenyl]ureido}propionic acid The title compound (87%) was prepared from. the compound of Example 123 by hydrolysis following the procedure described in Example 2.

m.p.: 207° C.

δ (DMSO-d6): 9.33 (s, 1H), 9.22 (s, 1H), 8.67 (d, 1H), 8.43 (m, 2H), 8.14 (d, 1H), 7.93 (m, 2H), 7.83 (m, 2H), 7.65 (d, 1H), 7.54 (t, 1H), 7.30 (m, 3H), 7.15 (t, 1H), 4.35 (m, 1H), 3.08 (dd, 1H), 2.95 (m, 5H), 1.45 (m, 3H), 1.26 (m, 3H).

Example 125

(S)-2-[3-(2-Benzylphenyl)-3-methylureido]-3-[4-([2,6]naphthyridin-1-ylamino)phenyl]propionic acid methyl ester A solution of the compound from Preparation 11 (123 mg, 0.622 mmol) and diphosgene (38 μl, 0.311 mmol) in dioxane (2 ml) was heated at 60° C. for 16 h. The solvent was removed under reduced pressure. The crude was dissolved in ACN (2 ml), added to a solution of compound from Preparation 25 (182 mg, 0.566 mmol) and triethylamine (196 μl, 1.42 mmol) in ACN (2 ml) and the resulting reaction mixture was heated at 70° C. for 3 h. The reaction was concentrated in vacuo and the residue was purified by flash chromatography (30% to 100% EtOAc/hexanes) to give the title compound (48 mg, 16%).

δ (DMSO-d6): 9.19 (s, 1H), 8.63 (d, 1H), 8.22 (m, 1H), 7.69 (d, 1H), 7.58 (t, 2H), 7.21 (m, 11H), 6.93 (t, 2H), 4.68 (m, 1H), 4.49 (d, 1H), 3.93 (m, 1H), 3.72 (m, 1H), 3.70 (s, 3H), 2.95 (s, 3H), 2.85 (m, 2H).

Example 126

(S)-2-[3-(2-Benzylphenyl)-3-methylureido]-3-[4-([2,6]naphthyridin-1-ylamino)phenyl]propionic acid The title compound (72%) was prepared from the compound of Example 125 by hydrolysis following the procedure described in Example 2.

m.p.: 141° C.

δ (DMSO-d6): 12.85 (bs, 1H), 9.31 (s, 1H), 9.24 (s, 1H), 8.68 (d, 1H), 8.40 (d, 1H), 8.15 (d, 1H), 7.75 (m, 2H), 7.21 (m, 12H), 5.24 (m, 1H), 4.29 (m, 1H), 3.75 (m, 2H), 3.00 (m, 2H), 2.83 (s, 3H).

Example 127

(S)-2-[3-(2-Benzenesulfonylphenyl)ureido]-3-[4-([2,7]naphthyridin-1-ylamino)phenyl]propionic acid methyl ester The title compound (86%) was prepared from the compound from Preparation 26 and 2-benzenesulfonylphenylisocyanate (prepared as described in Preparation 20) following the procedure described in Example 117.

δ (CDCl3): 9.83 (s, 1H), 9.58 (d, 1H), 8.66 (d, 1H), 8.52 (s, 1H), 8.21 (m, 2H), 7.91 (m, 6H), 7.72 (d, 1H), 7.60 (m, 4H), 7.27 (m, 3H), 7.15 (d, 1H), 4.39 (m, 1H), 3.65 (s, 3H), 3.00 (m, 2H).

Example 128

(S)-2-[3-(2-Benzenesulfonylphenyl)ureido]-3-[4-([2,7]naphthyridin-1-ylamino)phenyl]propionic acid The title compound (84%) was prepared from the compound of Example 127 by hydrolysis following the procedure described in Example 2.

m.p.: 184° C.

δ (DMSO-d6): 9.85 (s, 1H), 9.59 (s, 1H), 8.66 (d, 1H), 8.53 (s, 1H), 8.17 (d, 1H), 8:09 (d, 1H), 7.98 (m, 3H), 7.84 (m, 3H), 7.69 (d, 1H), 7.58 (m, 4H), 7.27 (m, 3H), 7.13 (d, 1H), 4.32 (m, 1H), 3.08 (m, 1H), 2.88 (m, 1H).

Example 129

(S)-3-[4-([2,7]Naphthyridin-1-ylamino)-phenyl]-2-{3-[2-(piperidine-1-sulfonyl)phenyl]ureido}propionic acid methyl ester The title compound (78%) was prepared from the compound from Preparation 25 and 2-(piperidine-1-sulfonyl) following the procedure described in Example 117.

δ (CDCl3): 9.97 (s, 1H), 8.65 (s, 1H), 8.60 (d, 1H), 8.28 (d, 1H), 8.17 (d, 1H), 7.77 (d, 2H), 7.70 (d, 1H), 7.60 (d, 1H), 7.51 (t, 1H), 7.22 (m, 3H), 7.17 (d, 1H), 7.08 (d, 1H), 5.65 (d, 1H), 4.82 (d, 1H), 3.78 (s, 3H), 3.17 (m, 2H), 2.95 (m, 4H), 1.60 (m, 3H), 1.32 (m, 3H).

Example 130

(S)-3-[4-([2,7]Naphthyridin-1ylamino)-phenyl]-2-{3-[2-(piperidine-1-sulfonyl)phenyl]ureido}propionic acid The title compound (90%) was prepared from the compound of Example 129 by hydrolysis following the procedure described in Example 2.

m.p.: 179° C.

δ (DMSO-d6): 9.83 (s, 1H), 9.56 (s, 1H), 8.65 (d, 1H), 8.44 (s, 1H), 8.16 (d, 1H), 7.93 (m, 2H), 7.76 (m, 2H), 7.66 (m, 2H), 7.54 (t, 1H), 7.24 (d, 2H), 7.14 (m, 2H), 4.34 (m, 1H), 3.11 (m, 1H), 2.93 (m, 5H), 1.45 (m, 4H), 1.30 (m, 2H).

Example 131

(S)-2-[3-(2-Benzylphenyl)-3-methylureido]-3-[4-([2,7]naphthyridin-1-ylamino)phenyl]propionic acid methyl ester The title compound (14%) was prepared from the compound from Preparation 26 following the procedure described in Example 125.

δ (CDCl3): 9.42 (s, 1H), 8.63 (d, 1H), 8.21 (m, 1H), 7.55 (m, 4H), 7.20 (m, 10H), 6.90 (t, 2H), 4.68 (m, 1H), 4.49 (d, 1H), 3.92 (m, 1H), 3.72 (m, 1H), 3.71 (s, 3H), 2.97 (s, 3H), 2.90 (m, 2H).

Example 132

(S)-2-[3-(2-Benzylphenyl)-3-methylureido]-3-[4-([2,7]naphthyridin-1-ylamino)phenyl]propionic acid The title compound (72%) was prepared from the compound of Example 131 by hydrolysis following the procedure described in Example 2.

m.p.: 157° C.

δ (DMSO-d6): 12.73 (bs, 1H), 9.84 (s, 1H), 9.54 (s, 1H), 8.66 (d, 1H), 8.17 (d, 1H), 7.69 (m, 3H), 7.10 (m, 12H), 5.29 (m, 1H), 4.34 (m, 1H), 3.71 (m, 1H), 3.54 (m, 1H), 2.94 (m, 2H), 2.85 (s, 3H).

Example 133

(S)-2-[3-(2-Benzenesulfonylphenyl)ureido]-3-[4-([2,6]naphthyridin-1-yloxy)phenyl]propionic acid methyl ester The title compound (98%) was prepared from the compound from Preparation 27 and 2-benzenesulfonylphenylisocyanate (prepared as described in Preparation 20) following the procedure described in Example 117.

δ (CDCl3): 9.28 (s, 1H), 8.78 (m, 2H), 8.13 (m, 3H), 7.98 (d, 1H), 7.83 (d, 2H), 7.50 (m, 5H), 7.23 (m, 4H), 7.12 (t, 1H), 5.70 (d, 1H), 4.85 (m, 1H), 3.79 (s, 3H), 3.20 (d, 2H).

Example 134

(S)-2-[3-(2-Benzenesulfonylphenyl)ureido]-3-[4-([2,6]naphthyridin-1-yloxy)phenyl]propionic acid The title compound (95%) was prepared from the compound of Example 133 by hydrolysis following the procedure described in Example 2.

m.p.: 136° C.

δ (DMSO-d6): 9.44 (s, 1H), 8.78 (d, 1H), 8.53 (s, 1H), 8.11 (m, 3H), 7.98 (m, 3H), 7.86 (d, 1H), 7.60 (m, 5H), 7.41 (m, 2H), 7.27 (m, 3H), 4.33 (m, 1H), 3.19 (m, 1H), 2.92 (m, 1H).

Example 135

(S)-3-[4-([2,6]Naphthyridin-1-yloxy)phenyl]-2-{3-[2-(piperidine-1-sulfonyl)phenyl]ureido}propionic acid methyl ester The title compound (91%) was prepared from the compound from Preparation 27 and 2-(piperidine-1-sulfonyl) phenylisocyanate following the procedure described in Example 117.

δ (CDCl3): 9.29 (s, 1H), 8.78 (d, 1H), 8.64 (s, 1H), 8.19 (m, 2H), 8.05 (d, 1H), 7.68 (d, 1H), 7.50 (t, 1H), 7.43 (d, 1H), 7.22 (m, 5H), 5.63 (d, 1H), 4.89 (m, 1H), 3.79 (s, 3H), 3.20 (d, 2H), 2.99 (m, 4H), 1.60 (m, 4H), 1.40 (m, 2H).

Example 136

(S)-3-[4-([2,6]Naphthyridin-1-yloxy)phenyl]-2-{3-[2-(piperidine-1-sulfonyl)phenyl]ureido}propionic acid The title compound (90%) was prepared from the compound of Example 135 by hydrolysis following the procedure described in Example 2.

m.p.: 140° C.

δ (DMSO-d6): 12.80 (bs, 1H), 9.44 (s, 1H), 8.78 (d, 1H), 8.45 (s, 1H), 8.16 (d, 1H), 8.10 (d, 1H), 7.95 (m, 2H), 7.68 (m, 2H), 7.56 (t, 1H), 7.36 (m, 2H), 7.10 (m, 3H), 4.40 (m, 1H), 3.14 (m, 1H), 2.94 (m, 5H), 1.46 (m, 4H), 1.32 (m, 2H).

Example 137

(S)-2-[3-(2-Benzenesulfonylphenyl)ureido]-3-[4-([2,7]naphthyridin-1-yloxy)phenyl]propionic acid methyl ester The title compound (98%) was prepared from the compound from Preparation 28 and 2-benzenesulfonylphenylisocyanate (prepared as described in Preparation 20) following the procedure described in Example 117.

δ (CDCl3): 9.84 (s, 1H), 8.80 (s, 2H), 8.18 (m, 2H), 7.99 (d, 1H), 7.87 (d, 2H), 7.72 (d, 1H), 7.50 (m, 4H), 7.23 (m, 5H), 7.17 (t, 1H), 5.68 (d, 1H), 4.83 (m, 1H), 3.79 (s, 3H), 3.20 (d, 2H).

Example 138

(S)-2-[3-(2-Benzenesulfonylphenyl)ureido]-3-[4-([2,7]naphthyridin-1-yloxy)phenyl]propionic acid The title compound (85%) was prepared from the compound of Example 137 by hydrolysis following the procedure described in Example 2.

m.p.: 164° C.

δ (DMSO-d6): 9.71 (s, 1H), 8.82 (d, 1H), 8.54 (s, 1H), 8.13 (d, 2H), 7.97 (m, 3H), 7.87 (m, 2H), 7.64 (m, 1H), 7.59 (m, 4H), 7.41 (d, 2H), 7.28 (d, 2H), 7.23 (t, 1H), 4.35 (m, 1H), 3.17 (m, 1H), 2.94 (m, 1H).

Example 139

(S)-3-[4-([2,7]Naphthyridin-1-yloxy)phenyl]-2-{3-[2-(piperidine-1-sulfonyl)phenyl]ureido}propionic acid methyl ester The title compound (93%) was prepared from the compound from Preparation 28 and 2-(piperidine-1-sulfonyl)phenylisocyanate following the procedure described in Example 117.

δ (CDCl3): 9.81 (s, 1H), 8.79 (d, 1H), 8.68 (s, 1H), 8.20 (m, 2H), 7.68 (d, 2H), 7.54 (t, 1H), 7.23 (m, 5H), 7.15 (t, 1H), 5.52 (d, 1H), 4.89 (m, 1H), 3.79 (s, 3H), 3.21 (m, 2H), 3.00 (m, 4H), 1.60 (m, 4H), 1.40 (m, 2H).

Example 140

(S)-3-[4-([2,7]Naphthyridin-1-yloxy)phenyl]-2-{3-[2-(piperidine-1-sulfonyl)phenyl]ureido}propionic acid The title compound (85%) was prepared from the compound of Example 139 by hydrolysis following the procedure described in Example 2.

m.p.: 159° C.

δ (DMSO-d6): 9.68 (s, 1H), 8.81 (d, 1H), 8.45 (s, 1H), 8.14 (d, 1H), 7.96 (d, 2H), 7.89 (d, 1H), 7.65 (d, 1H), 7.53 (m, 2H), 7.38 (d, 2H), 7.24 (d, 2H), 7.15 (t, 1H), 4.38 (m, 1H), 3.16 (m, 1H), 2.92 (m, 5H), 1.46 (m, 4H), 1.33 (m, 2H).

Example 141

(S)-2-[3-(2-Benzylphenyl)-3-methylureido]-3-[4-([2,7]naphthyridin-1-yloxy)phenyl]propionic acid methyl ester The title compound (35%) was prepared from the compound from Preparation 28 following the procedure described in Example 125.

δ (CDCl3): 9.80 (s, 1H), 8.78 (d, 1H), 8.07 (m, 1H), 7.63 (d, 1H), 7.24 (m, 7H), 7.04 (m, 7H), 4.70 (m, 1H), 4.47 (d, 1H), 3.95 (m, 1H), 3.73 (m, 1H), 3.70 (s, 3H), 3.02 (s, 3H), 2.90 (m, 2H).

Example 142

(S)-2-[3-(2-Benzylphenyl)-3-methylureido]-3-[4-([2,7]naphthyridin-1-yloxy)phenyl]propionic acid The title compound (84%) was prepared from the compound of Example 141 by hydrolysis following the procedure described in Example 2.

m.p.: 128° C.

δ (DMSO-d6): 12.82 (bs, 1H), 9.68 (s, 1H), 8.82 (d, 1H), 8.11 (bs, 1H), 7.89 (d, 1H), 7.53 (d, 1H), 7.22 (m, 13H), 5.50 (m, 1H), 4.38 (m, 1H), 3.65 (m, 2H), 3.05 (m, 2H), 2.84 (s, 3H).

Example 143

(S)-2-[3-(2-Benzylphenyl)-3-methylthioureido]-3-(4-{[1-(3,5-dichloropyridin-4-yl)methanoyl]amino}phenyl)propionic acid methyl ester (S)-2-Amino-3-{4-[(3,5-dichloropyridine-4-carbonyl)amino]phenyl}propionic acid methyl ester (0.25 g, 0.62 mmol) was added at room temperature to a tetrahydrofuran solution (3 ml) of thiocarbonyidiimidazol (0.12, 0.68 mmol) and triethylamine (0.062, 0.62 mmol) and stirred for 2 h. Next, the solvent was removed under reduced pressure and compound from Preparation 11 was added in acetonitrile (3 ml) and stirred at 80° C. for 3 h. The solvent was removed under reduced pressure and the residue was purified by flash chromatography (Hexane:AcOEt, 1:1) to yield the title compound(0.23 g, 62%) as a yellow solid.

δ (DMSO-d6): 10.94 (s, 1H), 8.82 (s, 2H), 7.60 to 6.68 (m, 14H), 5.03 (m, 1H), 3.70 (dd, 2H), 3.58 (s, 3H), 3.02 (m, 2H).

Example 144

(S)-2-[3-(2-Benzylphenyl)-3-methylthioureido]-3-(4-{[1-(3,5-dichloropyridin-4-yl)methanoyl]amino}phenyl)propionic acid To a mixed solution of the solid above in methanol/terahydrofuran (1 ml/1 ml) an aqueous solution of sodium hydroxide (2M, 1 ml) was added and stirred at room temperature for 2 h. The organic solvent was removed under reduced pressure and the resulting aqueous solution was acidified with hydrochloric acid (2M, 1 ml). The precipitate was collected by filtration to obtain the title compound (0.09 g, 40%) as a yellow solid.

m.p.: 198° C.

δ (DMSO-d6): 10.92 (s, 1H), 8.78 (s, 2H), 7.58 to 6.82 (m, 14H), 4.84 (m 1H), 3.72 (dd, 2H), 3.00 (m, 2H).

Example 145

(S)-2-{3-[2-(Cyclohexylmethylcarbamoyl)phenyl]-3-methylthioureido}-3-(4-{[1-(3,5-dichloropyridin-4-yl)methanoyl]amino}phenyl)propionic acid methyl ester The title compound was obtained as a pale yellow solid from the compound of Preparation 7 and (S)-2-Amino-3-{4-[(3,5-dichloropyridine-4-carbonyl)amino]phenyl}propionic acid methyl ester hydrochloride following the procedure described in Example 143.

δ (DMSO-d6, mixture of rotamers): 10.94 (s, 1H), 8.82 (s, 2H), 7.60 to 7.05 (m, 9H), 5.15 and 4.92 (m, 1H major/minor), 3.62 (s, 3H), 3.15 (m, 6H), 2.84 and 2.72 (s, 3H major/minor), 1.84 to 0.78 (m, 10H).

Example 146

(S)-2-{3-[2-(Cyclohexylmethylcarbamoyl)phenyl]-3-methylthioureido}-3-(4-{[1-(3,5-dichloropyridin-4-yl)methanoyl]amino}phenyl)propionic acid The title compound (43%) was prepared from the compound of Example 145 by hydrolysis in a similar manner to Example 144.

m.p.: 175° C.

δ (DMSO-d6, mixture of rotamers): 10.92 (s, 1H), 8.78 (s, 2H), 7.60 to 6.95 (m, 9H), 5.00 and 4.96 (m, 1H major/minor), 3.15 (m, 6H), 2.82 and 2.72 (s, 3H minor/major), 1.84 to 0.80 (m, 10H).

Example 147

(S)-3-(4-{[1-(3,5-Dichloropyridin-4-yl)methanoyl]amino}phenyl)-2-{3-[2-piperidine-1-sulfonyl)phenyl]thioureido}propionic acid Isothiocyanate of compound from Preparation 3 (0.85 g, 3 mmol) was added to a solution of (S)-2-Amino-3-{4-[(3,5-dichloropyddine-4-carbonyl)amino]phenyl}propionic acid (0.78 9, 2 mmol) in pyridine/water (1/1, 20 ml) and stirred at room temperature for 3 h. The organic solvent was removed under reduced pressure and the resulting aqueous solution was acidified with hydrochloric acid (2M, 5 ml) and extracted with AcOEt (50 ml). The organic layer was dried (MgSO$_4$) and the solvents removed under reduced pressure. The crude material was purified by flash chromatography (AcOEt:AcOH, 99:1) to yield the title compound (0.66 g, 80%) as a pale yellow solid.

m.p.: 170° C.

δ (DMSO-d6): 10.94 (s, 1H), 9.26 (s, 1H), 9.02 (d, 1H), 8.78 (s, 2H), 7.75 (m, 2H), 7.62 (m, 3H), 7.34 (m, 3H), 5.02 (m, 1H), 3.15 (m, 2H), 2.92 (m, 4H), 1.42 (m, 6H).

The following examples illustrate pharmaceutical compositions according to the present invention and procedure for their preparation.

Example 148

Preparation of a Pharmaceutical Composition: Tablets

| Formulation: | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

Example 149

Preparation of a Pharmaceutical Composition: Tablets Coated

| Formulation: | |
|---|---|
| Compound of the present invention | 5.0 mg |
| Lactose | 95.2 mg |
| Corn starch | 40.8 mg |
| Polyvinylpyrrolidone | 7.5 mg |
| Magnesium stearate | 1.5 mg |
| Hydroxypropylcellulose | 2.3 mg |
| Polyethylene glycol | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 9 of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight. Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

Example 150

Preparation of a Pharmaceutical Composition: Liquid Inhalant

| Formulation: | |
|---|---|
| Compound of the present invention | 400 μg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 1150 for 30 minutes to give liquid inhalant.

Example 151

Preparation of a Pharmaceutical Composition: Powder Inhalant

| Formulation: | |
|---|---|
| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

Example 152

Preparation of a Pharmaceutical Composition: Inhalation Aerosol.

| Formulation: | |
|---|---|
| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A compound of the general Formula Ia:

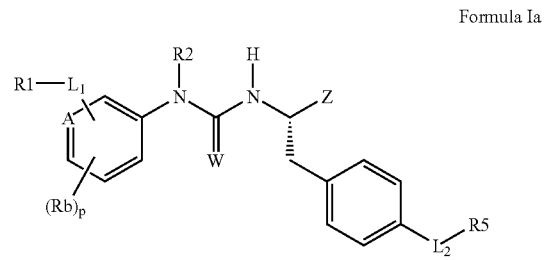

Formula Ia or a pharmaceutically acceptable salt thereof,
wherein:

A represents a —CH— group or a nitrogen atom;

R1 is $C_{3-10}$alkyl, $C_{3-10}$alkenyl, $C_{3-10}$alkynyl, $C_{3-10}$cycloalkyl, $C_{3-10}$cycloalkyl-$C_{1-10}$alkyl, $C_{3-10}$cycloalkyl-$C_{2-10}$alkenyl, $C_{3-10}$cycloalkyl-$C_{2-10}$alkynyl, 3- to 10-membered heterocyclyl, 3- to 10-membered heterocyclyl-$C_{1-10}$alkyl, 3- to 10-membered heterocyclyl-$C_{2-10}$alkenyl, 3- to 10-membered heterocyclyl-$C_{2-10}$alkynyl, $C_{6-10}$aryl, $C_{6-10}$aryl-$C_{1-10}$alkyl, $C_{6-10}$aryl-$C_{2-10}$alkenyl, $C_{6-10}$aryl-$C_{2-10}$alkynyl, 5- to 10-membered heteroaryl, 5- to 10-membered heteroaryl-$C_{1-10}$alkyl, 5- to 10-membered heteroaryl-$C_{2-10}$alkenyl, or 5- to 10-membered heteroaryl-$C_{2-10}$alkynyl; wherein said alkyl, alkenyl, and alkynyl groups or moieties are unsubstituted or substituted with one to four substituents, which may be the same or different and are independently selected from Ra; and wherein said cycloalkyl, heterocyclyl, aryl and heteroaryl groups or moieties are unsubstituted or substituted with one to four substituents, which may be the same or different and are independently selected from Rb;

R2 is hydrogen, $C_{1-6}$-alkyl, $C_{0-2}$alkyl-$C_{3-10}$cycloalkyl, $C_{0-2}$alkyl-$C_{6-10}$aryl, or $C_{0-2}$alkyl-5- to 10-membered heteroaryl, $C_{3-10}$cycloalkyl-$C_{0-2}$alkyl, $C_{6-10}$aryl-$C_{0-2}$ alkyl or 5- to 10-membered heteroaryl-$C_{0-2}$ alkyl, wherein said aryl and heteroaryl groups or moieties are unsubstituted or substituted with one to four substituents, which may be the same or different and are independently selected from Ra;

R5 is $C_{1-6}$-alkyl, $C_{3-10}$cycloalkyl, $C_{3-10}$cycloalkyl-$C_{1-4}$ alkyl, 3- to 10-membered heterocyclyl, 3- to 10-membered heterocyclyl-$C_{1-4}$alkyl, $C_{6-10}$aryl, $C_{6-10}$aryl-$C_{1-4}$ alkyl, 5- to 10-membered heteroaryl, or 5- to 10-membered heteroaryl-$C_{1-4}$alkyl; wherein said alkyl groups or moieties are unsubstituted or substituted with one to four substituents, which may be the same or different and are independently selected from Ra; and wherein said cycloalkyl, heterocyclyl, aryl and heteroaryl groups or moieties are unsubstituted or substituted with one to four substituents, which may be the same or different and are independently selected from Rb;

L1 is —S—, —S(O)—, —S(O)$_2$—, —C(O)—, —C(O)O—, —C(S)—, —N(Rc)—, —CH$_2$—, —CH$_2$N(Rc)—, —CON(Rc)—, —CSN(Rc)—, —N(Rc)CO—, —N(Rc)CS—, —S(O)$_2$N(Rc)— or —N(Rc)S(O)$_2$—;

L2 is a covalent bond, —O—, —S—, —S(O)—, —S(O)$_2$—, —C(O)—, —C(O)O—, —OC(O)—, —C(S)—, —N(Rc)—, —CON(Rc)—, —OC(O)N (Rc), —CSN(Rc)—, —N(Rc)CO—, —N(Rc)C(O)

O—, —N(Rc)CS—, —S(O)$_2$N(Rc)—, —N(Rc)S(O)$_2$—, —N(Rc)CON(Rc)—, or —N(Rc)CSN(Rc)—, wherein if two Rc substituents are present, these may be the same or different;

W is O, S, NH, N(Rc), or NCN;

Z is —C(O)ORd, —P(O)$_2$ORd, —S(O)$_2$ORd, —S(O)$_2$N(Rd)(Rd), —S(O)$_2$N(Re)C(O)Rd, -5-tetrazolyl, or —C(O)Rd; wherein if two Rd groups are present these may be the same or different;

Ra is —ORe, —NO$_2$, halogen, —S(O)Re, —S(O)$_2$Re, —SRe, —S(O)$_2$ORe, —S(O)NReRe —S(O)$_2$NReRe, —NReRe, —O(CReRe)$_m$NReRe, —C(O)Re, —CO$_2$Re, —CO$_2$(CReRe)$_m$CONReRe, —OC(O)Re, —CN, —C(O)NReRe, —NReC(O)Re, —OC(O)NReRe, —NReC(O)ORe, —NReC(O)NReRe, —CRe(N—ORe), —CFH$_2$, —CF$_2$H, or —CF$_3$; wherein if two or more Re groups are present these may be the same or different;

Rb is a group selected from —ORe, —NO$_2$, halogen, —S(O)Re, —S(O)$_2$Re, —SRe, —S(O)$_2$ORe, —S(O)NReRe —S(O)$_2$NReRe, —NReRe, —O(CReRe)$_m$NReRe, —C(O)Re, —CO$_2$Re, —CO$_2$(CReRe)$_m$CONReRe, —OC(O)Re, —CN, —C(O)NReRe, —NReC(O)Re, —OC(O)NReRe, —NReC(O)ORe, —NReC(O)NReRe, —CRe(N—ORe), —CFH$_2$, —CF$_2$H, —CF$_3$, C$_{1-6}$alkyl, C$_{2-4}$alkenyl, C$_{2-4}$alkynyl, C$_{3-10}$cycloalkyl, C$_{3-10}$cycloalkyl-C$_{1-4}$alkyl, 3- to 10-membered heterocyclyl, 3- to 10-membered heterocyclyl-C$_{1-4}$alkyl, C$_{6-10}$aryl, C$_{6-10}$aryl-C$_{1-4}$alkyl, 5- to 10-membered heteroaryl or 5- to 10-membered heteroaryl-C$_{1-4}$alkyl; wherein said alkyl, alkenyl, alkynyl, cycloalkyl, heterocyclyl, aryl and heteroaryl groups or moieties are unsubstituted or substituted with one to four substituents which may be the same or different and are independently selected from Ra;

Rc is hydrogen, C$_{1-10}$alkyl or C$_{3-10}$cycloalkyl; wherein said alkyl or cycloalkyl groups or moieties are unsubstituted or substituted with one to four substituents which may be the same or different and are selected from Ra;

Rd is hydrogen, C$_{1-6}$alkyl, C$_{3-10}$cycloalkyl, C$_{3-10}$cycloalkyl-C$_{1-4}$alkyl, 3- to 10-membered heterocyclyl, 3- to 10-membered heterocyclyl-C$_{1-4}$alkyl, C$_{6-10}$aryl, C$_{6-10}$aryl-C$_{1-4}$alkyl, 5–10-membered heteroaryl, or 5- to 10-membered heteroaryl-C$_{1-4}$alkyl; wherein said alkyl, cycloalkyl, heterocyclyl, aryl and heteroaryl groups or moieties are unsubstituted or substituted with one to four substituents which may be the same or different and are independently selected from Ra;

Re is hydrogen, or C$_{1-4}$alkyl;

p is an integer from 0 to 4; and m is an integer from 1 to 6.

2. A compound according to claim 1, wherein R1 is C$_{3-6}$alkyl, C$_{3-10}$cycloalkyl, C$_{3-10}$cycloalkyl-C$_{1-4}$alkyl, 3- to 10-membered heterocyclyl, 3- to 10-membered heterocyclyl-C$_{1-4}$alkyl, C$_{6-10}$aryl, C$_{6-10}$aryl-C$_{1-4}$alkyl, 5- to 10-membered heteroaryl, 5- to 10-membered heteroaryl-C$_{1-4}$alkyl; wherein said alkyl groups or moieties are unsubstituted.

3. A compound according to claim 1, wherein L1 is —CH$_2$—, —S—, —S(O)—, —S(O)$_2$—, —C(O)—, —NH—, —CON(Rc)—, or —S(O)$_2$N(Rc)—.

4. A compound according to claim 3, wherein L1 is —CH$_2$—, —S(O)—, —S(O)$_2$—, —CON(Rc)—, or —S(O)$_2$N(Rc)—.

5. A compound according to claim 1, wherein R2 is hydrogen, C$_{1-5}$alkyl, cyclohexylmethyl, benzyl or cyclopropylmethyl.

6. A compound according to claim 1, wherein W is S or O.

7. A compound according to claim 1, wherein Z is —COOH or —C(O)O-methyl.

8. A compound according to claim 1, wherein L2 is a covalent bond or a group —N(Rc)CO—, —OC(O)N(Rc)—, —N(Rc)— or —O—.

9. A compound according to claim 1, wherein R5 is an C$_{6-10}$aryl, C$_{6-10}$aryl-C$_{1-4}$alkyl, 5- to 10 membered heteroaryl or 5- to 10-membered heteroaryl-C$_{1-4}$alkyl group.

10. A compound according to claim 1, wherein -L2-R5 represents 3,5-dichloropyridine-4-carbonylamino, N,N-dimethylcarbamoyl, 4-methylpiperazincarbamoyl, 2,6-dichlorobenzylamino, 3,5-dichloropyridin-4-methylenamino, 2-cyanophenyl, 2-methoxyphenyl, [2,6]naphthyridinyloxy, [2,6]naphthyridinylamino, [2,7]naphthyridinyloxy, [2,7]naphthyridinylamino or 3-cyano[1,6]naphthyridinylamino.

11. A compound according to claim 1, wherein the compound of formula Ia has S-configuration at the carbon alpha to the group Z.

12. A compound according to claim 1, wherein the compound of formula Ia is:

(S)-2-{3-[2-(Cyclohexylmethylcarbamoyl)phenyl]ureido}-3-[4-(2,6-dichlorobenzoylamino)phenyl]propionic acid methyl ester (S)-2-{3-[2-(Cyclohexylmethylcarbamoyl)phenyl]ureido}-3-[4-(2,6-dichlorobenzoylamino)phenyl]propionic acid (S)-2-{3-[2-(Cyclohexylmethylcarbamoyl)-6-methoxyphenyl]ureido}-3-[4-(2,6-dichlorobenzoylamino)phenyl]propionic acid methyl ester (S)-2-{3-[2-(Cyclohexylmethylcarbamoyl)-6-methoxyphenyl]ureido}-3-[4-(2,6-dichlorobenzoylamino)phenyl]propionic acid (S)-3-[4-(2,6-Dichlorobenzoylamino)phenyl]-2-{3-[2-(methylphenylcarbamoyl)phenyl]ureido}propionic acid methyl ester (S)-3-[4-(2,6-Dichlorobenzoylamino)phenyl]-2-{3-[2-(methylphenylcarbamoyl)phenyl]ureido}propionic acid (S)-3-[4-(2,6-Dichlorobenzoylamino)phenyl]-2-{3-[2-(piperidine-1-carbonyl)phenyl]ureido}propionic acid methyl ester (S)-3-[4-(2,6-Dichlorobenzoylamino)phenyl]-2-{3-[2-(piperidine-1-carbonyl)phenyl]ureido}propionic acid (S)-3-[4-(2,6-Dichlorobenzoylamino)phenyl]-2-{3-[5-methoxy-2-(piperidine-1-carbonyl)phenyl]ureido}propionic acid methyl ester (S)-3-[4-(2,6-Dichlorobenzoylamino)phenyl]-2-{3-[5-methoxy-2-(piperidine-1-carbonyl)phenyl]ureido}propionic acid (S)-2-{3-[2-(Cyclohexylisopropylcarbamoyl)-5-methoxyphenyl]ureido}-3-[4-(2,6-dichlorobenzoylamino)phenyl]propionic acid methyl ester (S)-2-{3-[2-(Cyclohexylisopropylcarbamoyl)-5-methoxyphenyl]ureido}-3-[4-(2,6-dichlorobenzoylamino)phenyl]propionic acid (S)-3-[4-(2,6-Dichlorobenzoylamino)phenyl]-2-[3-(2-phenylaminophenyl)ureido]propionic acid methyl ester (S)-3-[4-(2,6-Dichlorobenzoylamino)phenyl]-2-[3-(2-phenylaminophenyl)ureido]propionic acid (S)-2-[3-(4-Benzenesulfonylphenyl)ureido]-3-[4-(2,6-dichlorobenzoylamino)phenyl]propionic acid methyl ester (S)-2-[3-(4-Benzenesulfonylphenyl)ureido]-3-[4-(2,6-dichlorobenzoylamino)phenyl]propionic acid (S)-3-[4-(2,6-Dichlorobenzoylamino)phenyl]-2-{3-[4-(4-nitrobenzenesulfonyl)phenyl]ureido}propionic acid methyl ester
(S)-3-[4-(2,6-Dichlorobenzoylamino)phenyl]-2-{3-[4-(4-nitrobenzenesulfonyl)phenyl]ureido}propionic acid
(S)-3-[4-(2,6-Dichlorobenzoylamino)phenyl]-2-{3-[2-methylpiperazine-1-carbonyl)phenyl]ureido}propionic acid
(S)-2-{3-[2-(Butylthiophen-2-ylmethylsulfamoyl)phenyl]ureido}-3-[4-(2,6-dichlorobenzoylamino)phenyl]propionic acid
(S)-3-[4-(2,6-Dichlorobenzoylamino)phenyl]-2-(3-{2-[(thiophen-2-ylmethyl)sulfamoyl]phenyl}ureido)propionic acid
(S)-3-[4-(2,6-Dichlorobenzoylamino)phenyl]-2-[3-(2-phenylsulfamoylphenyl)ureido]propionic acid
(S)-2-[3-(2-Benzenesulfonylphenyl)-3-methylureido]-3-[4-(2,6-dichlorobenzoylamino)phenyl]propionic acid
(S)-2-[3-(2-Benzylcarbamoylphenyl)ureido]-3-[4-(2,6-dichlorobenzoylamino)phenyl]propionic acid
(S)-2-[3-(2-Cyclohexylcarbamoylphenyl)ureido]-3-[4-(2,6-dichlorobenzoylamino)phenyl]propionic acid
(S)-3-[4-(2,6-Dichlorobenzoylamino)phenyl]-2-[3-(2-phenylcarbamoylphenyl)ureido]propionic acid
(S)-2-{3-[2-(Cyclohexylmethylcarbamoyl)phenyl]ureido}-3-[4-(2,6-dichlorobenzoylamino)phenyl]propionic acid
(S)-2-[3-(2-tert-Butylcarbamoylphenyl)ureido]-3-[4-(2,6-dichlorobenzoylamino)phenyl]propionic acid
(S)-3-[4-(2,6-Dichlorobenzoylamino)phenyl]-2-{3-[2,4-dichloro-6-(cyclohexylmethylcarbamoyl)phenyl]ureido}propionic acid
(S)-2-{3-[2-(Cyclohexylmethylcarbamoyl)-6-methylphenyl]ureido}-3-[4-(2,6-dichlorobenzoylamino)phenyl]propionic acid
(S)-2-{3-[2-(Cyclohexylmethylcarbamoyl)phenyl]-3-methylureido}-3-[4-(2,6-dichlorobenzoylamino)phenyl]propionic acid methyl ester
(S)-2-{3-[2-(Cyclohexylmethylcarbamoyl)phenyl]-3-methylureido}-3-[4-(2,6-dichlorobenzoylamino)phenyl]propionic acid
(S)-2-[3-(2-Benzenesulfonylphenyl)ureido]-3-[4-(2,6-dichlorobenzoylamino)phenyl]propionic acid methyl ester
(S)-2-[3-(2-Benzenesulfonylphenyl)ureido]-3-[4-(2,6-dichlorobenzoylamino)phenyl]propionic acid
(S)-3-[4-(2,6-Dichlorobenzoylamino)phenyl]-2-{3-[2-(piperidine-1-sulfonyl)phenyl]ureido}propionic acid methyl ester
(S)-3-[4-(2,6-Dichlorobenzoylamino)phenyl]-2-{3-[2-(piperidine-1-sulfonyl)phenyl]ureido}propionic acid
(S)-2-{3-[2-(Cyclohexylmethylsulfamoyl)phenyl]ureido}-3-[4-(2,6-dichlorobenzoylamino)phenyl]propionic acid methyl ester
(S)-2-{3-[2-(Cyclohexylmethylsulfamoyl)phenyl]ureido}-3-[4-(2,6-dichlorobenzoylamino)phenyl]propionic acid
(S)-2-[3-(2-Benzylphenyl)ureido]-3-[4-(2,6-dichlorobenzoylamino)phenyl]propionic acid methyl ester
(S)-2-[3-(2-Benzylphenyl)ureido]-3-[4-(2,6-dichlorobenzoylamino)phenyl]propionic acid
(S)-3-[4-(2,6-Dichlorobenzoylamino)phenyl]-2-[3-(2-phenylsulfanylphenyl)ureido]propionic acid methyl ester
(S)-3-[4-(2,6-Dichlorobenzoylamino)phenyl]-2-[3-(2-phenylsulfanylphenyl)ureido]propionic acid
(S)-2-{3-[5-Chloro-2-(4-chlorobenzenesulfonyl)phenyl]ureido}-3-[4-(2,6-dichlorobenzoylamino)phenyl]propionic acid methyl ester
(S)-2-{3-[5-Chloro-2-(4-chlorobenzenesulfonyl)phenyl]ureido}-3-[4-(2,6-dichlorobenzoylamino)phenyl]propionic acid
(S)-2-[3-(2-Benzenesulfonyl-5-chlorophenyl)ureido]-3-[4-(2,6-dichlorobenzoylamino)phenyl]propionic acid methyl ester
(S)-2-[3-(2-Benzenesulfonyl-5-chlorophenyl)ureido]-3-[4-(2,6-dichlorobenzoylamino)phenyl]propionic acid
(S)-2-{3-[2,4-Dibromo-6-(cyclohexylmethylcarbamoyl)phenyl]ureido}-3-[4-(2,6-dichlorobenzoylamino)phenyl]propionic acid methyl ester
(S)-2-{3-[2,4-Dibromo-6-(cyclohexylmethylcarbamoyl)phenyl]ureido}-3-[4-(2,6-dichlorobenzoylamino)phenyl]propionic acid
(S)-3-[4-(2,6-Dichlorobenzoylamino)phenyl]-2-{3-[2-(toluene-4-sulfonyl)-5-trifluoromethylphenyl]ureido}propionic acid methyl ester
(S)-3-[4-(2,6-Dichlorobenzoylamino)phenyl]-2-{3-[2-(toluene-4-sulfonyl)-5-trifluoromethylphenyl]ureido}propionic acid
(S)-2-{3-[2-Chloro-5-(toluene-4-sulfonyl)phenyl]ureido}-3-[4-(2,6-dichlorobenzoylamino)phenyl]propionic acid methyl ester
(S)-2-{3-[2-Chloro-5-(toluene-4-sulfonyl)phenyl]ureido}-3-[4-(2,6-dichlorobenzoylamino)phenyl]propionic acid
(S)-2-{3-[5-Chloro-2-(2,5-dimethoxybenzenesulfonyl)phenyl]ureido}-3-[4-(2,6-dichlorobenzoylamino)phenyl]propionic acid methyl ester
(S)-2-{3-[5-Chloro-2-(2,5-dimethoxybenzenesulfonyl)phenyl]ureido}-3-[4-(2,6-dichlorobenzoylamino)phenyl]propionic acid
(S)-2-[3-(2-Benzenesulfonylpyridin-3-yl)ureido]-3-[4-(2,6-dichlorobenzoylamino)phenyl]propionic acid methyl ester
(S)-2-[3-(2-Benzenesulfonylpyridin-3-yl)ureido]-3-[4-(2,6-dichlorobenzoylamino)phenyl]propionic acid
(S)-2-[3-(2-Benzenesulfonylphenyl)ureido]-3-(2',6'-dimethoxybiphenyl-4-yl)propionic acid methyl ester
(S)-2-[3-(2-Benzenesulfonylphenyl)ureido]-3-(2',6'-dimethoxybiphenyl-4-yl)propionic acid
(S)-3-{4-[(3,5-Dichloropyridine-4-carbonyl)amino]phenyl}-2-{3-[2-(piperidine-1-sulfonyl)phenyl]ureido}propionic acid methyl ester
(S)-3-{4-[(3,5-Dichloropyridine-4-carbonyl)amino]phenyl}-2-{3-[2-(piperidine-1-sulfonyl)phenyl]ureido}propionic acid
(S)-2-{3-[5-Chloro-2-(2,5-dimethoxybenzenesulfonyl)phenyl]ureido}-3-{4-[(3,5-dichloropyridine-4-carbonyl)amino]phenyl}propionic acid methyl ester
(S)-2-{3-[5-Chloro-2-(2,5-dimethoxybenzenesulfonyl)phenyl]ureido}-3-{4-[(3,5-dichloropyridine-4-carbonyl)amino]phenyl}propionic acid
(S)-2-{3-[2-(Cyclohexylmethylsulfamoyl)phenyl]ureido}-3-{4-[(3,5-dichloropyridine-4-carbonyl)amino]phenyl}propionic acid methyl ester
(S)-2-{3-[2-(Cyclohexylmethylsulfamoyl)phenyl]ureido}-3-{4-[(3,5-dichloropyridine-4-carbonyl)amino]phenyl}propionic acid
(S)-2-[3-(2-Benzenesulfonyl-5-chlorophenyl)ureido]-3-{4-[(3,5-dichloropyridine-4-carbonyl)amino]phenyl}propionic acid methyl ester (S)-2-[3-(2-Benzenesulfonyl-5-chlorophenyl)ureido]-3-{4-[(3,5-dichloropyridine-4-carbonyl)amino]phenyl}propionic acid (S)-2-[3-(2-Benzenesulfonylphenyl)ureido]-3-{4-[(3,5-dichloropyridine-4-carbonyl)amino]phenyl}propionic acid methyl ester (S)-2-[3-(2-Benzenesulfonylphenyl)ureido]-3-{4-[(3,5-dichloropyridine-4-carbonyl)amino]phenyl}propionic acid (S)-3-[4-(2,6-Dichlorobenzoylamino)phenyl]-2-{3-[2-(toluene-4-sulfonyl)pyridin-3-yl]ureido}propionic acid methyl ester (S)-3-[4-(2,6-Dichlorobenzoylamino)phenyl]-2-{3-[2-(toluene-4-sulfonyl)pyridin-3-yl]ureido}propionic acid (S)-2-{3-[2-(4-Chlorobenzenesulfonyl)pyridin-3-yl]ureido}-3-[4-(2,6-dichlorobenzoylamino)phenyl]propionic acid methyl ester (S)-2-{3-[2-(4-Chlorobenzenesulfonyl)pyridin-3-yl]ureido}-3-[4-(2,6-dichlorobenzoylamino)phenyl]propionic acid (S)-3-[4-(2,6-Dichlorobenzoylamino)phenyl]-2-{3-methyl-3-[2-(piperdine-1-sulfonyl)phenyl]ureido}propionic acid methyl ester (S)-3-[4-(2,6-Dichlorobenzoylamino)phenyl]-2-{3-methyl-3-[2-(piperidine-1-sulfonyl)phenyl]ureido}propionic acid (S)-3-(4-{[1-(3,5-Dichloropyridin-4-yl)methanoyl]amino}phenyl)-2-{3-[3-(1-phenylmethanoyl)phenyl]ureido}propionic acid (S)-2-[3-(2-Benzylphenyl)-3-methylureido]-3-(4-{[1-(3,5-dichloropyridin-4-yl)methanoyl]amino}-phenyl)propionic acid methyl ester (S)-2-[3-(2-Benzylphenyl)-3-methylureido]-3-(4-{[1-(3,5-dichloropyridin-4-yl)methanoyl]amino}phenyl)propionic acid (S)-2-{3-[2-(Cyclohexylmethylcarbamoyl)phenyl]ureido}-3-(4-{[1-(3,5-dichloropyridin-4-yl)methanoyl]amino}phenyl)propionic acid (S)-2-{3-[2-(Cyclohexylmethylcarbamoyl)phenyl]-3-methylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-propylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-cyclopropylmethylureido}-3-(4-{[1-(3,5-dichloropyridin-4-yl)methanoyl]amino}phenyl)propionic acid (S)-2-{3-[2-(Cyclohexylmethylcarbamoyl)phenyl]-3-pentylureido}-3-(4-{[1-(3,5-dichloropyridin-4-yl)methanoyl]amino}phenyl)propionic acid (S)-2-{3-Benzyl-3-[2-(cyclohexylmethylcarbamoyl)phenyl]ureido}-3-(4-{[1-(3,5-dichloropyridin-4-yl)methanoyl]amino}phenyl)propionic acid (S)-2-{3-Cyclohexylmethyl-3-[2-(cyclohexylmethylcarbamoyl)phenyl]ureido}-3-(4-{[1-(3,5-dichloropyridin-4-yl)methanoyl]amino}phenyl)propionic acid (S)-3-(4-{[1-(3,5-Dichloropyridin-4-yl)methanoyl]amino}phenyl)-2-{3-methyl-3-[2-(piperidine-1-sulfonyl)phenyl]ureido}propionic acid methyl ester (S)-3-(4-{[1-(3,5-Dichloropyridin-4-yl)methanoyl]amino}phenyl)-2-{3-methyl-3-[2-(piperidine-1-sulfonyl)phenyl]ureido}propionic acid (S)-3-(4-{[1-(3,5-Dichloropyridin-4-yl)methanoyl]amino}phenyl)-2-{3-[2-(4-methylpiperazine-1-sulfonyl)phenyl]ureido}propionic acid methyl ester (S)-3-(4-{[1-(3,5-Dichloropyridin-4-yl)methanoyl]amino}phenyl)-2-{3-[2-(4-methylpiperazine-1-sulfonyl)phenyl]ureido}propionic acid (S)-2-[3-(2-Cyclopentanesulfonylphenyl)ureido]-3-(4-{[1-(3,5-dichloropyridin-4-yl)methanoyl]amino}phenyl)propionic acid methyl ester (S)-2-[3-(2-Cyclopentanesulfonylphenyl)ureido]-3-(4-{[1-(3,5-dichloropyridin-4-yl)methanoyl]amino}phenyl)propionic acid (S)-3-(4-{[1-(3,5-Dichloropyridin-4-yl)methanoyl]amino}phenyl)-2-{3-[2-(2-methylpropane-2-sulfonyl)phenyl]ureido}propionic acid methyl ester (S)-3-(4-{[1-(3,5-Dichloropyridin-4-yl)methanoyl]amino}phenyl)-2-{3-[2-(2-methylpropane-2-sulfonyl)phenyl]ureido}propionic acid (S)-3-(4-{[1-(3,5-Dichloropyridin-4-yl)methanoyl]amino}phenyl)-2-{3-[2-(7-methylthieno[2,3-b]pyrazin-3-ylsulfanyl)phenyl]ureido}propionic acid methyl ester (S)-3-(4-{[1-(3,5-Dichloropyridin-4-yl)methanoyl]amino}phenyl)-2-{3-[2-(7-methylthieno[2,3-b]pyrazin-3-ylsulfanyl)phenyl]ureido}propionic acid (S)-3-(4-{[1-(3,5-Dichloropyridin-4-yl)methanoyl]amino}phenyl)-2-{3-[2-(3,5-dichloropyridin-4-ylsulfanyl)phenyl]ureido}propionic acid methyl ester (S)-3-(4-{[1-(3,5-Dichloropyridin-4-yl)methanoyl]amino}phenyl)-2-{3-[2-(3,5-dichloropyridin-4-ylsulfanyl)phenyl]ureido}propionic acid (S)-3-(4-{[1-(3,5-Dichloropyridin-4-yl)methanoyl]amino}phenyl)-2-{3-[2-(piperidine-1-sulfonyl)phenyl]ureido}propionic acid methyl ester (S)-3-(4-{[1-(3,5-Dichloropyridin-4-yl)methanoyl]amino}phenyl)-2-{3-[2-(piperidine-1-sulfonyl)phenyl]ureido}propionic acid (S)-3-(4-{[1-(3,5-Dichloropyridin-4-yl)methanoyl]amino}phenyl)-2-{3-methyl-3-[2-(piperazine-1-sulfonyl)phenyl]ureido}propionic acid methyl ester (S)-3-(4-{[1-(3,5-Dichloropyridin-4-yl)methanoyl]amino}phenyl)2-{3-methyl-3-[2-(piperazine-1-sulfonyl)phenyl]ureido}propionic acid (S)-2-[3-(2-Benzenesulfonylphenyl)ureido]-3-(4-{[1-(2-chloro-6-methylpyridin-3-yl)methanoyl]amino}phenyl)propionic acid (S)-2-[3-(2-Benzenesulfonylphenyl)ureido]-3-(4-{[1-(2,6-dichloropyridin-3-yl)-methanoyl]amino}phenyl)propionic acid (S)-2-[3-(2-Benzenesulfonylphenyl)ureido]-3-(4-{[1-(3,5-dimethoxypyridin-4-yl)-methanoyl]amino}phenyl)propionic acid (S)-2-[3-(2-Benzenesulfonylphenyl)ureido]-3-(4-{[1-(3,5-dibromopyridin-4-yl)-methanoyl]amino}phenyl)propionic acid (S)-2-[3-(2-Benzenesulfonylphenyl)ureido]-3-[4-(2,6-dichlorobenzylamino)phenyl]propionic acid methyl ester (S)-2-[3-(2-Benzenesulfonylphenyl)ureido]-3-[4-(2,6-dichlorobenzylamino)phenyl]propionic acid (S)-2-[3-(2-Benzenesulfonylphenyl)ureido]-3-{4-[(3,5-dichloropyrdin-4-ylmethyl)amino]phenyl}propionic acid methyl ester (S)-2-[3-(2-Benzenesulfonylphenyl)ureido]-3-{4-[(3,5-dichloropyridin-4-ylmethyl)amino]phenyl}propionic acid (S)-2-[3-(2-Benzenesulfonylphenyl)ureido]-3-(4-dimethylcarbamoyloxyphenyl)propionic acid methyl ester (S)-2-[3-(2-Benzenesulfonylphenyl)ureido]-3-(4-dimethylcarbamoyloxyphenyl)propionic acid 4-Methylpiperazine-1-carboxylic acid 4-{(S)-2-[3-(2-benzenesulfonylphenyl)ureido]-2-methoxycarbonylethyl}phenyl ester 4-Methylpiperazine-1-carboxylic acid 4-{(S)-2-[3-(2-benzenesulfonylphenyl)ureido]-2-carboxyethyl}phenyl ester 3,5-Dichloroisonicotinic acid 4-{(S)-2-[3-(2-benzenesulfonylphenyl)ureido]-2-methoxycarbonylethyl}phenyl ester 3,5-Dichloroisonicotinic acid 4-{(S)-2-[3-(2-benzenesulfonylphenyl)ureido]-2-carboxyethyl}phenyl ester (S)-3-(2'-Cyanobiphenyl-4-yl)-2-{3-[2-(piperidine-1-sulfonyl)phenyl]ureido}propionic acid methyl ester (S)-3-(2'-Cyanobiphenyl-4-yl)-2-{3-[2-(piperidine-1-sulfonyl)phenyl]ureido}propionic acid (S)-3-(2'-Methoxybiphenyl-4-yl)-2-{3-[2-(piperidine-1-sulfonyl)phenyl]ureido}propionic acid methyl ester (S)-3-(2'-Methoxybiphenyl-4-yl)-2-{3-[2-(piperidine-1-sulfonyl)phenyl]ureido}propionic acid (S)-2-[3-(2-Benzenesulfonylphenyl)ureido]-3-[4-([2,6]naphthyridin-1-ylamino)phenyl]propionic acid methyl ester (S)-2-[3-(2-Benzenesulfonylphenyl)ureido]-3-[4-([2,6]naphthyridin-1-ylamino)phenyl]propionic acid (S)-3-[4-([2,6]Naphthyridin-1-ylamino)phenyl]-2-{3-[2-(piperidine-1-sulfonyl)phenyl]ureido}propionic acid methyl ester (S)-3-[4-([2,6]Naphthyridin-1-ylamino)phenyl]-2-{3-[2-(piperidine-1-sulfonyl)phenyl]ureido}propionic acid (S)-2-[3-(2-Benzylphenyl)-3-methylureido]-3-[4-([2,6]naphthyridin-1-ylamino)phenyl]propionic acid methyl ester (S)-2-[3-(2-Benzylphenyl)-3-methylureido]-3-[4-([2,6]naphthyridin-1-ylamino)phenyl]propionic acid (S)-2-[3-(2-Benzenesulfonylphenyl)ureido]-3-[4-([2,7]naphthyridin-1-ylamino)phenyl]propionic acid methyl ester (S)-2-[3-(2-Benzenesulfonylphenyl)ureido]-3-[4-([2,7]naphthyridin-1-ylamino)phenyl]propionic acid (S)-3-[4-([2,7]Naphthyridin-1-ylamino)-phenyl]-2-{3-[2-(piperidine-1-sulfonyl)phenyl]ureido}propionic acid methyl ester (S)-3-[4-([2,7]Naphthyridin-1-ylamino)-phenyl]-2-{3-[2-(piperidine-1-sulfonyl)phenyl]ureido}propionic acid (S)-2-[3-(2-Benzylphenyl)-3-methylureido]-3-[4-([2,7]naphthyridin-1-ylamino)phenyl]propionic acid methyl ester (S)-2-[3-(2-Benzylphenyl)-3-methylureido]-3-[4-([2,7]naphthyridin-1-ylamino)phenyl]propionic acid (S)-2-[3-(2-Benzenesulfonylphenyl)ureido]-3-[4-([2,6]naphthyridin-1-yloxy)phenyl]propionic acid methyl ester (S)-2-[3-(2-Benzenesulfonylphenyl)ureido]-3-[4-([2,6]naphthyridin-1-yloxy)phenyl]propionic acid (S)-3-[4-([2,6]Naphthyridin-1-yloxy)phenyl]-2-{3-[2-(piperidine-1-sulfonyl)phenyl]ureido}propionic acid methyl ester (S)-3-[4-([2,6]Naphthyridin-1-yloxy)phenyl]-2-{3-[2-(piperidine-1-sulfonyl)phenyl]ureido}propionic acid (S)-2-[3-(2-Benzenesulfonylphenyl)ureido]-3-[4-([2,7]naphthyridin-1-yloxy)phenyl]propionic acid methyl ester (S)-2-[3-(2-Benzenesulfonylphenyl)ureido]-3-[4-([2,7]naphthyridin-1-yloxy)phenyl]propionic acid (S)-3-[4-([2,7]Naphthyridin-1-yloxy)phenyl]-2-{3-[2-(piperidine-1-sulfonyl)phenyl]ureido}propionic acid methyl ester (S)-3-[4-([2,7]Naphthyridin-1-yloxy)phenyl]-2-{3-[2-(piperidine-1-sulfonyl)phenyl]ureido}propionic acid (S)-2-[3-(2-Benzylphenyl)-3-methylureido]-3-[4-([2,7]naphthyridin-1-yloxy)phenyl]propionic acid methyl ester (S)-2-[3-(2-Benzylphenyl)-3-methylureido]-3-[4-([2,7]naphthyridin-1-yloxy)phenyl]propionic acid (S)-2-[3-(2-Benzylphenyl)-3-methylthioureido]-3-(4-{[1-(3,5-dichloropyridin-4-yl)methanoyl]amino}phenyl)propionic acid methyl ester (S)-2-[3-(2-Benzylphenyl)-3-methylthioureido]-3-(4-{[1-(3,5-dichloropyridin-4-yl)methanoyl]amino}phenyl)propionic acid (S)-2-{3-[2-(Cyclohexylmethylcarbamoyl)phenyl]-3-methylthioureido}-3-(4-{[1-(3,5-dichloropyridin-4-yl)methanoyl]amino}phenyl)propionic acid methyl ester (S)-2-{3-[2-(Cyclohexylmethylcarbamoyl)phenyl]-3-methylthioureido}-3-(4-{[1-(3,5-dichloropyridin-4-yl)methanoyl]amino}phenyl)propionic acid; or (S)-3-(4-{[1-(3,5-Dichloropyridin-4-yl)methanoyl]amino}phenyl)-2-{3-[2-(piperidine-1-sulfonyl)phenyl]thioureido}propionic acid, or a pharmaceutically acceptable salt thereof.

13. A process for producing a compound of formula Ia as defined in any one of claim 1, and in which the group Z is a —COORd group and R2 is H, which process comprises reacting an amine of formula (III):

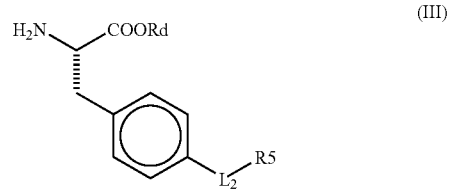

wherein Rd, R5 and L2 are as defined in any one of claim 1 with a corresponding isocyanate or isothiocyanate of formula (IV):

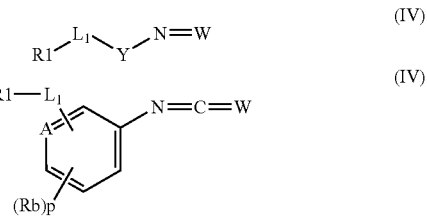

wherein W is O or S and A, R1, L1, Rb and p are as defined in claim 1.

14. A process for producing a compound of formula Ia as defined in claim 1, and in which the group Z is a —COORd group and R2 is as defined in claim 1, which process comprises reacting an amine of formula (VI):

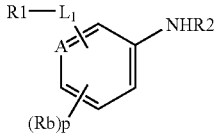
(VI)

wherein A, R1, R2, L1, Rb and p are as defined in claim 1 with an isocyanate or isothiocyanate of formula (VII):

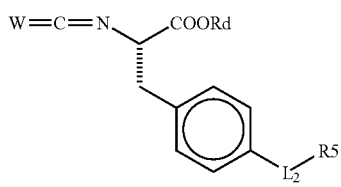
(VII)

wherein W is O or S and R5, Rd and L2 are as defined in claim 1.

15. A process for producing a compound of formula Ia as defined in claim 1, and in which the group Z is a —COORd group and R2 is defined in claim 1, which process comprises reacting an amine of formula (III):

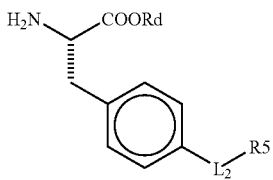
(III)

wherein R5, Rd, and L2 are as defined in claim 1 with a carbamyl chloride of formula (IX):

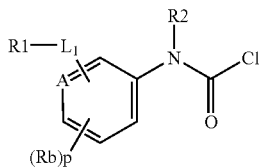
(IX)

wherein A, Rb, p, R1, R2 and L1 are as defined in claim 1.

16. A composition comprising a compound as claimed in claim 1, and a carrier.

17. A compound as claimed in claim 1, wherein the compound is (S)-3-[4-(2,6-Dichlorobenzoylamino)phenyl]-2-{3-[2-(piperidine-1-sulfonyl)phenyl]ureido}propionic acid.

18. A compound as claimed in claim 1, wherein the compound is (S)-2-{3-[2-(Cyclohexylmethylsulfamoyl)phenyl]ureido}-3-{4-[(3,5-dichloropyridine-4-carbonyl)amino]phenyl}propionic acid.

19. A compound as claimed in claim 1, wherein the compound is (S)-2-[3-(2-Benzenesulfonyl-5-chlorophenyl)ureido]-3-{4-](3,5-dichloropyridine-4-carbonyl)amino]phenyl}propionic acid.

20. A compound as claimed in claim 1, wherein the compound is (S)-2-[3-(2-Benzylphenyl)-3-methylureido]-3-(4-{[1-(3,5-dichloropyridin-4-yl)methanoyl]amino}phenyl)propionic acid.

21. A compound as claimed in claim 1, wherein the compound is (S)-2-{3-[2-(Cyclohexylmethylcarbamoyl)phenyl]ureido}-3-(4-{[1-(3,5-dichloropyridin-4-yl)methanoyl]amino}phenyl)propionic acid.

22. A compound as claimed in claim in claim 1, wherein the compound is (S)-2-{3-[2-(Cyclohexylmethylcarbamoyl)phenyl]-3-methYlureido}-3-(4-}]1-(3,5-dichloropyridin-4-yl)methanoyl]amino}Phenyl)propionic acid.

23. A compound as claimed in claim 1, wherein the compound is (S)-2-[3-(2-Benzenesulfonylphenyl)ureido]-3-{4-([2,6]naphthyridin-1-yloxy)phenyl]propionic acid.

* * * * *

UNITED STATES PATENT AND TRADEMARK OFFICE
CERTIFICATE OF CORRECTION

PATENT NO.       : 7,253,171 B2
APPLICATION NO.  : 10/466665
DATED            : August 7, 2007
INVENTOR(S)      : Jimenez Mayorga et al.

It is certified that error appears in the above-identified patent and that said Letters Patent is hereby corrected as shown below:

In claim 1, column 73, line 44, "5–10-membered" should read --5- to 10-membered--.

In claim 9, column 74, line 9, "10 membered" should read --10-membered--.

In claim 12, column 77, lines 34-36,
"(S)-2-[3-(2-Benzylphenyl)-3-methylureido]-3-(4-{[1-(3,5-dichloropyridin-4-yl)methanoyl]amino}phenyl)propionic acid"
    should read
--(S)-2-[3-(2-Benzylphenyl)-3-methylureido]-3-(4-{[1-(3,5-dichloropyridin-4-yl)methanoyl]amino}-phenyl)propionic acid--.

In claim 12, column 78, lines 38-40,
"(S)-3-(4-{[1-(3,5-Dichloropyridin-4-yl)methanoyl]amino}phenyl)
2-{3-methyl-3-[2-(piperazine-1-sulfonyl)phenyl]ureido}propionic acid"
    should read
--(S)-3-(4-{[1-(3,5-Dichloropyridin-4-yl)methanoyl]amino}phenyl)
-2-{3-methyl-3-[2-(piperazine-1-sulfonyl)phenyl]ureido}propionic acid--.

In claim 12, column 78, lines 58-60
"(S)-2-[3-(2-Benzenesulfonylphenyl)ureido]-3-{4-[(3,5-dichloropyrdin-4-ylmethyl)amino]phenyl}propionic acid methyl ester"
    should read
--(S)-2-[3-(2-Benzenesulfonylphenyl)ureido]-3-{4-[(3,5-dichloropyridin-4-ylmethyl)amino]phenyl}propionic acid methyl ester--.

In claim 13, column 80, line 35, after "defined in", delete "any one of."

In claim 13, column 80, line 49, after "defined in", delete "any one of."

UNITED STATES PATENT AND TRADEMARK OFFICE
CERTIFICATE OF CORRECTION

PATENT NO.       : 7,253,171 B2
APPLICATION NO.  : 10/466665
DATED            : August 7, 2007
INVENTOR(S)      : Jimenez Mayorga et al.

It is certified that error appears in the above-identified patent and that said Letters Patent is hereby corrected as shown below:

In claim 13, column 80, lines 53-56, delete the following structure:
"                                                                "

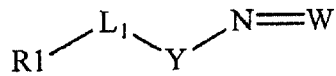

(IV).

In claim 19, column 82, lines 25-27
"(S)-2-[3-(2-Benzenesulfonyl-5-chlorophenyl)ureido]-3-{4-](3,5-dichloropyridine-4-carbonyl)amino]phenyl}propionic acid"
     should read
--(S)-2-[3-(2-Benzenesulfonyl-5-chlorophenyl)ureido]-3-{4-[(3,5-dichloropyridine-4-carbonyl)amino]phenyl}propionic acid--.

In claim 22, column 82, line 36, "as claimed in claim in claim 1," should read --as claimed in claim 1,--.

In claim 22, column 82, lines 37-39,
"(S)-2-{3-[2-(Cyclohexylmethylcarbamoyl)phenyl]-3-methYlureido}-3-(4-}]1-(3,5-dichloropyridin-4-yl)methanoyl]amino}Phenyl) propionic acid"
     should read
--(S)-2-{3-[2-(Cyclohexylmethylcarbamoyl)phenyl]-3-methylureido}-3-(4-{[1-(3,5-dichloropyridin-4-yl)methanoyl]amino}phenyl) propionic acid--.

UNITED STATES PATENT AND TRADEMARK OFFICE
CERTIFICATE OF CORRECTION

PATENT NO. : 7,253,171 B2
APPLICATION NO. : 10/466665
DATED : August 7, 2007
INVENTOR(S) : Jimenez Mayorga et al.

It is certified that error appears in the above-identified patent and that said Letters Patent is hereby corrected as shown below:

In claim 23, column 82, lines 41-42,
"(S)-2-[3-(2-Benzenesulfonylphenyl)ureido]-3-{4-([2,6]naphthyridin-1-yloxy)phenyl] propionic acid"
should read
--(S)-2-[3-(2-Benzenesulfonylphenyl)ureido]-3-[4-([2,6]naphthyridin-1-yloxy)phenyl] propionic acid--.

Signed and Sealed this

Twenty-ninth Day of January, 2008

JON W. DUDAS
*Director of the United States Patent and Trademark Office*